United States Patent
Marroquin Belaunzaran et al.

(10) Patent No.: US 12,383,602 B2
(45) Date of Patent: Aug. 12, 2025

(54) HLA-B57 OPEN CONFORMERS

(71) Applicants: UNIVERSITAT ZURICH, Zurich (CH); UNIVERSITAT BASEL, Basel (CH)

(72) Inventors: Osiris Marroquin Belaunzaran, Zurich (CH); Ulf Petrausch, Zurich (CH); Christoph Renner, Zurich (CH)

(73) Assignees: UNIVERSITAT ZURICH, Zurich (CH); UNIVERSITAT BASEL, Basel (CH)

( * ) Notice: Subject to any disclaimer, the term of this patent is extended or adjusted under 35 U.S.C. 154(b) by 470 days.

(21) Appl. No.: 17/849,643

(22) Filed: Jun. 26, 2022

(65) Prior Publication Data

US 2022/0339250 A1    Oct. 27, 2022

Related U.S. Application Data

(63) Continuation of application No. 16/083,508, filed as application No. PCT/EP2017/055373 on Mar. 7, 2017, now Pat. No. 11,369,660.

(30) Foreign Application Priority Data

Mar. 8, 2016  (EP) ..................... 16159099

(51) Int. Cl.
   A61K 38/17   (2006.01)
   A61P 35/00   (2006.01)
   A61P 37/02   (2006.01)
   C07K 14/74   (2006.01)

(52) U.S. Cl.
   CPC .......... *A61K 38/1774* (2013.01); *A61P 35/00* (2018.01); *A61P 37/02* (2018.01); *C07K 14/70539* (2013.01); *C07K 2319/30* (2013.01)

(58) Field of Classification Search
   CPC ............. C07K 14/70539; A61K 38/1774
   See application file for complete search history.

(56) References Cited

U.S. PATENT DOCUMENTS

| | | | |
|---|---|---|---|
| 2006/0013474 | A1 | 1/2006 | Kochi |
| 2006/0134744 | A1 | 6/2006 | Hildebrand |
| 2011/0219464 | A1 | 9/2011 | Domon |
| 2013/0078253 | A1 | 3/2013 | Fang |
| 2013/0259876 | A1 | 10/2013 | Murphy |
| 2015/0125456 | A1 | 5/2015 | Kim |

FOREIGN PATENT DOCUMENTS

| | | |
|---|---|---|
| CN | 1849395 | 10/2006 |
| CN | 102227214 | 10/2011 |
| CN | 102958942 | 3/2013 |
| CN | 103184291 | 7/2013 |
| JP | 2005503152 | 2/2005 |
| WO | 1999058557 | 11/1999 |
| WO | 2004029071 | 4/2004 |
| WO | 2007011044 | 1/2007 |
| WO | 2015022669 | 2/2015 |
| WO | 2015153969 | 10/2015 |
| WO | 2016124661 | 8/2016 |

OTHER PUBLICATIONS

Bork. Powers and Pitfalls in Sequence Analysis: The 70% Hurdle. Genome Research, 2000, 10:398-400 (Year: 2000).*
Greenspan et al. 1999. Defining epitopes: It's not as easy as it seems; Nature Biotechnology, 17:936-937 (Year: 1999).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine ResidueJ. Cell Biol. 111:2129-2138, 1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Ploegh et al, Proc. Natl. Acad. Sci. USA, vol. 77, No. 10, pp. 6081-6085, (Year 1980).*
Arosa et al: "Open conformers: the hidden face of MHC-I molecules", Trends in Immunology (2007), vol. 28, No. 3, pp. 115-123.
Stephens et al: "HIV-1 diversity versus HLA class I polymorphism", Trends in Immunology (2005), vol. 26, No. 1, pp. 41-47.
Smith et al: "Characterization of signaling function and expression of HLA class I molecules in medulloblastoma", Journal of Neuro-Oncology (2010), vol. 103, No. 2, pp. 197-206.
Zhao et al: "[beta]2-Microglobulin-free HLA-G activates natural killer cells by increasing cytotoxicity and proinflammatory cytokine production", Human Immunology (2013), vol. 74, No. 4, pp. 417-424.
Kao et al: "Evaluation of individual specificities of class I HLA on platelets by a newly developed monoclonal antibody", Human Immonulogy (1990), vol. 27, No. 4, pp. 285-297.
Maohua et al: "Dimerization of solubla HLA-G by IgG-Fc fragment augments ILT2-mediated inhibition of T-cell alloresponse", Transplantation (2009), vol. 87, No. 1, pp. 8-15.

(Continued)

*Primary Examiner* — Prema M Mertz
(74) *Attorney, Agent, or Firm* — JMB Davis Ben-David

(57) ABSTRACT

The invention relates to a HLA-B57 open conformer or a HLA-B57 Fc fusion protein for use in the treatment or prevention of cancer. The Fc open conformer comprises or consists of a first and a second monomer, and each monomer comprises a HLA-B57 chain. The Fc fusion protein further comprises a protein stabilizing polypeptide sequence and optionally an amino acid linker. Further aspects of the invention provide combination medicaments comprising the HLA-B57 Fc open conformer and immune checkpoint inhibitors and/or checkpoint agonist agents. Furthermore, the invention relates to the use of HLA-B57 open conformer as an immunomodulator, particularly in diseases where modulation of diverse immune cell components (e.g. cytotoxic CD8+ T cells, Tregs) is a therapeutic strategy, e.g. infectious diseases.

6 Claims, 18 Drawing Sheets

Specification includes a Sequence Listing.

(56) References Cited

OTHER PUBLICATIONS

MHC class I antigen, partial [Homo sapiens]; GenBank Accession No. AAL18239; 2001.
MHC class I antigen, partial [*Homo sapiens*]; GenBank Accession No. AAQ13833, 2004.
Beers and Berkow, The Merck Manual (1999), vol. 17, pp. 986-995.
Rao et al: "Anti-PD-1/PD-L1 therpy for infectious diseases: learning from the cancer paradigm", International journal of infectious Diseases (2017), vol. 56, pp. 221-228.
Pauken et al: "The PD-1 Pathway regulates Development and function of memory CD8+ T cells following respiratory viral infection", Cell Rep. (2020), Author Manuscript.
Ayodele et al: "Immuntherapy in soft-tissue sarcoma", Current Oncology (2020), (S1): 17-23.
Levy F et al: "CO-Expression of the Human HLA-B27 Class I Antigen and the E3/19K Protein of Adenovirus-2 in Insect Cells Using a Baculovirus Vector", International Immunology, Oxford University Press, GB, vol. 2, No. 10, Jan. 1, 1990 (Jan. 1, 1990), pp. 995-1002, XP001106051, ISSN: 0953-8178.
Santos Susana G et al: "Induction of HLA-B27 heavy chain homodimer formation after activation in dendritic cells.", Arthritis Research & Therapy 2008, vol. 10, No. 4, 2008, p. R100, XP0216803, ISSN: 1478-6362.
R. Tarazona et al: "HLA-B2702 (77-83/83-77) Peptide Binds toTubulin on Human NK Cells and Blocks Their Cytotoxic Capacity", The Journal of Immunology, vol. 165, No. 12, Dec. 15, 2000 (Dec. 15, 2000), pp. 6776-6782, XP055257084, US, ISSN: 0022-1767, 001: 10.4049/jimmunol. 165.12.6776.
Guillermo Mazzolini et al: "Immunotherapy and immunoescape in colorectal cancer", World Journal of Gastroenterology, vol. 13, No. 44, Nov. 1, 2007 (Nov. 1, 2007), pp. 5822-5831, XP055257553, CN, ISSN: 1007-9327, 001 : 10.3748/wjg.v13.i44.5822.
Dolan et al. Cancer Control. 21(3): 231-237, Jul. 2014.
Yu et al. Targeted Delivery of an Antigenic Peptide to the Endoplasmic Reticulum: Application for Development of a Peptide Therapy for Ankylosing Spondylitis. PLOS ONE 8 (10): 1-14, published Oct. 14, 2013.

Ciprandi G et al: "Soluble HLA-G and HLA-A,-B,-C serum levels in patients with allergic rhinitis", Allergy (Oxford), vol. 63, No. 10, Oct. 2008 (Oct. 2008), pp. 1335-1338, XP002770154, ISSN: 0105-4538.
Luthra-Guptasarma M et al: "HLA-B27 lacking associated beta2-microglobulin rearranges to auto-display or cross-display residues 169-181: a novel molecular mechanism for spondyloarthropathies", FEBS Letters, Elsevier, Amsterdam, NL, vol. 575, No. 1-3, Sep. 24, 2004 (Sep. 24, 2004), pp. 1-8, XP004573846, ISSN: 0014-5793. DOI: 10.1016/J.FEBSLET.2004.08.037.
Rana Manish Kumar et al: "Multi-modal Binding of a 'Self' Peptide by HLA-B*27:04 and B*27:05 Allelic Variants, but not B*27:09 or B*27:06 Variants: Fresh Support for Some Theories Explaining Differential Disease Association", Protein Journal, Kluwer Academic/Plenum Publishers, Dordrecht, NL, vol. 35, No. 5, Sep. 7, 2016 (Sep. 7, 2016), pp. 346-353, XP036088952, ISSN: 1572-3887, DOI: 10. 1007/S10930-016-9678-6.
Suzanne L. Topalian et al: "Immune Checkpoint Blockade: A Common Denominator Approach to Cancer Therapy". Cancer Cell. vol. 27, No. 4. Apr. 1, 2015 (Apr. 1, 2015), pp. 450-461, XP055372181. US, ISSN: 1535-6108, DOI: 10.1016/j.ccell.2015.03.001.
Marchesi et al. "HLA-dependent tumour development: a role for tumour associate macrophages?", Journal of Translational Medicine, 2013, vol. 11, No. 247, p. 1-15.
Zipeto et al. "HLA-C and HIV-1: friends or foes?", Retrovirology, 2012, vol. 9, No. 39, p. 1-9.
Baia et al., "Interaction of the LILRB1 inhibitory receptor with HLA class la dimers", Eur. J. Immunology, 2016, vol. 46, p. 1681-1690.
Goodridge et al. "HLA-F and MHC-I Open Conformers Cooperate in a MHC-I Antigen Cross-Presentation Pathway", The Journal of Immunology, 2013, 191: 1567-1577.
Cullen et al. "A Divalent Major Histocompatibility ComplexllgG1 Fusion Protein Induces Antigen-Specific T Cell Activation in Vitro and in Vivo", Cellular Immunology 192, 54-62 (1999).
Zhong et al, "Dimerization of soluble HLA-G by IgG-Fc fragment augments ILT2-mediated inhibition of T-cell alloresponse" Transplantation. Jan. 15, 2009;87(1):8-15.

\* cited by examiner

A

B

A

B

C

A

B

A

B

SEQUENCE LISTING

<160> NUMBER OF SEQ ID NOS: 109

<210> SEQ ID NO 1
<211> LENGTH: 362
<212> TYPE: PRT
<213> ORGANISM: Homo sapiens

<400> SEQUENCE: 1

```
Met Arg Val Thr Ala Pro Arg Thr Val Leu Leu Leu Trp Gly Ala
1               5                   10                  15

Val Ala Leu Thr Glu Thr Trp Ala Gly Ser His Ser Met Arg Tyr Phe
                20                  25                  30

Tyr Thr Ala Met Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
50                  55                  60

Ala Ser Pro Arg Met Ala Pro Arg Ala Pro Trp Ile Glu Gln Glu Gly
65                  70                  75                  80

Pro Glu Tyr Trp Asp Gly Glu Thr Arg Asn Met Lys Ala Ser Ala Gln
                85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Val Met Tyr Gly Cys Asp Val Gly
        115                 120                 125

Pro Asp Gly Arg Leu Leu Arg Gly His Asp Gln Ser Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285
```

```
Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
                340                 345                 350

Ala Gln Gly Ser Asp Val Ser Leu Thr Ala
            355                 360

<210> SEQ ID NO 2
<211> LENGTH: 181
<212> TYPE: PRT
<213> ORGANISM: Homo sapiens

<400> SEQUENCE: 2

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 3
<211> LENGTH: 181
<212> TYPE: PRT
<213> ORGANISM: Homo sapiens

<400> SEQUENCE: 3

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60
```

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
            85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
            165                 170                 175

Thr Leu Gln Arg Ala
            180

<210> SEQ ID NO 4
<211> LENGTH: 181
<212> TYPE: PRT
<213> ORGANISM: Homo sapiens

<400> SEQUENCE: 4

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
            85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
            165                 170                 175

Thr Leu Gln Arg Ala
            180

<210> SEQ ID NO 5
<211> LENGTH: 181
<212> TYPE: PRT
<213> ORGANISM: Homo sapiens

<400> SEQUENCE: 5

Ser His Ser Met Arg Tyr Phe Tyr Thr Ala Met Ser Arg Pro Gly Arg
1               5                   10                  15

```
Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
        180

<210> SEQ ID NO 6
<211> LENGTH: 181
<212> TYPE: PRT
<213> ORGANISM: Homo sapiens

<400> SEQUENCE: 6

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
        180

<210> SEQ ID NO 7
```

```
<211> LENGTH: 273
<212> TYPE: PRT
<213> ORGANISM: Homo sapiens

<400> SEQUENCE: 7

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp

<210> SEQ ID NO 8
<211> LENGTH: 181
<212> TYPE: PRT
<213> ORGANISM: Homo sapiens

<400> SEQUENCE: 8

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60
```

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 9
<211> LENGTH: 181
<212> TYPE: PRT
<213> ORGANISM: Homo sapiens

<400> SEQUENCE: 9

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
        50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 10
<211> LENGTH: 181
<212> TYPE: PRT
<213> ORGANISM: Homo sapiens

<400> SEQUENCE: 10

Ser His Ser Met Arg Tyr Phe Tyr Thr Ala Met Ser Arg Pro Gly Arg
1               5                   10                  15

```
Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 11
<211> LENGTH: 273
<212> TYPE: PRT
<213> ORGANISM: Homo sapiens

<400> SEQUENCE: 11

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Lys Thr His Val Thr His His Pro
            180                 185                 190

Ile Ser Asp His Glu Ala Thr Leu Arg Cys Trp Ala Leu Gly Phe Tyr
    195                 200                 205
```

```
Pro Ala Glu Ile Thr Leu Thr Trp Gln Arg Asp Gly Glu Asp Gln Thr
    210                 215                 220
Gln Asp Thr Glu Leu Val Glu Thr Arg Pro Ala Gly Asp Arg Thr Phe
225                 230                 235                 240
Gln Lys Trp Ala Ala Val Val Pro Ser Gly Glu Glu Gln Arg Tyr
                245                 250                 255
Thr Cys His Val Gln His Glu Gly Leu Pro Lys Pro Leu Thr Leu Arg
                260                 265                 270
Trp
```

```
<210> SEQ ID NO 12
<211> LENGTH: 181
<212> TYPE: PRT
<213> ORGANISM: Homo sapiens

<400> SEQUENCE: 12
```

```
Ser His Ser Met Arg Tyr Phe Tyr Thr Ala Met Ser Arg Pro Gly Arg
1               5                   10                  15
Gly Glu Pro Arg Phe Ile Ala Val Gly Tyr Val Asp Asp Thr Gln Phe
                20                  25                  30
Val Arg Phe Asp Ser Asp Ala Ala Ser Pro Arg Met Ala Pro Arg Ala
            35                  40                  45
Pro Trp Ile Glu Gln Glu Gly Pro Glu Tyr Trp Asp Gly Glu Thr Arg
    50                  55                  60
Asn Met Lys Ala Ser Ala Gln Thr Tyr Arg Glu Asn Leu Arg Ile Ala
65                  70                  75                  80
Leu Arg Tyr Tyr Asn Gln Ser Glu Ala Gly Ser His Ile Ile Gln Val
                85                  90                  95
Met Tyr Gly Cys Asp Val Gly Pro Asp Gly Arg Leu Leu Arg Gly His
            100                 105                 110
Asp Gln Ser Ala Tyr Asp Gly Lys Asp Tyr Ile Ala Leu Asn Glu Asp
        115                 120                 125
Leu Ser Ser Trp Thr Ala Ala Asp Thr Ala Ala Gln Ile Thr Gln Arg
    130                 135                 140
Lys Trp Glu Ala Ala Arg Val Ala Glu Gln Leu Arg Ala Tyr Leu Glu
145                 150                 155                 160
Gly Leu Cys Val Glu Trp Leu Arg Arg Tyr Leu Glu Asn Gly Lys Glu
                165                 170                 175
Thr Leu Gln Arg Ala
            180
```

```
<210> SEQ ID NO 13
<211> LENGTH: 362
<212> TYPE: PRT
<213> ORGANISM: Homo sapiens

<400> SEQUENCE: 13
```

```
Met Arg Val Thr Ala Pro Arg Thr Val Leu Leu Leu Leu Trp Gly Ala
1               5                   10                  15
Val Ala Leu Thr Glu Thr Trp Ala Gly Ser His Ser Met Arg Tyr Phe
                20                  25                  30
Tyr Thr Ala Met Ser Arg Pro Gly Arg Gly Glu Pro Arg Phe Ile Ala
            35                  40                  45
Val Gly Tyr Val Asp Asp Thr Gln Phe Val Arg Phe Asp Ser Asp Ala
    50                  55                  60
```

```
Ala Ser Pro Arg Met Ala Pro Arg Ala Pro Trp Ile Glu Gln Glu Gly
 65                  70                  75                  80

Pro Glu Tyr Trp Asp Gly Glu Thr Arg Asn Met Lys Ala Ser Ala Gln
             85                  90                  95

Thr Tyr Arg Glu Asn Leu Arg Ile Ala Leu Arg Tyr Tyr Asn Gln Ser
        100                 105                 110

Glu Ala Gly Ser His Ile Ile Gln Val Met Tyr Gly Cys Asp Val Gly
    115                 120                 125

Pro Asp Gly Arg Leu Leu Arg Gly His Asp Gln Ser Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 14
<211> LENGTH: 181
<212> TYPE: PRT
<213> ORGANISM: Homo sapiens

<400> SEQUENCE: 14

Ser His Ser Met Arg Tyr Phe Tyr Thr Ala Met Ser Arg Pro Gly Arg
 1               5                  10                  15

Gly Glu Pro Arg Phe Ile Ala Val Gly Tyr Val Asp Asp Thr Gln Phe
             20                  25                  30

Val Arg Phe Asp Ser Asp Ala Ala Ser Pro Arg Met Ala Pro Arg Ala
         35                  40                  45

Pro Trp Ile Glu Gln Glu Gly Pro Glu Tyr Trp Asp Gly Glu Thr Arg
     50                  55                  60

Asn Met Lys Ala Ser Ala Gln Thr Tyr Arg Glu Asn Leu Arg Ile Ala
 65                  70                  75                  80
```

```
Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 15
<211> LENGTH: 181
<212> TYPE: PRT
<213> ORGANISM: Homo sapiens

<400> SEQUENCE: 15

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 16
<211> LENGTH: 181
<212> TYPE: PRT
<213> ORGANISM: Homo sapiens

<400> SEQUENCE: 16

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30
```

-continued

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
 50                  55                  60

Asn Met Lys Ala Ser Ala Gln Thr Tyr Arg Glu Asn Leu Arg Ile Ala
 65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
        180

<210> SEQ ID NO 17
<211> LENGTH: 337
<212> TYPE: PRT
<213> ORGANISM: Homo sapiens

<400> SEQUENCE: 17

Met Arg Val Thr Ala Pro Arg Thr Val Leu Leu Leu Trp Gly Ala
1                5                  10                  15

Val Ala Leu Thr Glu Thr Trp Ala Gly Ser His Ser Met Arg Tyr Phe
                20                  25                  30

Tyr Thr Ala Met Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
 50                  55                  60

Ala Ser Pro Arg Met Ala Pro Arg Ala Pro Trp Ile Glu Gln Glu Gly
 65                  70                  75                  80

Pro Glu Tyr Trp Asp Gly Glu Thr Arg Asn Met Lys Ala Ser Ala Gln
                85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Val Met Tyr Gly Cys Asp Val Gly
        115                 120                 125

Pro Asp Gly Arg Leu Leu Arg Gly His Asp Gln Ser Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr

```
                210                 215                 220
Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser

<210> SEQ ID NO 18
<211> LENGTH: 181
<212> TYPE: PRT
<213> ORGANISM: Homo sapiens

<400> SEQUENCE: 18

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 19
<211> LENGTH: 298
<212> TYPE: PRT
<213> ORGANISM: Homo sapiens

<400> SEQUENCE: 19

Met Arg Val Thr Ala Pro Arg Thr Val Leu Leu Leu Leu Trp Gly Ala
1               5                   10                  15
```

Val Ala Leu Thr Glu Thr Trp Ala Gly Ser His Ser Met Arg Tyr Phe
         20                  25                  30

Tyr Thr Ala Met Ser Arg Pro Gly Arg Gly Glu Pro Arg Phe Ile Ala
         35                  40                  45

Val Gly Tyr Val Asp Asp Thr Gln Phe Val Arg Phe Asp Ser Asp Ala
50                       55                  60

Ala Ser Pro Arg Met Ala Pro Arg Ala Pro Trp Ile Glu Gln Glu Gly
65                  70                  75                  80

Pro Glu Tyr Trp Asp Gly Glu Thr Arg Asn Met Lys Ala Ser Ala Gln
                     85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Val Met Tyr Gly Cys Asp Val Gly
        115                 120                 125

Pro Asp Gly Arg Leu Leu Arg Gly His Asp Gln Ser Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp
    290                 295

<210> SEQ ID NO 20
<211> LENGTH: 181
<212> TYPE: PRT
<213> ORGANISM: Homo sapiens

<400> SEQUENCE: 20

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val

```
                85                  90                  95
Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 21
<211> LENGTH: 273
<212> TYPE: PRT
<213> ORGANISM: Homo sapiens

<400> SEQUENCE: 21

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
            195                 200                 205

Pro Ala Glu Ile Thr Leu Thr Trp Gln Arg Asp Gly Glu Asp Gln Thr
        210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270
```

Trp

<210> SEQ ID NO 22
<211> LENGTH: 181
<212> TYPE: PRT
<213> ORGANISM: Homo sapiens

<400> SEQUENCE: 22

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 23
<211> LENGTH: 362
<212> TYPE: PRT
<213> ORGANISM: Homo sapiens

<400> SEQUENCE: 23

Met Arg Val Thr Ala Pro Arg Thr Val Leu Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ala Met Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Pro Arg Met Ala Pro Arg Ala Pro Trp Ile Glu Gln Glu Gly
65                  70                  75                  80

Pro Glu Tyr Trp Asp Gly Glu Thr Arg Asn Met Lys Ala Ser Ala Gln
                85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Val Met Tyr Gly Cys Asp Val Gly
        115                 120                 125

Pro Asp Gly Arg Leu Leu Arg Gly His Asn Gln Tyr Ala Tyr Asp Gly

```
                130                 135                 140
Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Arg Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
                195                 200                 205

Pro Lys Thr His Val Thr His His Pro Ile Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 24
<211> LENGTH: 181
<212> TYPE: PRT
<213> ORGANISM: Homo sapiens

<400> SEQUENCE: 24

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
        50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140
```

```
Lys Trp Glu Ala Ala Arg Val Ala Glu Gln Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 25
<211> LENGTH: 362
<212> TYPE: PRT
<213> ORGANISM: Homo sapiens

<400> SEQUENCE: 25

Met Arg Val Thr Ala Pro Arg Thr Val Leu Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ala Met Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
50                  55                  60

Ala Ser Pro Arg Met Ala Pro Arg Ala Pro Trp Ile Glu Gln Glu Gly
65                  70                  75                  80

Pro Glu Tyr Trp Asp Gly Glu Thr Arg Asn Met Lys Ala Ser Ala Gln
                85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Val Met Tyr Gly Cys Asp Val Gly
        115                 120                 125

Pro Asp Gly Arg Leu Leu Arg Gly His Asn Gln Tyr Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335
```

```
Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 26
<211> LENGTH: 273
<212> TYPE: PRT
<213> ORGANISM: Homo sapiens

<400> SEQUENCE: 26

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp

<210> SEQ ID NO 27
<211> LENGTH: 273
<212> TYPE: PRT
<213> ORGANISM: Homo sapiens

<400> SEQUENCE: 27

Ser His Ser Met Arg Tyr Phe Tyr Thr Ala Met Ser Arg Pro Gly Arg
1               5                   10                  15
```

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly Tyr
            100                 105                 110

Asp Gln Asp Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Arg Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp

<210> SEQ ID NO 28
<211> LENGTH: 181
<212> TYPE: PRT
<213> ORGANISM: Homo sapiens

<400> SEQUENCE: 28

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly Tyr
            100                 105                 110

```
Asp Gln Asp Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Arg Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 29
<211> LENGTH: 362
<212> TYPE: PRT
<213> ORGANISM: Homo sapiens

<400> SEQUENCE: 29

Met Arg Val Thr Ala Pro Arg Thr Val Leu Leu Leu Trp Gly Ala
1                5                  10                  15

Val Ala Leu Thr Glu Thr Trp Ala Gly Ser His Ser Met Arg Tyr Phe
                20                  25                  30

Tyr Thr Ala Met Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
    50                  55                  60

Ala Ser Pro Arg Met Ala Pro Arg Ala Pro Trp Ile Glu Gln Glu Gly
65                  70                  75                  80

Pro Glu Tyr Trp Asp Gly Glu Thr Arg Asn Met Lys Ala Ser Ala Gln
                85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Arg Met Tyr Gly Cys Asp Leu Gly
        115                 120                 125

Pro Asp Gly Arg Leu Leu Arg Gly Tyr Asn Gln Tyr Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Arg Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300
```

```
Thr Val Pro Ile Val Gly Ile Val Ala Gly Leu Ala Val Leu Ala Val
305                 310                 315                 320

Val Val Ile Gly Ala Val Ala Ala Val Met Cys Arg Arg Lys Ser
            325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 30
<211> LENGTH: 362
<212> TYPE: PRT
<213> ORGANISM: Homo sapiens

<400> SEQUENCE: 30

Met Arg Val Thr Ala Pro Arg Thr Val Leu Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ala Met Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
50                  55                  60

Ala Ser Pro Arg Met Ala Pro Arg Ala Pro Trp Ile Glu Gln Glu Gly
65                  70                  75                  80

Pro Glu Tyr Trp Asp Gly Glu Thr Arg Asn Met Lys Ala Ser Ala Gln
                85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Val Met Tyr Gly Cys Asp Val Gly
            115                 120                 125

Pro Asp Gly Arg Leu Leu Arg Gly His Asp Gln Ser Ala Tyr Asp Gly
            130                 135                 140

Lys Asp Tyr Ile Ala Leu Asn Glu Asp Leu Ser Ser Trp Thr Ala Ala
145                 150                 155                 160

Asp Thr Ala Ala Gln Ile Ile Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
            195                 200                 205

Pro Lys Thr His Val Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
```

```
                305                 310                 315                 320
Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
                340                 345                 350

Ala Gln Gly Ser Asp Val Ser Leu Thr Ala
                355                 360

<210> SEQ ID NO 31
<211> LENGTH: 181
<212> TYPE: PRT
<213> ORGANISM: Homo sapiens

<400> SEQUENCE: 31

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
        50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asn Gln Tyr Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Ser Leu Arg Arg Tyr Leu Glu Asn Gly Lys Glu
                165                 170                 175

Thr Leu Gln Arg Ala
            180

<210> SEQ ID NO 32
<211> LENGTH: 181
<212> TYPE: PRT
<213> ORGANISM: Homo sapiens

<400> SEQUENCE: 32

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
        50                  55                  60

Asn Met Lys Ala Ser Ala Gln Thr Tyr Arg Glu Asn Leu Arg Ile Ala
65                  70                  75                  80

Leu Pro Tyr Tyr Asn Gln Ser Glu Ala Gly Ser His Ile Ile Gln Val
```

```
            85                  90                  95
Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 33
<211> LENGTH: 181
<212> TYPE: PRT
<213> ORGANISM: Homo sapiens

<400> SEQUENCE: 33

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Glu Ala Glu Gln Asp Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 34
<211> LENGTH: 181
<212> TYPE: PRT
<213> ORGANISM: Homo sapiens

<400> SEQUENCE: 34

Ser His Ser Met Arg Tyr Phe Tyr Thr Ser Val Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
```

```
                    35                  40                  45
Pro Trp Ile Glu Gln Glu Gly Pro Glu Tyr Trp Asp Gly Glu Thr Arg
 50                      55                  60

Asn Met Lys Ala Ser Ala Gln Thr Tyr Arg Glu Asn Leu Arg Ile Ala
 65                  70                  75                  80

Leu Arg Tyr Tyr Asn Gln Ser Glu Ala Gly Ser His Ile Ile Gln Val
                 85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 35
<211> LENGTH: 362
<212> TYPE: PRT
<213> ORGANISM: Homo sapiens

<400> SEQUENCE: 35

Met Arg Val Thr Ala Pro Arg Thr Val Leu Leu Leu Leu Trp Gly Ala
 1               5                  10                  15

Val Ala Leu Thr Glu Thr Trp Ala Gly Ser His Ser Met Arg Tyr Phe
                20                  25                  30

Tyr Thr Ala Met Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
 50                  55                  60

Ala Ser Pro Arg Met Ala Pro Arg Ala Pro Trp Ile Glu Gln Glu Gly
 65                  70                  75                  80

Pro Glu Tyr Trp Asp Gly Glu Thr Arg Asn Met Lys Ala Ser Ala Gln
                 85                  90                  95

Thr Tyr Arg Glu Asn Leu Arg Ile Ala Leu Arg Tyr Tyr Asn Gln Ser
            100                 105                 110

Glu Ala Gly Ser His Thr Leu Gln Trp Met Tyr Gly Cys Asp Val Gly
        115                 120                 125

Pro Asp Gly Arg Leu Leu Arg Gly His Asp Gln Ser Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
210                 215                 220
```

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
        290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360

<210> SEQ ID NO 36
<211> LENGTH: 181
<212> TYPE: PRT
<213> ORGANISM: Homo sapiens

<400> SEQUENCE: 36

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Ser Leu Arg Asn Leu
65                  70                  75                  80

Arg Gly Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
        180

<210> SEQ ID NO 37
<211> LENGTH: 181
<212> TYPE: PRT
<213> ORGANISM: Homo sapiens

<400> SEQUENCE: 37

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
130                 135                 140

Lys Trp Glu Ala Ala Arg Glu Ala Glu Gln Arg Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 38
<211> LENGTH: 181
<212> TYPE: PRT
<213> ORGANISM: Homo sapiens

<400> SEQUENCE: 38

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg His Leu Glu Asn Gly Lys Glu
                165                 170                 175

Thr Leu Gln Arg Ala
            180

<210> SEQ ID NO 39
<211> LENGTH: 181
<212> TYPE: PRT
<213> ORGANISM: Homo sapiens

<400> SEQUENCE: 39

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg His Leu Glu Asn Gly Lys Glu
                165                 170                 175

Thr Leu Gln Arg Ala
            180

<210> SEQ ID NO 40
<211> LENGTH: 181
<212> TYPE: PRT
<213> ORGANISM: Homo sapiens

<400> SEQUENCE: 40

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Val Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

```
Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 41
<211> LENGTH: 181
<212> TYPE: PRT
<213> ORGANISM: Homo sapiens

<400> SEQUENCE: 41

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Glu Pro Arg Ala
            35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 42
<211> LENGTH: 181
<212> TYPE: PRT
<213> ORGANISM: Homo sapiens

<400> SEQUENCE: 42

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95
```

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Asp Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 43
<211> LENGTH: 181
<212> TYPE: PRT
<213> ORGANISM: Homo sapiens

<400> SEQUENCE: 43

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Tyr Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 44
<211> LENGTH: 181
<212> TYPE: PRT
<213> ORGANISM: Homo sapiens

<400> SEQUENCE: 44

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

```
Pro Trp Ile Glu Gln Glu Gly Pro Glu Tyr Trp Asp Gly Glu Thr Arg
 50                  55                  60

Asn Met Lys Ala Ser Ala Gln Thr Tyr Arg Glu Asn Leu Arg Ile Ala
 65                  70                  75                  80

Leu Arg Tyr Tyr Asn Gln Ser Glu Ala Gly Ser His Ile Ile Gln Val
                 85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
                115                 120                 125

Leu Ser Ser Trp Thr Ala Ala Asp Thr Ala Ala Gln Ile Thr Gln Arg
                130                 135                 140

Lys Trp Glu Ala Ala Arg Val Ala Glu Gln Arg Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 45
<211> LENGTH: 181
<212> TYPE: PRT
<213> ORGANISM: Homo sapiens

<400> SEQUENCE: 45

Ser His Ser Met Arg Tyr Phe Tyr Thr Ala Met Ser Arg Pro Gly Arg
 1               5                  10                  15

Gly Glu Pro Arg Phe Ile Ala Val Gly Tyr Val Asp Asp Thr Gln Phe
                 20                  25                  30

Val Arg Phe Asp Ser Asp Ala Ala Ser Pro Arg Met Ala Pro Arg Ala
                 35                  40                  45

Pro Trp Ile Glu Gln Glu Gly Pro Glu Tyr Trp Asp Gly Lys Thr Arg
 50                  55                  60

Asn Met Lys Ala Ser Ala Gln Thr Tyr Arg Glu Asn Leu Arg Ile Ala
 65                  70                  75                  80

Leu Arg Tyr Tyr Asn Gln Ser Glu Ala Gly Ser His Ile Ile Gln Val
                 85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
                115                 120                 125

Leu Ser Ser Trp Thr Ala Ala Asp Thr Ala Ala Gln Ile Thr Gln Arg
                130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 46
<211> LENGTH: 181
<212> TYPE: PRT
<213> ORGANISM: Homo sapiens

<400> SEQUENCE: 46
```

```
Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Val Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 47
<211> LENGTH: 181
<212> TYPE: PRT
<213> ORGANISM: Homo sapiens

<400> SEQUENCE: 47

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Glu Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
```

180

<210> SEQ ID NO 48
<211> LENGTH: 181
<212> TYPE: PRT
<213> ORGANISM: Homo sapiens

<400> SEQUENCE: 48

Ser His Ser Met Arg Tyr Phe Tyr Thr Ala Met Ser Arg Pro Gly Arg
1               5                   10                  15

Gly Glu Ser Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 49
<211> LENGTH: 181
<212> TYPE: PRT
<213> ORGANISM: Homo sapiens

<400> SEQUENCE: 49

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg

```
            130                 135                 140
Lys Trp Glu Ala Ala Arg Val Ala Glu Gln Asp Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 50
<211> LENGTH: 181
<212> TYPE: PRT
<213> ORGANISM: Homo sapiens

<400> SEQUENCE: 50

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Glu Cys Val Glu Trp Leu Arg Arg Tyr Leu Glu Asn Gly Lys Glu
                165                 170                 175

Thr Leu Gln Arg Ala
            180

<210> SEQ ID NO 51
<211> LENGTH: 181
<212> TYPE: PRT
<213> ORGANISM: Homo sapiens

<400> SEQUENCE: 51

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
```

```
                    85                  90                  95
Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Thr Cys Val Glu Trp Leu Arg Arg Tyr Leu Glu Asn Gly Lys Glu
                165                 170                 175

Thr Leu Gln Arg Ala
            180

<210> SEQ ID NO 52
<211> LENGTH: 181
<212> TYPE: PRT
<213> ORGANISM: Homo sapiens

<400> SEQUENCE: 52

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu His Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 53
<211> LENGTH: 115
<212> TYPE: PRT
<213> ORGANISM: Homo sapiens
<220> FEATURE:
<221> NAME/KEY: misc_feature
<222> LOCATION: (115)..(115)
<223> OTHER INFORMATION: Xaa can be any naturally occurring amino acid

<400> SEQUENCE: 53

Ser His Ser Met Arg Tyr Phe Tyr Thr Ala Met Ser Arg Pro Gly Arg
1               5                   10                  15
```

-continued

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
        50                  55                  60

Asn Met Lys Ala Ser Ala Gln Thr Tyr Arg Glu Asn Leu Arg Ile Ala
 65                 70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Xaa
        115

<210> SEQ ID NO 54
<211> LENGTH: 362
<212> TYPE: PRT
<213> ORGANISM: Homo sapiens

<400> SEQUENCE: 54

Met Arg Val Thr Ala Pro Arg Thr Val Leu Leu Leu Leu Trp Gly Ala
 1               5                  10                  15

Val Ala Leu Thr Glu Thr Trp Ala Gly Ser His Ser Met Arg Tyr Phe
                20                  25                  30

Tyr Thr Ala Met Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
        50                  55                  60

Ala Ser Pro Arg Met Ala Pro Arg Ala Pro Trp Ile Glu Gln Glu Gly
 65                 70                  75                  80

Pro Glu Tyr Trp Asp Gly Glu Thr Arg Asn Met Lys Ala Ser Ala Gln
                85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Val Met Tyr Gly Cys Asp Val Gly
        115                 120                 125

Pro Asp Gly Arg Leu Leu Arg Gly His Asp Gln Ser Ala Tyr Asp Gly
        130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
        210                 215                 220

Leu Arg Cys Trp Ala Leu Gly Phe Tyr Pro Val Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
        290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
            325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 55
<211> LENGTH: 181
<212> TYPE: PRT
<213> ORGANISM: Homo sapiens

<400> SEQUENCE: 55

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Ala Ala Glu Gln Arg Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 56
<211> LENGTH: 181
<212> TYPE: PRT
<213> ORGANISM: Homo sapiens

<400> SEQUENCE: 56

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

```
Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
                115                 120                 125

Leu Arg Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 57
<211> LENGTH: 181
<212> TYPE: PRT
<213> ORGANISM: Homo sapiens

<400> SEQUENCE: 57

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly Tyr
                100                 105                 110

His Gln Asp Ala Tyr Asp Gly Lys Asp Tyr Ile Ala Leu Asn Glu Asp
                115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 58
<211> LENGTH: 108
<212> TYPE: PRT
<213> ORGANISM: Homo sapiens

<400> SEQUENCE: 58
```

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Glu Arg Leu
            100                 105

<210> SEQ ID NO 59
<211> LENGTH: 73
<212> TYPE: PRT
<213> ORGANISM: Homo sapiens

<400> SEQUENCE: 59

Leu Arg Gly His Asp Gln Ser Ala Tyr Asp Gly Lys Asp Tyr Ile Ala
1               5                   10                  15

Leu Asn Glu Asp Leu Ser Ser Trp Thr Ala Ala Asp Thr Ala Ala Gln
            20                  25                  30

Ile Thr Gln Arg Lys Trp Glu Ala Ala Arg Val Ala Glu Gln Leu Arg
        35                  40                  45

Ala Tyr Leu Glu Gly Leu Cys Val Glu Trp Leu Arg Arg Tyr Leu Glu
50                  55                  60

Asn Gly Lys Glu Thr Leu Gln Arg Ala
65                  70

<210> SEQ ID NO 60
<211> LENGTH: 181
<212> TYPE: PRT
<213> ORGANISM: Homo sapiens

<400> SEQUENCE: 60

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Arg Arg Met Ala Pro Arg Ala
        35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
            165                 170                 175

Thr Leu Gln Arg Ala
            180

<210> SEQ ID NO 61
<211> LENGTH: 181
<212> TYPE: PRT
<213> ORGANISM: Homo sapiens

<400> SEQUENCE: 61

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Lys Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
            165                 170                 175

Thr Leu Gln Arg Ala
            180

<210> SEQ ID NO 62
<211> LENGTH: 181
<212> TYPE: PRT
<213> ORGANISM: Homo sapiens

<400> SEQUENCE: 62

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

His Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

```
Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 63
<211> LENGTH: 273
<212> TYPE: PRT
<213> ORGANISM: Homo sapiens

<400> SEQUENCE: 63

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Pro Ser Gly Glu Glu Gln Arg Tyr
                245                 250                 255

Thr Cys His Val Gln His Glu Gly Leu Pro Lys His Leu Thr Leu Arg
            260                 265                 270

Trp
```

<210> SEQ ID NO 64
<211> LENGTH: 181
<212> TYPE: PRT
<213> ORGANISM: Homo sapiens

<400> SEQUENCE: 64

```
Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Thr Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180
```

<210> SEQ ID NO 65
<211> LENGTH: 181
<212> TYPE: PRT
<213> ORGANISM: Homo sapiens

<400> SEQUENCE: 65

```
Ser His Ser Met Arg Tyr Phe His Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140
```

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
            165                 170                 175

Thr Leu Gln Arg Ala
        180

<210> SEQ ID NO 66
<211> LENGTH: 181
<212> TYPE: PRT
<213> ORGANISM: Homo sapiens

<400> SEQUENCE: 66

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Asn Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
            165                 170                 175

Thr Leu Gln Arg Ala
        180

<210> SEQ ID NO 67
<211> LENGTH: 181
<212> TYPE: PRT
<213> ORGANISM: Homo sapiens

<400> SEQUENCE: 67

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly Tyr
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 68
<211> LENGTH: 181
<212> TYPE: PRT
<213> ORGANISM: Homo sapiens

<400> SEQUENCE: 68

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Glu Ala Arg Val Ala Glu Gln Arg Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 69
<211> LENGTH: 181
<212> TYPE: PRT
<213> ORGANISM: Homo sapiens

<400> SEQUENCE: 69

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

```
Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
                115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Pro Cys Val Glu Trp Leu Arg Arg Tyr Leu Glu Asn Gly Lys Glu
                165                 170                 175

Thr Leu Gln Arg Ala
            180
```

<210> SEQ ID NO 70
<211> LENGTH: 181
<212> TYPE: PRT
<213> ORGANISM: Homo sapiens

<400> SEQUENCE: 70

```
Ser His Ser Met Arg Tyr Phe Tyr Thr Ala Met Ser Arg Pro Gly Leu
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
                115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180
```

<210> SEQ ID NO 71
<211> LENGTH: 181
<212> TYPE: PRT
<213> ORGANISM: Homo sapiens

<400> SEQUENCE: 71

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Thr Ser Pro Arg Lys Glu Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 72
<211> LENGTH: 181
<212> TYPE: PRT
<213> ORGANISM: Homo sapiens

<400> SEQUENCE: 72

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asn Gln Tyr Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
    130                 135                 140

Lys Trp Glu Ala Ala Cys Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala

180

<210> SEQ ID NO 73
<211> LENGTH: 181
<212> TYPE: PRT
<213> ORGANISM: Homo sapiens

<400> SEQUENCE: 73

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Cys Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 74
<211> LENGTH: 273
<212> TYPE: PRT
<213> ORGANISM: Homo sapiens

<400> SEQUENCE: 74

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Pro Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg

```
              130                 135                 140
Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
                195                 200                 205

Pro Ala Glu Ile Thr Leu Thr Trp Gln Arg Asp Gly Glu Asp Gln Thr
210                 215                 220

Gln Asp Thr Glu Leu Val Glu Thr Arg Pro Ala Gly Asp Arg Thr Phe
225                 230                 235                 240

Gln Lys Trp Ala Ala Val Val Val Pro Ser Gly Glu Glu Gln Arg Tyr
                245                 250                 255

Thr Cys His Val Gln His Glu Gly Leu Pro Lys Pro Leu Thr Leu Arg
                260                 265                 270

Trp

<210> SEQ ID NO 75
<211> LENGTH: 181
<212> TYPE: PRT
<213> ORGANISM: Homo sapiens

<400> SEQUENCE: 75

Ser His Ser Met Arg Tyr Phe Asp Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 76
<211> LENGTH: 181
<212> TYPE: PRT
<213> ORGANISM: Homo sapiens

<400> SEQUENCE: 76
```

```
Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Gly
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 77
<211> LENGTH: 181
<212> TYPE: PRT
<213> ORGANISM: Homo sapiens

<400> SEQUENCE: 77

Ser His Ser Met Arg Tyr Phe His Thr Ala Met Ser Arg Pro Gly Arg
1               5                   10                  15

Gly Glu Pro Arg Phe Ile Thr Val Gly Tyr Val Asp Asp Thr Leu Phe
            20                  25                  30

Val Arg Phe Asp Ser Asp Ala Thr Ser Pro Arg Lys Glu Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
```

180

<210> SEQ ID NO 78
<211> LENGTH: 181
<212> TYPE: PRT
<213> ORGANISM: Homo sapiens

<400> SEQUENCE: 78

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65              70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Ser Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 79
<211> LENGTH: 181
<212> TYPE: PRT
<213> ORGANISM: Homo sapiens

<400> SEQUENCE: 79

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65              70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Thr Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg

```
            130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 80
<211> LENGTH: 181
<212> TYPE: PRT
<213> ORGANISM: Homo sapiens

<400> SEQUENCE: 80

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
        50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Lys Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 81
<211> LENGTH: 273
<212> TYPE: PRT
<213> ORGANISM: Homo sapiens

<400> SEQUENCE: 81

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
        50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
```

```
                    85                  90                  95
Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
    210                 215                 220

Gln Asp Thr Lys Leu Val Glu Thr Arg Pro Ala Gly Asp Arg Thr Phe
225                 230                 235                 240

Gln Lys Trp Ala Ala Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp

<210> SEQ ID NO 82
<211> LENGTH: 181
<212> TYPE: PRT
<213> ORGANISM: Homo sapiens

<400> SEQUENCE: 82

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala His Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
```

180

<210> SEQ ID NO 83
<211> LENGTH: 273
<212> TYPE: PRT
<213> ORGANISM: Homo sapiens

<400> SEQUENCE: 83

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Ser Ser Trp Thr Ala Ala Asp Thr Ala Gln Ile Thr Gln Arg
130                 135                 140

Lys Trp Glu Ala Ala Arg Glu Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
    210                 215                 220

Gln Asp Thr Glu Leu Val Glu Thr Arg Pro Ala Gly Asp Arg Thr Phe
225                 230                 235                 240

Gln Lys Trp Ala Ala Val Val Pro Ser Gly Glu Glu Gln Arg Tyr
                245                 250                 255

Thr Cys His Val Gln His Glu Gly Leu Pro Lys Pro Leu Thr Leu Arg
            260                 265                 270

Trp

<210> SEQ ID NO 84
<211> LENGTH: 181
<212> TYPE: PRT
<213> ORGANISM: Homo sapiens

<400> SEQUENCE: 84

Ser His Ser Met Arg Tyr Phe Tyr Thr Ala Met Ser Arg Pro Gly Arg
1               5                   10                  15

Gly Glu Pro Arg Phe Ile Ser Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

```
Pro Trp Ile Glu Gln Glu Gly Pro Glu Tyr Trp Asp Gly Glu Thr Arg
 50                  55                  60

Asn Met Lys Ala Ser Ala Gln Thr Tyr Arg Glu Asn Leu Arg Ile Ala
 65                  70                  75                  80

Leu Arg Tyr Tyr Asn Gln Ser Glu Ala Gly Ser His Ile Ile Gln Val
                 85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 85
<211> LENGTH: 273
<212> TYPE: PRT
<213> ORGANISM: Homo sapiens

<400> SEQUENCE: 85

Ser His Ser Met Arg Tyr Phe Tyr Thr Ala Met Ser Arg Pro Gly Arg
  1               5                  10                  15

Gly Glu Pro Arg Phe Ile Ala Val Gly Tyr Val Asp Asp Thr Gln Phe
             20                  25                  30

Val Arg Phe Asp Ser Asp Ala Ala Ser Pro Arg Met Ala Pro Arg Ala
         35                  40                  45

Pro Trp Ile Glu Gln Glu Gly Pro Glu Tyr Trp Asp Gly Glu Thr Arg
 50                  55                  60

Asn Met Lys Ala Ser Ala Gln Thr Tyr Arg Glu Asn Leu Arg Ile Ala
 65                  70                  75                  80

Leu Arg Tyr Tyr Asn Gln Ser Glu Ala Gly Ser His Ile Ile Gln Val
                 85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Ser Gln Arg
130                 135                 140

Lys Leu Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala Asp Pro Pro Lys Thr His Val Thr His His Pro
            180                 185                 190

Ile Ser Asp His Glu Ala Thr Leu Arg Cys Trp Ala Leu Gly Phe Tyr
            195                 200                 205

Pro Ala Glu Ile Thr Leu Thr Trp Gln Arg Asp Gly Glu Asp Gln Thr
210                 215                 220

Gln Asp Thr Glu Leu Val Glu Thr Arg Pro Ala Gly Asp Arg Thr Phe
```

```
                    225                 230                 235                 240
Gln Lys Trp Ala Ala Val Val Pro Ser Gly Glu Glu Gln Arg Tyr
                245                 250                 255
Thr Cys His Val Gln His Glu Gly Leu Pro Lys Pro Leu Thr Leu Arg
                260                 265                 270

Trp

<210> SEQ ID NO 86
<211> LENGTH: 181
<212> TYPE: PRT
<213> ORGANISM: Homo sapiens

<400> SEQUENCE: 86

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Ser Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 87
<211> LENGTH: 181
<212> TYPE: PRT
<213> ORGANISM: Homo sapiens

<400> SEQUENCE: 87

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95
```

```
Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Gly
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 88
<211> LENGTH: 181
<212> TYPE: PRT
<213> ORGANISM: Homo sapiens

<400> SEQUENCE: 88

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Lys Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
            130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 89
<211> LENGTH: 181
<212> TYPE: PRT
<213> ORGANISM: Homo sapiens

<400> SEQUENCE: 89

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
            35                  40                  45
```

-continued

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
            115                 120                 125

Leu Ser Ser Trp Thr Ala Asp Thr Ala Ala Gln Ile Thr Gln Arg
    130                 135                 140

Lys Trp Glu Ala Ala Arg Glu Ala Glu Gln Arg Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
        180

<210> SEQ ID NO 90
<211> LENGTH: 181
<212> TYPE: PRT
<213> ORGANISM: Homo sapiens

<400> SEQUENCE: 90

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Asp Thr Ala Ala Gln Ile Thr Gln Arg
    130                 135                 140

Lys Trp Glu Ala Ala Cys Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
        180

<210> SEQ ID NO 91
<211> LENGTH: 181
<212> TYPE: PRT
<213> ORGANISM: Homo sapiens

<400> SEQUENCE: 91

```
Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
130                 135                 140

Lys Trp Glu Ala Val Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 92
<211> LENGTH: 181
<212> TYPE: PRT
<213> ORGANISM: Homo sapiens

<400> SEQUENCE: 92

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asn Gln Tyr Ala Tyr Asp Gly Lys Asp Tyr Ile Ala Leu Asn Glu Asp
            115                 120                 125

Leu Ser Ser Arg Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
```

180

<210> SEQ ID NO 93
<211> LENGTH: 181
<212> TYPE: PRT
<213> ORGANISM: Homo sapiens

<400> SEQUENCE: 93

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Leu Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 94
<211> LENGTH: 181
<212> TYPE: PRT
<213> ORGANISM: Homo sapiens

<400> SEQUENCE: 94

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Leu Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg

```
                130                 135                 140
Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 95
<211> LENGTH: 181
<212> TYPE: PRT
<213> ORGANISM: Homo sapiens

<400> SEQUENCE: 95

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
        50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Lys Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 96
<211> LENGTH: 181
<212> TYPE: PRT
<213> ORGANISM: Homo sapiens

<400> SEQUENCE: 96

Ser His Ser Met Arg Tyr Phe Tyr Thr Ala Met Ser Arg Pro Gly Arg
1               5                   10                  15

Gly Glu Pro Arg Phe Ile Thr Val Gly Tyr Val Asp Asp Thr Leu Phe
                20                  25                  30

Val Arg Phe Asp Ser Asp Ala Thr Ser Pro Arg Lys Glu Pro Arg Ala
            35                  40                  45

Pro Trp Ile Glu Gln Glu Gly Pro Glu Tyr Trp Asp Gly Glu Thr Arg
        50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
```

```
                85                  90                  95
Met Tyr Gly Cys Asp Val Gly Pro Asp Gly Arg Leu Leu Arg Gly His
                100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
        180

<210> SEQ ID NO 97
<211> LENGTH: 181
<212> TYPE: PRT
<213> ORGANISM: Homo sapiens

<400> SEQUENCE: 97

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
                100                 105                 110

Asn Gln Tyr Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Cys Leu Arg Arg Tyr Leu Glu Asn Gly Lys Glu
                165                 170                 175

Thr Leu Gln Arg Ala
        180

<210> SEQ ID NO 98
<211> LENGTH: 273
<212> TYPE: PRT
<213> ORGANISM: Homo sapiens

<400> SEQUENCE: 98

Ser His Ser Met Arg Tyr Phe Tyr Thr Ala Met Ser Arg Pro Gly Arg
1               5                   10                  15

Gly Glu Pro Arg Phe Ile Thr Val Gly Tyr Val Asp Asp Thr Gln Phe
            20                  25                  30

Val Arg Phe Asp Ser Asp Ala Thr Ser Pro Arg Met Ala Pro Arg Ala
```

```
            35                  40                  45
Pro Trp Ile Glu Gln Glu Gly Pro Glu Tyr Trp Asp Gly Glu Thr Arg
 50                  55                  60
Asn Met Lys Ala Ser Ala Gln Thr Tyr Arg Glu Asn Leu Arg Ile Ala
 65                  70                  75                  80
Leu Arg Tyr Tyr Asn Gln Ser Glu Ala Gly Ser His Ile Ile Gln Val
                     85                  90                  95
Met Tyr Gly Cys Asp Val Gly Pro Asp Gly Arg Leu Leu Arg Gly His
                    100                 105                 110
Asp Gln Ser Ala Tyr Asp Gly Lys Asp Tyr Ile Ala Leu Asn Glu Asp
                    115                 120                 125
Leu Ser Ser Trp Thr Ala Ala Asp Thr Ala Ala Gln Ile Thr Gln Arg
                130                 135                 140
Lys Trp Glu Ala Ala Arg Val Ala Glu Gln Leu Arg Ala Tyr Leu Glu
145                 150                 155                 160
Gly Leu Cys Val Glu Trp Leu Arg Arg Tyr Leu Glu Asn Gly Lys Glu
                    165                 170                 175
Thr Leu Gln Arg Ala Asp Pro Pro Lys Thr His Val Thr His His Pro
                    180                 185                 190
Ile Ser Asp His Glu Ala Thr Leu Arg Cys Trp Ala Leu Gly Phe Tyr
                    195                 200                 205
Pro Ala Glu Ile Thr Leu Thr Trp Gln Arg Asp Gly Glu Asp Gln Thr
                210                 215                 220
Gln Asp Thr Glu Leu Val Glu Thr Arg Pro Ala Gly Asp Arg Thr Phe
225                 230                 235                 240
Gln Lys Trp Ala Ala Val Val Val Pro Ser Gly Glu Glu Gln Arg Tyr
                    245                 250                 255
Thr Cys His Val Gln His Glu Gly Leu Pro Lys Pro Leu Thr Leu Arg
                    260                 265                 270
Trp
```

<210> SEQ ID NO 99  
<211> LENGTH: 181  
<212> TYPE: PRT  
<213> ORGANISM: Homo sapiens

<400> SEQUENCE: 99

```
Ser His Ser Met Arg Tyr Phe Tyr Thr Ala Met Ser Arg Pro Gly Arg
 1                   5                  10                  15
Gly Glu Pro Arg Phe Ile Ala Val Gly Tyr Val Asp Asp Thr Gln Phe
                    20                  25                  30
Val Arg Phe Asp Ser Asp Ala Ala Ser Pro Arg Met Ala Pro Arg Ala
                    35                  40                  45
Pro Trp Ile Glu Gln Glu Gly Pro Glu Tyr Trp Asp Gly Glu Thr Arg
 50                  55                  60
Asn Met Lys Ala Ser Ala Gln Thr Tyr Arg Glu Asn Leu Arg Ile Ala
 65                  70                  75                  80
Leu Arg Tyr Tyr Asn Gln Ser Glu Ala Gly Ser His Ile Ile Gln Val
                     85                  90                  95
Met Tyr Gly Cys Asp Val Gly Pro Asp Gly Arg Leu Leu Arg Gly His
                    100                 105                 110
Asp Gln Ser Ala Tyr Asp Gly Lys Asp Tyr Ile Ala Leu Asn Glu Asp
                    115                 120                 125
Leu Ser Ser Trp Thr Ala Ala Asp Thr Ala Ala Gln Ile Thr Gln Arg
```

```
        130                 135                 140
Lys Trp Glu Ala Ala Arg Val Ala Asp Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 100
<211> LENGTH: 181
<212> TYPE: PRT
<213> ORGANISM: Homo sapiens

<400> SEQUENCE: 100

Ser His Ser Met Arg Tyr Phe His Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 101
<211> LENGTH: 181
<212> TYPE: PRT
<213> ORGANISM: Homo sapiens

<400> SEQUENCE: 101

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
                20                  25                  30

Val Arg Phe Asp Ser Asp Ala Ala Ser Pro Arg Met Ala Pro Arg Ala
            35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser Tyr Ile Ile Gln Val
```

```
            85                  90                  95
Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 102
<211> LENGTH: 181
<212> TYPE: PRT
<213> ORGANISM: Homo sapiens

<400> SEQUENCE: 102

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Thr Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
            115                 120                 125

Leu Ser Ser Trp Thr Ala Ala Asp Thr Ala Ala Gln Ile Thr Gln Arg
        130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 103
<211> LENGTH: 181
<212> TYPE: PRT
<213> ORGANISM: Homo sapiens

<400> SEQUENCE: 103

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
```

```
                35                  40                  45
Pro Trp Ile Glu Gln Glu Gly Pro Glu Tyr Trp Asp Gly Glu Thr Arg
 50                  55                  60
Asn Met Lys Ala Ser Ala Gln Thr Tyr Arg Glu Asn Leu Arg Ile Ala
 65                  70                  75                  80
Leu Arg Tyr Tyr Asn Gln Ser Glu Ala Gly Ser His Ile Ile Gln Val
                 85                  90                  95
Met Tyr Gly Cys Asp Val Gly Pro Asp Gly Arg Leu Leu Arg Gly His
                100                 105                 110
Asp Gln Phe Ala Tyr Asp Gly Lys Asp Tyr Ile Ala Leu Asn Glu Asp
            115                 120                 125
Leu Ser Ser Trp Thr Ala Ala Asp Thr Ala Ala Gln Ile Thr Gln Arg
        130                 135                 140
Lys Trp Glu Ala Ala Arg Val Ala Glu Gln Leu Arg Ala Tyr Leu Glu
145                 150                 155                 160
Gly Leu Cys Val Glu Trp Leu Arg Arg Tyr Leu Glu Asn Gly Lys Glu
                165                 170                 175
Thr Leu Gln Arg Ala
            180

<210> SEQ ID NO 104
<211> LENGTH: 181
<212> TYPE: PRT
<213> ORGANISM: Homo sapiens

<400> SEQUENCE: 104

Ser His Ser Met Arg Tyr Phe Tyr Thr Ala Met Ser Arg Pro Gly Arg
 1                5                  10                  15
Gly Glu Pro Arg Phe Ile Ala Val Gly Tyr Val Asp Asp Thr Gln Phe
                 20                  25                  30
Val Arg Phe Asp Ser Asp Ala Ala Ser Pro Arg Met Ala Pro Arg Ala
             35                  40                  45
Pro Trp Ile Glu Gln Glu Gly Pro Glu Tyr Trp Asp Gly Glu Thr Arg
 50                  55                  60
Asn Met Lys Ala Ser Ala Gln Thr Tyr Arg Glu Asn Leu Arg Ile Ala
 65                  70                  75                  80
Leu Arg Tyr Tyr Asn Gln Ser Glu Ala Gly Ser His Ile Ile Gln Val
                 85                  90                  95
Met Tyr Gly Cys Asp Val Gly Pro Asp Gly Leu Leu Leu Arg Gly His
                100                 105                 110
Asp Gln Ser Ala Tyr Asp Gly Lys Asp Tyr Ile Ala Leu Asn Glu Asp
            115                 120                 125
Leu Ser Ser Trp Thr Ala Ala Asp Thr Ala Ala Gln Ile Thr Gln Arg
        130                 135                 140
Lys Trp Glu Ala Ala Arg Val Ala Glu Gln Leu Arg Ala Tyr Leu Glu
145                 150                 155                 160
Gly Leu Cys Val Glu Trp Leu Arg Arg Tyr Leu Glu Asn Gly Lys Glu
                165                 170                 175
Thr Leu Gln Arg Ala
            180

<210> SEQ ID NO 105
<211> LENGTH: 181
<212> TYPE: PRT
<213> ORGANISM: Homo sapiens
```

```
<400> SEQUENCE: 105

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Trp Ala
        35                  40                  45

Pro Trp Ile Glu Gln Glu Gly Pro Gly Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 106
<211> LENGTH: 296
<212> TYPE: PRT
<213> ORGANISM: Homo sapiens
<220> FEATURE:
<221> NAME/KEY: misc_feature
<222> LOCATION: (296)..(296)
<223> OTHER INFORMATION: Xaa can be any naturally occurring amino acid

<400> SEQUENCE: 106

Met Arg Val Thr Ala Pro Arg Thr Val Leu Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ala Met Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Pro Arg Met Ala Pro Arg Ala Pro Trp Ile Glu Gln Glu Gly
65                  70                  75                  80

Pro Glu Tyr Trp Asp Gly Glu Thr Arg Asn Met Lys Ala Ser Ala Gln
                85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Val Met Tyr Gly Cys Asp Val Gly
        115                 120                 125

Pro Asp Gly Arg Leu Leu Arg Gly His Asp Gln Ser Ala Tyr Asp Gly
    130                 135                 140

Lys Asp Tyr Ile Ala Leu Asn Glu Asp Leu Ser Ser Trp Thr Ala Ala
145                 150                 155                 160
```

```
Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Asn Pro Ser Pro Xaa
    290                 295

<210> SEQ ID NO 107
<211> LENGTH: 181
<212> TYPE: PRT
<213> ORGANISM: Homo sapiens

<400> SEQUENCE: 107

Ser His Ser Met Arg Tyr Phe Tyr Thr Ala Met Ser Arg Pro Gly Arg
1               5                   10                  15

Gly Glu Pro Arg Phe Ile Ser Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Asp Gly Glu Thr Arg
    50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asn Gln Tyr Ala Tyr Asp Gly Lys Asp Tyr Ile Ala Leu Asn Glu Asp
        115                 120                 125

Leu Ser Ser Trp Thr Ala Asp Thr Ala Ala Gln Ile Thr Gln Arg
    130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 108
<211> LENGTH: 181
<212> TYPE: PRT
<213> ORGANISM: Homo sapiens

<400> SEQUENCE: 108
```

Ser His Ser Met Arg Tyr Phe Tyr Thr Ala Met Ser Arg Pro Gly Arg
1               5                   10                  15

Gly Glu Pro Arg Phe Ile Ala Val Gly Tyr Val Asp Asp Thr Gln Phe
            20                  25                  30

Val Arg Phe Asp Ser Asp Ala Ala Ser Pro Arg Met Ala Pro Arg Ala
        35                  40                  45

Pro Trp Ile Glu Gln Glu Gly Pro Glu Tyr Trp Glu Gly Glu Thr Arg
50                  55                  60

Asn Met Lys Ala Ser Ala Gln Thr Tyr Arg Glu Asn Leu Arg Ile Ala
65                  70                  75                  80

Leu Arg Tyr Tyr Asn Gln Ser Glu Ala Gly Ser His Ile Ile Gln Val
                85                  90                  95

Met Tyr Gly Cys Asp Val Gly Pro Asp Gly Arg Leu Leu Arg Gly His
            100                 105                 110

Asp Gln Ser Ala Tyr Asp Gly Lys Asp Tyr Ile Ala Leu Asn Glu Asp
        115                 120                 125

Leu Ser Ser Trp Thr Ala Ala Asp Thr Ala Ala Gln Ile Thr Gln Arg
130                 135                 140

Lys Trp Glu Ala Ala Arg Val Ala Glu Gln Leu Arg Ala Tyr Leu Glu
145                 150                 155                 160

Gly Leu Cys Val Glu Trp Leu Arg Arg Tyr Leu Glu Asn Gly Lys Glu
                165                 170                 175

Thr Leu Gln Arg Ala
            180

<210> SEQ ID NO 109
<211> LENGTH: 362
<212> TYPE: PRT
<213> ORGANISM: Homo sapiens

<400> SEQUENCE: 109

Met Arg Val Thr Ala Pro Arg Thr Val Leu Leu Leu Leu Trp Gly Ala
1               5                   10                  15

Val Ala Leu Thr Glu Thr Trp Ala Gly Ser His Ser Met Arg Tyr Phe
            20                  25                  30

Tyr Thr Ala Met Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Pro Arg Met Ala Pro Arg Ala Pro Trp Ile Glu Gln Glu Gly
65                  70                  75                  80

Pro Glu Tyr Trp Asp Gly Glu Thr Arg Asn Met Lys Ala Ser Ala Gln
                85                  90                  95

Thr Tyr Arg Glu Asn Leu Arg Ile Ala Leu Arg Tyr Tyr Asn Gln Ser
            100                 105                 110

Glu Ala Gly Ser His Thr Leu Gln Arg Met Tyr Gly Cys Asp Val Gly
        115                 120                 125

Pro Asp Gly Arg Leu Leu Arg Gly His Asn Gln Tyr Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu

```
                        180                 185                 190
Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
                260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
        290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
                340                 345                 350

Ala Gln Gly Ser Asp Val Ser Leu Thr Ala
        355                 360
```

HLA-B57 OPEN CONFORMERS

CROSS-REFERENCE TO RELATED APPLICATIONS

This is a continuation the U.S. patent application Ser. No. 16/083,508 filed Sep. 9, 2018, which is the US National Stage of International Patent Application No. PCT/EP2017/055373 filed Mar. 7, 2017, which in turn claims the benefit of European Patent Application No. 16159099.7 filed Mar. 8, 2016. The contents of the foregoing applications are incorporated by reference herein in their entirety.

FIELD

The present invention relates to the use of HLA-B57 open conformers, particularly for use in the prophylaxis or treatment of cancer, and for use as an immunomodulator.

BACKGROUND

Human leukocyte antigens (HLA) belong to the classical major histocompatibility complex (MHC) protein family. The HLA complex helps the immune system distinguish the body's own proteins from proteins made by foreign invaders such as viruses and bacteria. Humans have three main classical MHC class I genes, known as HLA-A, HLA-B, and HLA-C. Classical HLA genes have many possible variations, allowing each person's immune system to react to a wide range of foreign invaders. Some HLA genes have hundreds of identified versions (alleles), each of which is given a particular number (such as HLA-B57). Closely related alleles are categorized together; for example, at least 82 very similar alleles are subtypes of HLA-B57. These subtypes are designated as HLA-B*5701 to HLA-B*5782, and the closely related HLA-B*5801.

Classical MHC-I molecules (designated HLA-I in humans) are trimeric structures comprising a membrane-bound heavy chain with three extracellular domains ($\alpha 1$, $\alpha 2$ and $\alpha 3$) that associates non-covalently with $\beta 2$-microglobulin ($\beta 3$ m) and a small peptide. HLA I heavy chains may exist in a form not associated to $\beta 2$-microglobulin or peptide. These forms are referred to as open conformers.

As all other HLA molecules, HLA-B57's principle function is to present cell-derived peptides to $CD8^+$ cytotoxic T lymphocytes (CTLs), as part of the adaptive immune response. Under normal physiological conditions, HLA-B57 molecules form heterotrimeric complexes that consist of B57 heavy chains, $\beta 2$-microglobulin, and peptides which are derived from self-proteins, viruses or bacteria. In this respect, HLA-B57 resembles all other class I HLA alleles. However, HLA-molecules may also be present in cells as free-heavy chains lacking $\beta 2m$-microglobulin and peptide, and can be referred to as HLA-B57 open conformers (Arosa et al. Open conformers: the hidden face of MHC-I molecules, Trends in Immunology 2007 March; 28(3):115-23).

Cancer is a group of diseases characterized by abnormal cells of the body undergoing uncontrolled and destructive growth. Cancer cells can spread around the body and metastasize to form tumors; this growth pattern is called malignant. Cancer can be treated by surgery, chemotherapy, radiation therapy, hormonal therapy, targeted therapy and immunotherapy. The choice of therapy depends on the type of cancer, the stage of the cancer (how much it has spread), age, health status, and additional personal characteristics. There is no single treatment for cancer, and patients often receive a combination of therapies and palliative care.

Cancer immunotherapy refers to a diverse set of therapeutic strategies designed to induce the patient's own immune system to fight the tumor, and is based on the insight that the progression of cancer, which involves the accumulation of diverse mutations, is monitored by the immune system. Immunotherapies either stimulate the activities of specific cell components of the immune system or counteract signals produced by cancer cells that suppress immune responses (Mahoney et al., Nat Rev Drug Discov. 2015 August; 14(8):561-84).

Different type of immune cells are involved in the immune response against cancer. Within this pool of white blood cells (immune contexture), the most notorious cells are: T-cells (cytotoxic CD8+ T-cells, T helper CD4+ cells—Th1, Th2, and Th17 phenotype), regulatory T cells (Tregs), Macrophages (M1 type-pro-inflammatory and M2 type-pro-tumoral), myeloid derived suppressor cells (MDSCs), natural killer cells (NK cells), and dendritic cells (DCs). These immune cells can be located in the center of the tumor, in the invasive margin or in the adjacent tertiary lymphoid structures (Fridman et al., Nat. Rev. Cancer. 2012, April: 12, 298-306).

The density and composition of the immune microenvironment is heterogeneous among patients and tumors. It is now well established that in general the tumor infiltration with M2-phenotype macrophages and myeloid derived suppressor cells (MDSCs) promotes tumor progression, whereas infiltration of cytotoxic CD8+ T-cells, Th1 phenotype cells and M1 type macrophages are often associated with good clinical outcome, and good response to immunotherapy. The clinical impact of other lymphoid and myeloid cell populations is less consistent and seems dependent on the tumor type and stage. The presence of Th17, and NK cells, and the absence/reduction of Treg cells in tumor infiltrates is correlated with good outcome in some cancer indications (Giraldo et al., Current Opinion in Immunology 2014, 27:8-15). A general overview of the balance between leukocyte infiltrates and clinical outcome is reviewed in FIG. 1. (Becht et al. Current Opinion in Immunology. 2016, 39:17-13).

Overall, modulating the immune contexture of tumors favoring the infiltration of M1 type macrophages, cytotoxic CD8 T-cells, and Th1 cells, and/or reducing the infiltration of MDSCs and M2 type macrophages is an enormous therapeutic avenue to treat cancer that is explored here with the use of $B57_2$-Fc proteins in diverse cancer indications.

SUMMARY

The present invention provides HLA-B57 open conformers.

According to one aspect, the invention provides HLA-B57 open conformers for use as a medicament.

According to an alternative aspect, the invention provides HLA-B57 open conformers for use in prevention or treatment of cancer, or as an immunomodulator.

According to another aspect of the invention, an isolated HLA-B57 open conformer protein is provided, particularly as a medicament, more particularly for use in the treatment or prevention of cancer, or as an immunomodulator.

According to another aspect of the invention an isolated HLA-B57 open conformer protein is provided as an immunomodulatory agent or for use as negative modulator of regulatory T cells (Tregs), for use in human diseases where Tregs impair the development of protective immunity, such as cancer and infectious diseases (von Boehmer et al. ibid.).

In certain embodiments, the HLA-B57 open conformer comprises two identical HLA-B57 polypeptide chains. In certain embodiments, the HLA-B57 open conformer comprises two different HLA-B57 polypeptide chains.

According to an alternative of this first aspect of the invention, an HLA-B57 open conformer is provided for use in the treatment or prevention of cancer, or for use as an immunomodulatory agent to treat infectious diseases, particularly for use in prevention or therapy human immunodeficiency virus (HIV), hepatitis A, B, C, virus (HAV HBV, HCV respectively), influenza virus, Respiratory Syncytial Virus (RSV), measles virus, herpes viruses and/or yellow fever virus. The open conformer according to this aspect is a fusion protein that exists as a dimer of two monomers, and each monomer independently of the other monomer comprises an HLA-B57 chain, and a polypeptide domain known to metabolically stabilize a polypeptide in vivo. One example of such stabilizing domain is an Fc (crystallisable fragment) domain of an immunoglobulin, particularly the Fc polypeptide domain of a gamma immunoglobulin. The HLA-B57 chain and the stabilizing domain may optionally be joined by an amino acid linker. An open conformer fusion protein comprising the HLA-B57 chain and an immunoglobulin Fc fragment is henceforth termed HLA-B57 Fc open conformer or $B57_2$-Fc herein.

The presence of the Fc domain in the fusion protein facilitates increasing the solubility, stability, avidity, half-life, and from a technological point of view, cost-effective production and purification in mammalian systems (protein A or G purification).

In certain embodiments, the HLA-B57 open conformer homodimer additionally comprises a peptide epitope fragment.

According to a second aspect of the invention an HLA-B57 open conformer monomer (i.e., the HLA-B57 unattached to a second HLA-B57 heavy chain polypeptide, and not bound by β2-microglobulin) is provided for use in the treatment or prevention of cancer, or for use as an immunomodulatory agent. In certain embodiments of this aspect, the HLA-B57 monomer additionally comprises a peptide epitope fragment.

This aspect can be summarized in the following items:

Item 1: An isolated single HLA-B57 heavy chain polypeptide monomer essentially free of associated β2-microglobulin for use as a medicament, particularly for use in the treatment or prevention of cancer, or for use as an immunomodulatory agent.

Item 2: The isolated single HLA-B57 heavy chain polypeptide monomer for use in the treatment or prevention of cancer or as an immunomodulatory agent according to item 1, wherein the monomer additionally comprises a peptide epitope fragment.

Item 3: The isolated single HLA-B57 heavy chain polypeptide monomer for use in the treatment or prevention of cancer or as an immunomodulatory agent according to items 1 or 2, wherein the HLA-B57 chain only consists of the HLA-B57 alpha 1, 2 and 3 domains.

Item 4: The isolated single HLA-B57 heavy chain polypeptide monomer for use in the treatment or prevention of cancer or as an immunomodulatory agent according to any one of the preceding items, wherein the HLA-B57 chain comprises the transmembrane domain and does not comprise the intracellular domain (cytoplasmic tail).

Item 5: The isolated single HLA-B57 heavy chain polypeptide monomer for use in the treatment or prevention of cancer or as an immunomodulatory agent according to any one of the preceding items, wherein the HLA-B57 chain has ≥70%, ≥80%, ≥85%, ≥90%, ≥92%, ≥93%, ≥94%, ≥95%, ≥96%, ≥97% or ≥98%, or 100%, sequence identity compared to any one of the sequences provided in table 1.

Item 6: A combination medicament comprising
a. an isolated single HLA-B57 heavy chain polypeptide monomer as specified in any one of items 1 to 5, and
b. a checkpoint inhibitory agent, particularly a checkpoint inhibitory antibody, and/or a checkpoint agonist agent, particularly a checkpoint agonist antibody.

Item 7: The combination medicament according to item 6, wherein said checkpoint inhibitory agent is selected from an inhibitor of CTLA4 interaction with CD80 or CD86, and an inhibitor of the interaction of PD-1 with its ligand PD-L1, particularly an antibody against any one of CTLA4, CD80, CD86, PD-1, PD-L1, more particularly a monoclonal antibody against human CTLA4, PD-1, or PD-L1, and/or wherein said checkpoint agonist agent is selected from an agonist antibody or ligand to 4-1 BB and/or 4-1 BBL (CD137L, Uniprot P41273).

BRIEF DESCRIPTION OF THE DESCRIBED SEQUENCES

Figure 1:
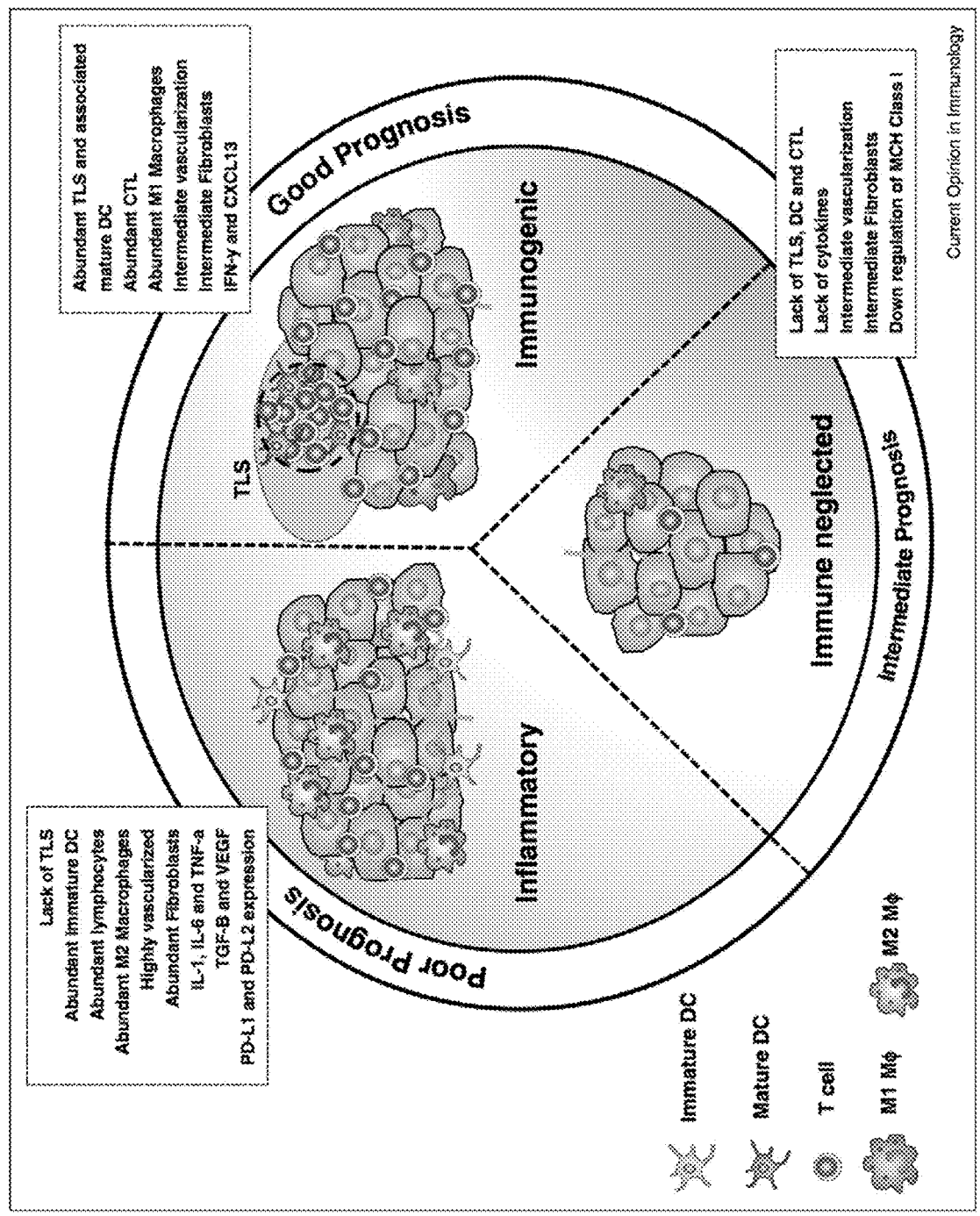
FIG. 1 Schematic representation depicting three different classifications of tumors based on their immune cell infiltrates. The 'immunogenic tumors' are characterized by abundant Cytotoxic T-Lymphocyte (CTL) infiltration, M1 type macrophages, the presence of Tertiary Lymphoid Structures (TLS) and low/moderate vascularization while associated with the longest patient's survival. The 'immune neglected' tumors are characterized by the lack of infiltration by immune cells, low/moderate vascularization and intermediate prognosis. Finally, the 'inflammatory tumors' are characterized by abundant CTL in the absence of TLS, conspicuous infiltration with M2 macrophages, severe vascularization and poor prognosis (Becht et al. Current Opinion in Immunology. 2016, 39:17-13).

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 95083_303_3701_seq, created Jun. 24, 2022, about 196 KB, which is incorporated by reference herein.

DETAILED DESCRIPTION

Terms and Definitions

Amino acid sequences are given from amino to carboxyl terminus. Capital letters for sequence positions refer to L-amino acids in the one-letter code (Stryer, Biochemistry, 3$^{rd}$ ed. p. 21).

The term open conformer as used in the present specification refers to an isolated HLA heavy chain molecule not associated to β2-microglobulin either as a monomer or as a dimer (homodimer or heterodimer). Certain embodiments of the open conformers disclosed herein are fusion protein monomers or dimers, wherein the HLA heavy chain is covalently linked to a stabilizing polypeptide region, particularly a crystallizable fragment immunoglobulin domain.

In the context of the present specification the terms sequence identity and percentage of sequence identity refer to the values determined by comparing two aligned sequences. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information (http://blast.ncbi.nlm.nih.gov/). One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless otherwise stated, sequence identity values provided herein refer to the value obtained with the BLAST suite of programs (Altschul et al., J. Mol. Biol. 215:403-410 (1990)) using the above identified default parameters for protein and nucleic acid comparison, respectively.

In the context of the present specification, the term major histocompatibility complex (MHC) is used in its meaning known in the art of cell biology and biochemistry; it refers to a cell surface molecule that displays a specific fraction (peptide), also referred to as an epitope, of a protein. There a two major classes of MHC molecules: class I and class II.

MHC class I heavy chain molecules usually (i.e. when not in open conformer form) occur as an alpha chain linked to a unit of the non-MHC molecule β2-microglobulin. The alpha chain comprises, in direction from the N-terminus to the C-terminus, a signal peptide, three extracellular domains (α1-3, with a1 being at the N terminus), a transmembrane region and a C-terminal cytoplasmic tail. The peptide being displayed or presented is held by the peptide-binding groove, in the central region of the α1/α2 domains.

In the context of the present specification, the term β2-microglobulin domain is used in its meaning known in the art of cell biology and biochemistry; it refers to a non-MHC molecule that is part of the MHC class I heterodimer molecule. In other words, it constitutes the β chain of the MHC class I heterodimer.

In the context of the present specification, the term human leukocyte antigen (HLA) is used in its meaning known in the art of cell biology and biochemistry; it refers to gene loci encoding the human MHC class I proteins. The three major MHC class I genes in HLA are HLA-A, HLA-B and HLA-C and all of these genes have a varying number of alleles, for example HLA-B has 3590 known alleles. Closely related alleles are combined in subgroups of a certain allele. For example the allele HLA-B57 has more than 100 closely related alleles that are, according to the WHO Nomenclature Committee for Factors of the HLA System, labelled HLA-B*57:01:01 to HLA-B*57:82. The full or partial sequence of all known HLA genes and their respective alleles are available to the person skilled in the art in specialist databases such as IMGT/HLA (available online at ebi.ac.uk/ipd/imgt/hla/) and are provided in table 1 of this specification.

In the context of the present specification, the term checkpoint inhibitory agent or checkpoint inhibitory antibody is meant to encompass an agent, particularly an antibody (or antibody-like molecule) capable of disrupting the signal cascade leading to T cell inhibition after T cell activation as part of what is known in the art the immune checkpoint mechanism. Non-limiting examples of a checkpoint inhibitory agent or checkpoint inhibitory antibody include antibodies to CTLA-4 (Uniprot P16410), PD-1 (Uniprot Q15116), PD-L1 (Uniprot Q9NZQ7), B7H3 (CD276; Uniprot Q5ZPR3), Tim-3, Gal9, VISTA, Lag3.

In the context of the present specification, the term checkpoint agonist agent or checkpoint agonist antibody is meant to encompass an agent, particularly but not limited to an antibody (or antibody-like molecule) capable of engaging the signal cascade leading to T cell activation as part of what is known in the art the immune checkpoint mechanism. Non-limiting examples of receptors known to stimulate T cell activation include CD122 and CD137 (4-1BB; Uniprot Q07011). The term checkpoint agonist agent or checkpoint agonist antibody encompasses agonist antibodies to CD137 (4-1 BB), CD134 (OX40), CD357 (GITR) CD278 (ICOS), CD27, CD28.

In the context of the present specification, the term antibody is used in its meaning known in the art of cell biology and immunology; it refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains inter-connected by disulfide bonds. Each heavy chain is comprised of a heavy chain variable region ($V_H$) and a heavy chain constant region ($C_H$). The heavy chain constant region is comprised of three domains, $C_H1$, $C_H2$ and $C_H3$. Each light chain is comprised of a light chain variable region (abbreviated herein as $V_L$) and a light chain constant region ($C_L$). The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

The term antibody-like molecule in the context of the present specification refers to a molecule capable of specific binding to another molecule or target with high affinity/a Kd≤10E-8 mol/l. An antibody-like molecule binds to its target similarly to the specific binding of an antibody. The term antibody-like molecule encompasses a repeat protein, such as a designed ankyrin repeat protein (Molecular Partners, Zurich), a polypeptide derived from armadillo repeat proteins, a polypeptide derived from leucine-rich repeat proteins and a polypeptide derived from tetratricopeptide repeat proteins.

The term antibody-like molecule further encompasses a polypeptide derived from protein A domains, a polypeptide derived from fibronectin domain FN3, a polypeptide derived from consensus fibronectin domains, a polypeptide derived from lipocalins, a polypeptide derived from Zinc fingers, a polypeptide derived from Src homology domain 2 (SH2), a polypeptide derived from Src homology domain 3 (SH3), a polypeptide derived from PDZ domains, a polypeptide derived from gamma-crystallin, a polypeptide derived from ubiquitin, a polypeptide derived from a cysteine knot polypeptide and a polypeptide derived from a knottin.

The term protein A domains derived polypeptide refers to a molecule that is a derivative of protein A and is capable of specifically binding the Fc region and the Fab region of immunoglobulins.

The term armadillo repeat protein refers to a polypeptide comprising at least one armadillo repeat, wherein an armadillo repeat is characterized by a pair of alpha helices that form a hairpin structure.

In the context of the present specification, the term crystallizable fragment (Fc) region is used in its meaning known in the art of cell biology and immunology; it refers to a fraction of an antibody comprising two identical heavy chain fragments comprised of a $C_H2$ and a $C_H3$ domain, covalently linked by disulfide bonds.

In the context of the present specification, the term dimer refers to a unit consisting of two subunits.

In the context of the present specification, the term homodimer refers to a dimer comprised of two subunits that are either identical or are highly similar members of the same class of subunits. One example for a homodimer would be a dimer consisting of two subunits independently selected from the list of HLA-B57 alleles. In certain embodiments, homodimers consist of two identical HLA-B57 alleles.

In the context of the present specification, the term amino acid linker refers to a polypeptide of variable length that is used to connect two polypeptides in order to generate a single chain polypeptide. Exemplary embodiments of linkers useful for practicing the invention specified herein are oligopeptide chains consisting of 1, 2, 3, 4, 5, 10, 20, 30, 40 or 50 amino acids. A non-limiting example of an amino acid linker is the polypeptide GGGGSGGGGSGGGGS (SEQ ID NO 109) that links an HLA-B57 polypeptide with an Fc domain.

In certain embodiments of any one of the aspects of the invention laid out above, a peptide epitope fragment is non-covalently attached to the polypeptide within the antigen presenting domain of the HLA-B57 peptide chain.

In certain embodiments of any one of the aspects of the invention laid out above, the HLA-B57 chain comprises only the extracellular HLA-B57 alpha 1, 2 and 3 domains. In these embodiments, the transmembrane and intracellular domains of the HLA-B57 chain are not included in the therapeutic polypeptide of the invention in order to allow its extracellular expression in recombinant cells. The person skilled in the art can easily identify the respective domains even in previously unknown HLA-B57 sequences by pairwise sequence alignment with annotated HLA-B57 sequences.

In certain embodiments of any one of the aspects of the invention laid out above, the HLA-B57 chain of the homodimer is selected from HLA-B*57:01, to HLA-B*57:82.

In certain embodiments of any one of the aspects of the invention laid out above, the HLA-B57 chain comprises only the HLA-B57 alpha 1, 2 and 3 domains, but not the transmembrane and intracellular domain of a sequence selected from Table 1.

In certain embodiments of any one of the aspects of the invention laid out above, the HLA-B57 chain has ≥70%, ≥80%, ≥85%, ≥90%, ≥92%, ≥93%, ≥94%, ≥95%, ≥96%, ≥97% or ≥98%, or 100% sequence identity compared to any one of the sequences provided in Table 1.

In certain embodiments, the HLA-B57 open conformer consists of two subunits independently selected from the above HLA-B57 alleles. In certain embodiments, homodimers consist of two identical HLA-B57 alleles.

In certain embodiments, the HLA-B57 open conformer comprises an Fc domain. In certain particular embodiments, the Fc domain comprises heavy chain constant regions $C_H2$ and $C_H3$ from immunoglobulin type G (IgG), type A (IgA), type D (IgD), type E (IgE) or type M (IgM).

In certain embodiments, the HLA-B57 open conformer comprises an amino acid linker joining a stabilizing domain, particularly an Fc domain, to the HLA polypeptide. In certain particular embodiments, the amino acid linker comprises 1 to 50 amino acids, particularly 5 to 40 amino acids, more particularly 10 to 30 amino acids, even more particularly 15 to 25 amino acids that link the HLA-B57 chain to the Fc domain as one single polypeptide chain.

According to a third aspect of the invention, a nucleic acid molecule encoding a HLA-B57 open conformer monomer, particularly an Fc open conformer monomer, according to the above aspects of the invention is provided for use in the treatment or the therapy of cancer. Expression of the open conformer in vivo from the nucleic acid molecule will, after dimerization, lead to the fusion protein polypeptide of the invention. The concept of expressing pharmaceutically active polypeptides from nucleic acids encoding them in the patient's body is well known and may confer significant benefits to the patient.

In certain embodiments, the nucleic acid molecule encodes a HLA-B57 open conformer monomer, particularly an Fc open conformer monomer comprising a peptide epitope fragment. In certain embodiments, the nucleic acid molecule encodes a HLA-B57 open conformer monomer, particularly an Fc open conformer monomer that comprises only the extracellular HLA-B57 alpha 1, 2 and 3 domains. In certain embodiments, the nucleic acid molecule encodes a HLA-B57 open conformer monomer, particularly an Fc open conformer monomer that comprises only the extracellular HLA-B57 alpha 1, 2 and 3 domains, and a peptide epitope fragment.

In certain embodiments, the nucleic acid molecule encodes a HLA-B57 open conformer monomer, particularly an Fc open conformer monomer that comprises an amino acid linker and/or an Fc (fragment crystallizable) domain, and is used in the treatment or the therapy of cancer.

According to a fourth aspect of the invention a recombinant expression vector comprising the nucleic acid molecule according to the third aspect of the invention is provided for use in the treatment or the therapy of cancer.

In certain embodiments the recombinant expression vector is a plasmid comprising a promoter that is operable in a mammalian cell, particularly in a human cell. The promoter is operably linked to the nucleic acid molecule of the invention.

According to another aspect of the invention a virus comprising the nucleic acid molecule according to the third aspect of the invention is provided for use in the treatment or the therapy of cancer. The nucleic acid molecule is under control of a promoter sequence operable in a mammalian cell, particularly in a human cell. In certain embodiments, the virus is an adenovirus, adeno-associated virus, a herpes virus or a lentivirus.

According to yet another aspect of the invention an in vitro genetically modified host cell comprising the nucleic acid molecule according to the third aspect of the invention is provided.

Another aspect of the invention provides for the use of the HLA-B57 Fc open conformer homodimer or fusion protein homodimer according to the first and second aspect of the invention in the manufacture of a medicament for the treatment or prevention of cancer.

According to yet another aspect, the invention provides a method of treatment for cancer, comprising administering an HLA-B57 Fc open conformer according to the first and second aspect of the invention to a patient in need thereof.

According to another aspect of the invention, a combination medicament is provided, wherein the combination medicament comprises:
  a HLA-B57 open conformer, particularly a HLA-B57 Fc open conformer, according to any one of the above aspects or embodiments of the invention,
  and
  a checkpoint inhibitory agent, particularly a checkpoint inhibitory antibody selected from an inhibitor of cytotoxic T-lymphocyte-associated protein 4 (CTLA4; also known as CD152) interaction with CD80 or CD86, an inhibitor of the interaction of programmed cell death protein 1 (PD-1; also known as CD279) with its ligand PD-L1, and a ligand of T cell immunoglobulin and mucin domain-containing 3 (TIM-3)
  a checkpoint agonist agent, particularly a checkpoint agonist antibody selected to bind to and activate the tumor necrosis factor receptor 4-1 BB (also known as CD137 or TNFRSF9).

In certain embodiments, the immune checkpoint inhibitor agent is an inhibitor of interaction of CTLA4 with CD80 or CD86.

In certain embodiments, the immune checkpoint inhibitor agent is ipilimumab (Yervoy; CAS No. 477202-00-9).

In certain embodiments, the immune checkpoint inhibitor agent is an inhibitor of interaction of programmed cell death protein 1 (PD-1) with its receptor PD-L1. In certain embodiments, the immune checkpoint inhibitor agent is selected from the clinically available antibody drugs nivolumab (Bristol-Myers Squibb; CAS No 946414-94-4), pembrolizumab (Merck Inc.; CAS No. 1374853-91-4), pidilizumab (CAS No. 1036730-42-3), atezolizumab (Roche AG; CAS No. 1380723-44-3), and Avelumab (Merck KGaA; CAS No. 1537032-82-8).

In certain embodiments, the immune checkpoint agonist agent is utomilumab (PF-05082566), a fully human IgG2 monoclonal antibody against 4-1 BB currently undergoing clinical trials.

In certain embodiments, the HLA-B57 open conformer, particularly the HLA-B57 Fc open conformer, is provided as parenteral dosage form, particularly confectioned for injection. In certain embodiments, the checkpoint inhibitory agent and/or checkpoint agonist agent are provided as parenteral dosage form, particularly confectioned for injection. In certain embodiments, both the HLA-B57 open conformer and the checkpoint inhibitory agent and/or checkpoint agonist agent are present in the same administration form.

In yet another aspect, the invention relates to a method for producing recombinant HLA heavy chain polypeptides. This method is summarized in the following items:
  Item A: A method for producing, by methods of recombinant biotechnology, a human HLA heavy chain polypeptide, wherein said method comprises the following steps:
    a. Expression step:
      i. a HLA-encoding nucleic acid sequence encoding at least the alpha 1 chain, the alpha 2 chain and the alpha 3 chain of a HLA heavy chain under control of a promoter sequence operable in a cell, particularly a eukaryotic cell, more particularly a mammalian cell, and
      ii. a β2-microglobulin encoding nucleic acid sequence encoding the human HLA beta 2 microglobulin (UniProt P61769) under control of a promoter sequence operable in said cell (the same cell as in item 1. a.) are co-expressed in a mammalian cell ("production cell line");
    b. Purification step: the resulting HLA-heavy-chain/β2-microglobulin complex is purified from the mammalian cell (the production cell line);
    c. Dissociation step: the purified HLA-heavy-chain/β2-microglobulin complex is dissociated under suitable conditions and the HLA heavy chain polypeptides are separated from the β2-microglobulin polypeptides;
    d. Refolding step: the separated HLA heavy chain polypeptides are incubated under conditions leading to refolding (of their native tertiary protein structure found in physiologically active HLA open conformer molecules).
  Item B: The method for producing a human HLA heavy chain polypeptide according to item A, wherein the HLA-encoding nucleic acid sequence comprises, from N to C terminus of the encoded polypeptide, the alpha 1 chain, the alpha 2 chain, the alpha 3 chain and a stabilizing sequence.
  Item C: The method for producing a human HLA heavy chain polypeptide according to item B, wherein the stabilizing sequence is selected from bovine serum albumin and an immunoglobulin constant fragment (Fc), particularly an immunoglobulin G constant fragment, more particularly an IgG4 Fc.

Item D: The method for producing a human HLA heavy chain polypeptide according to any of the preceding items, wherein the HLA-encoding nucleic acid sequence and the β2-microglobulin encoding nucleic acid sequence are present on the same nucleic acid vector molecule (particularly, a DNA expression plasmid).

Item E: The method for producing a human HLA heavy chain polypeptide according to any of the preceding items A to C, wherein the HLA-encoding nucleic acid sequence and the β2-microglobulin encoding nucleic acid sequence are present on different nucleic acid vector molecules (particularly, different DNA expression plasmids).

Item F: The method of item E, wherein the nucleic acid vector comprising the HLA-encoding nucleic acid sequence is present in approximately 1- to 5-fold excess, particularly 1.5 to 5-fold excess with respect to the nucleic acid vector comprising the β2-microglobulin encoding nucleic acid sequence, particularly in approximately 3-fold excess.

Item G: The method of any of the preceding items, wherein the HLA-encoding nucleic acid sequence comprises an immunoglobulin Fc fragment as a stabilizing sequence and the purification step is effected by adsorbing the recombinant HLA heavy chain polypeptides to a surface linked to protein A.

Item H: The method of any of the preceding items, wherein the dissociation step is effected by treatment under acidic conditions, particularly at approximately pH 2, and dialysis under reductive conditions.

Item I: The method of any of the preceding items, wherein the refolding step is effected by treatment under neutral conditions.

More specifically pointed at the B57 open conformers specified herein, the method can be summarized in the following items:

Item A': A method for producing, by methods of recombinant biotechnology, a human HLA-B57 heavy chain polypeptide, wherein said method comprises the following steps:
  a. Expression step:
    i. a HLA-B57-encoding nucleic acid sequence encoding at least the alpha 1 chain, the alpha 2 chain and the alpha 3 chain of a HLA-B57 heavy chain under control of a promoter sequence operable in a cell, particularly a eukaryotic cell, more particularly a mammalian cell, and
    ii. a β2-microglobulin encoding nucleic acid sequence encoding the human HLA beta 2 microglobulin (UniProt P61769) under control of a promoter sequence operable in said cell (the same cell as in item 1. a.) are co-expressed in a mammalian cell ("production cell line");
  b. Purification step: the resulting HLA-B57-heavy-chain/β2-microglobulin complex is purified from the mammalian cell (the production cell line);
  c. Dissociation step: the purified HLA-B57-heavy-chain/β2-microglobulin complex is dissociated under suitable conditions and the HLA heavy chain polypeptides are separated from the β2-microglobulin polypeptides;
  d. Refolding step: the separated HLA-B57 heavy chain polypeptides are incubated under conditions leading to refolding (of their native tertiary protein structure found in physiologically active HLA open conformer molecules).

Item B': The method for producing a human HLA-B57 heavy chain polypeptide according to item A', wherein the HLA-B57-encoding nucleic acid sequence comprises, from N to C terminus of the encoded polypeptide, the alpha 1 chain, the alpha 2 chain, the alpha 3 chain and a stabilizing sequence.

Item C': The method for producing a human HLA-B57 heavy chain polypeptide according to item B', wherein the stabilizing sequence is selected from bovine serum albumin and an immunoglobulin constant fragment (Fc), particularly an immunoglobulin G constant fragment, more particularly an IgG4 Fc.

Item D': The method for producing a human HLA-B57 heavy chain polypeptide according to any of the preceding items, wherein the HLA-encoding nucleic acid sequence and the 62-microglobulin encoding nucleic acid sequence are present on the same nucleic acid vector molecule (particularly, a DNA expression plasmid).

Item E': The method for producing a human HLA-B57 heavy chain polypeptide according to any of the preceding items A' to C', wherein the HLA-encoding nucleic acid sequence and the 62-microglobulin encoding nucleic acid sequence are present on different nucleic acid vector molecules (particularly, different DNA expression plasmids).

Item F': The method of item E', wherein the nucleic acid vector comprising the HLA-encoding nucleic acid sequence is present in approximately 1- to 5-fold excess, particularly 1.5 to 5-fold excess with respect to the nucleic acid vector comprising the 62-microglobulin encoding nucleic acid sequence, particularly in approximately 3-fold excess.

Item G': The method of any of the preceding items, wherein the HLA-B57-encoding nucleic acid sequence comprises an immunoglobulin Fc fragment as a stabilizing sequence and the purification step is effected by adsorbing the recombinant HLA heavy chain polypeptides to a surface linked to protein A.

Item H': The method of any of the preceding items, wherein the dissociation step is effected by treatment under acidic conditions, particularly at approximately pH 2, and dialysis under reductive conditions.

Item I': The method of any of the preceding items, wherein the refolding step is effected by treatment under neutral conditions.

Wherever alternatives for single separable features such as, for example, an allele or coding sequence are laid out herein as "embodiments", it is to be understood that such alternatives may be combined freely to form discrete embodiments of the invention disclosed herein.

The invention is further illustrated by the following examples, from which further embodiments and advantages can be drawn. These examples are meant to illustrate the invention but not to limit its scope.

Examples

The inventors surprisingly found that HLA-B57 open conformers interact with different immune modulatory surface receptors present in NK, T cells, myeloid derived cells (macrophages and MDSCs), and regulate the differentiation and suppressive function of Tregs in vitro.

The inventors surprisingly found that HLA-B57 open conformers, particularly when present as fusion proteins comprising an Fc immunoglobulin fragment, could be useful in cancer therapy. HLA-B57-Fc molecules may be used alone or in combinations with other cancer therapeutics.

Additionally, they discovered a novel in vivo mode of action with injections of $B57_2$-Fc as monotherapy or combinatorial approaches using checkpoint inhibitors or agonist antibodies. $B57_2$-Fc therapy alone or combinations can regulate the infiltration of diverse sets of leukocytes into the tumors as determined by the increased ratio of M1/M2 cells, increased infiltration of NK cells, increased CD8+ T cells/Treg ratio, and reduced infiltration of MDSCs. Overall, the mode of action of $B57_2$-Fc alone or in a combinatorial approach with antagonistic/agonistic antibodies is of undoubted relevance in the treatment of cancer, and correlates to the current clinical need in cancer immunotherapy.

HLA-B57 Fc open conformers can be used as a therapeutic to target diseases where immunomodulation is a therapeutic approach, as is the case of cancer and infectious diseases.

In Vitro Tests

Figure 2:
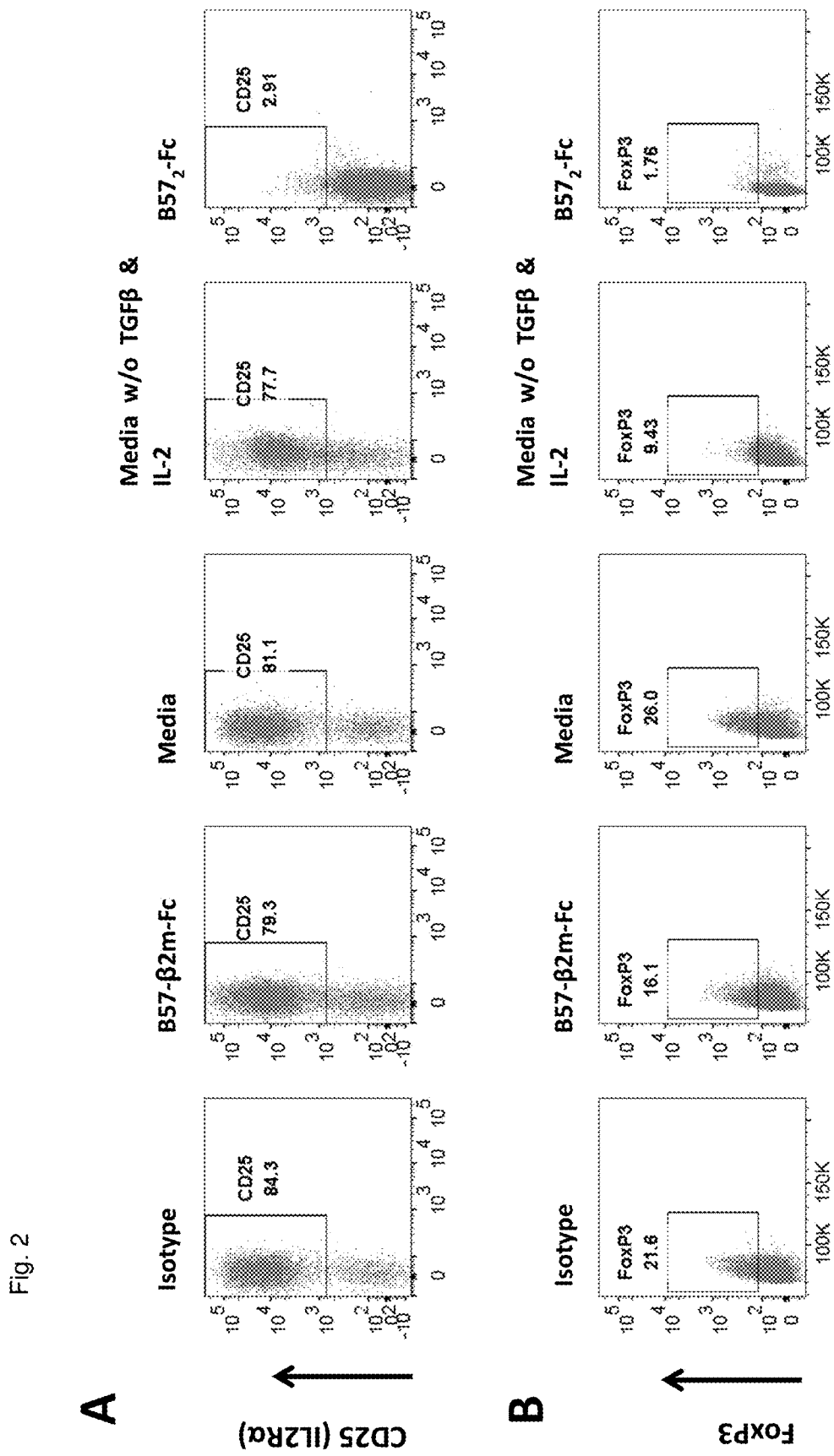
FIG. 2 shows that $B57_2$-Fc blocks mouse $CD4^+$ T cell conversion into iTreg. Incubation of $B57_2$-Fc in a dose dependent manner with naïve $CD4^+$ T cells blocks the conversion to iTregs. A) $B57_2$-Fc blocks the expression of CD25 (lineage marker of Tregs) in a dose dependent matter (µg/200 µL) (C). B) $B57_2$-Fc blocks the expression of FoxP3 (differentiation marker of Tregs) in a dose dependent matter (µg/200 µL) (D). Control B57132m-Fc, isotype, media supplemented with TGFβ and IL-2 and media w/o supplementation demonstrate the specific influence of $B57_2$-Fc on iTreg conversion.
Figure 2:
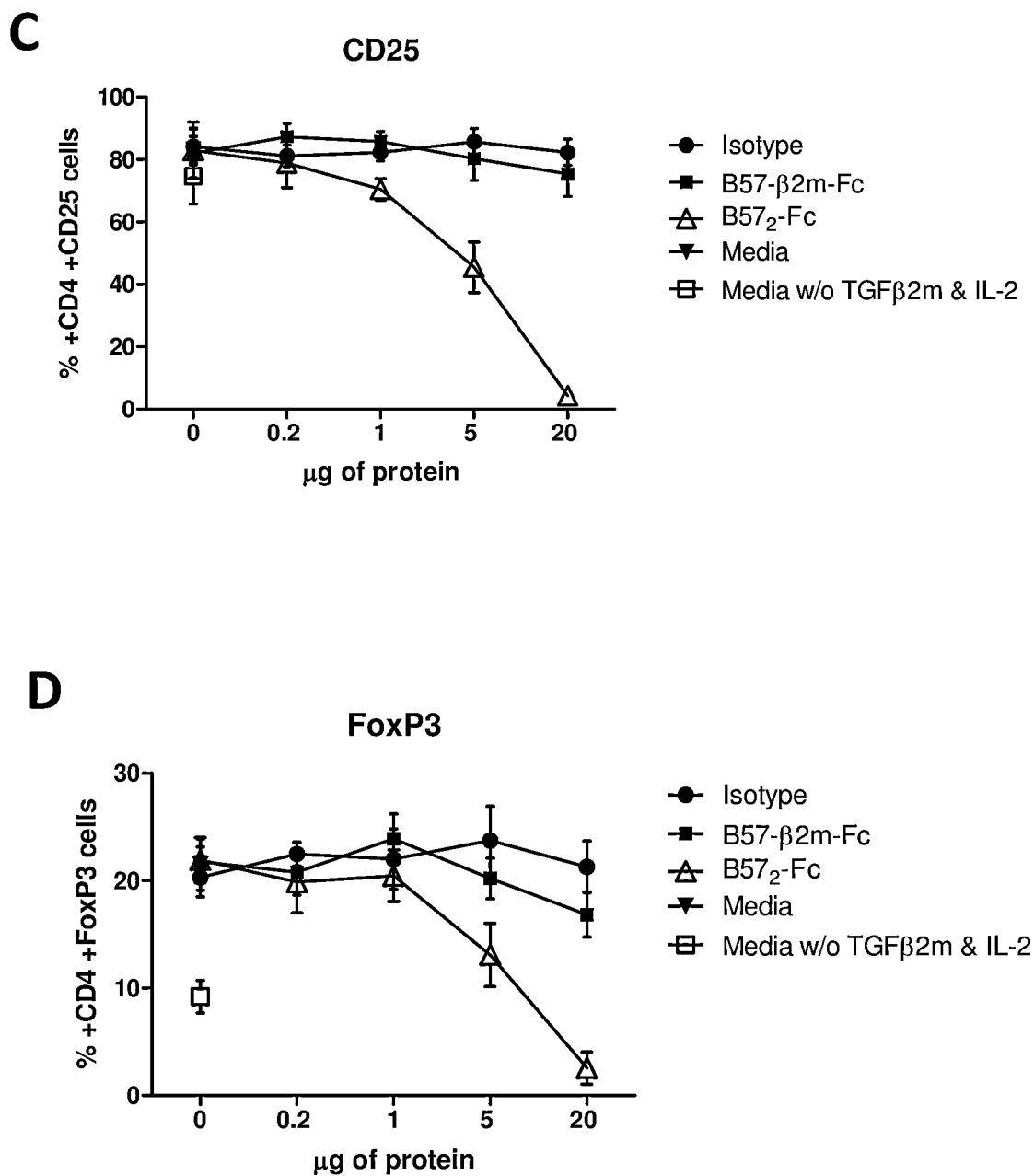
Figure 3:
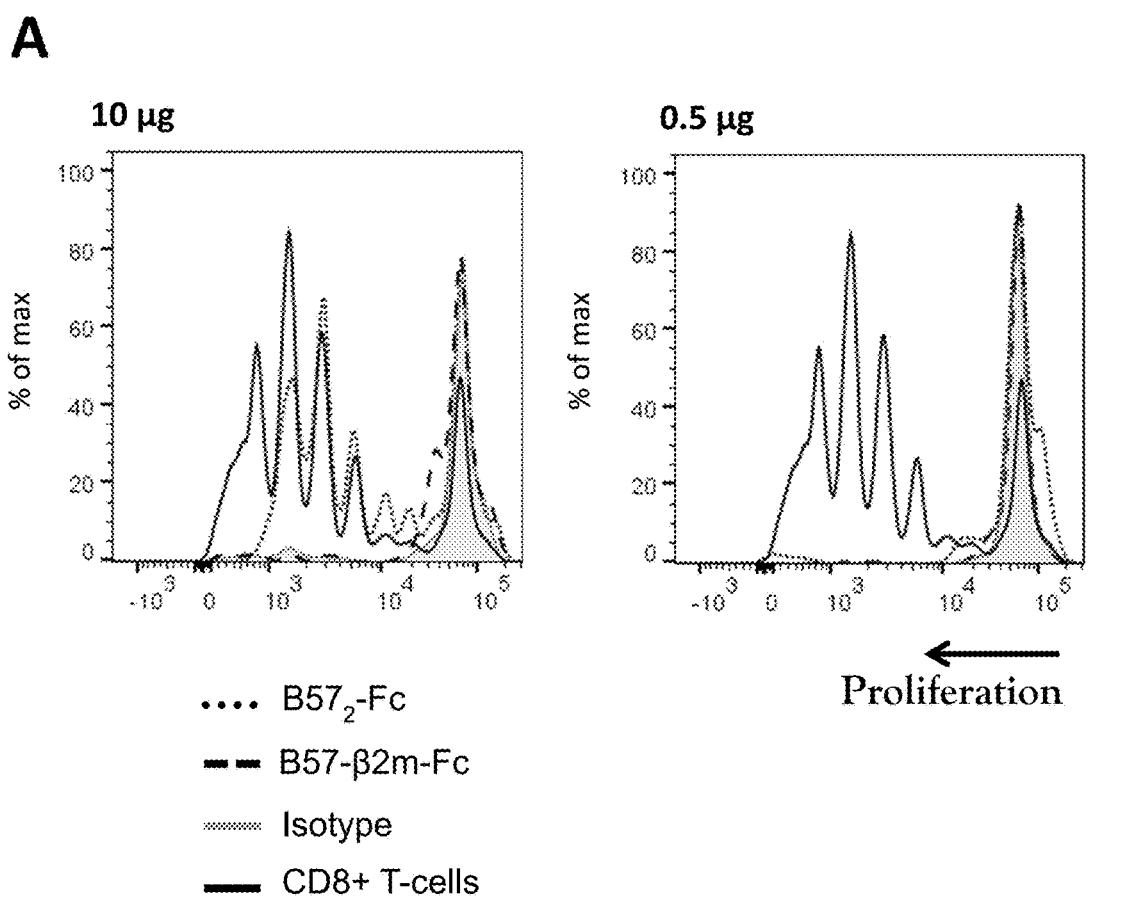
FIG. 3 shows that $B57_2$-Fc impairs the suppression of murine Tregs in a dose dependent matter. A) histogram of proliferation from CD8+ T cells and Tregs depicting $B57_2$-Fc blocking the suppression of mouse Tregs and allowing the proliferation of $CD8^+$ T cells. Control B57-β2m-Fc, and isotype do not alter the suppression function of murine Tregs. B) % of iTreg suppression of murine $CD8^+$ T cells at different concentrations of $B57_2$-Fc (µg/200 µL).
Figure 3:
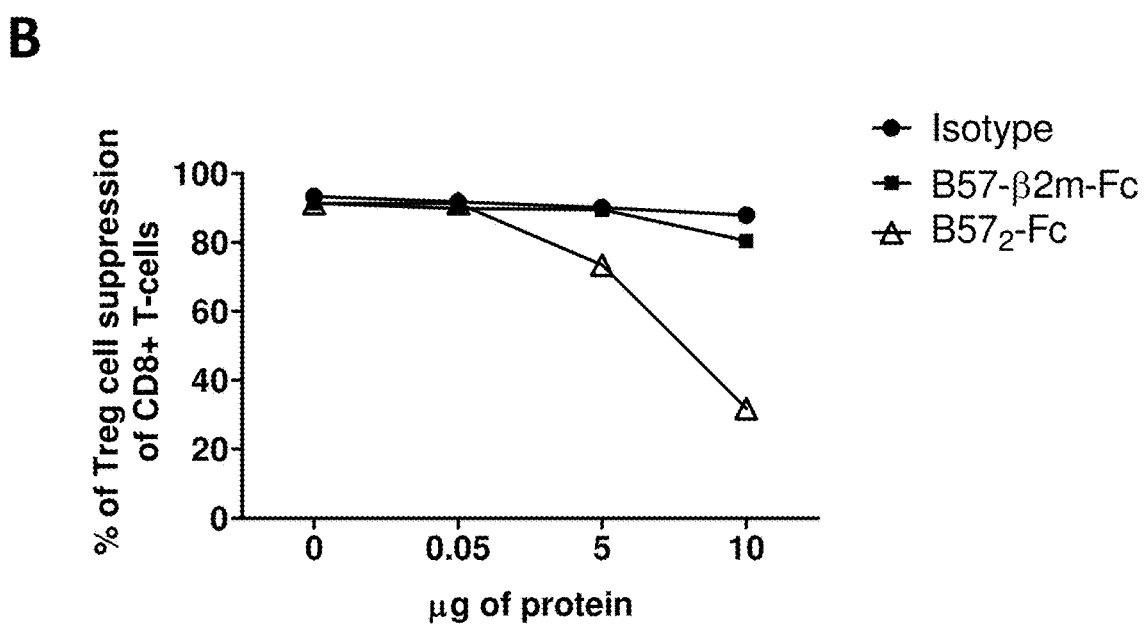

The $B57_2$-Fc molecule is able to modulate immune responses through blocking iTreg differentiation and negatively influencing Tregs suppression (FIG. 2-3)

$B57_2$-Fc Blocks Conversion of Murine CD4+ T Cells Into iTregs

The influence of HLA molecules with naïve CD4+ T cells for iTreg conversion was analysed in a dose dependent matter (μg/mL) with $B57_2$-Fc, B57-β2m-Fc, isotype and PBS incubated with naïve CD4+ T cells in optimal culture conditions for iTreg conversion. $B57_2$-Fc demonstrated to down modulate the induction of CD25 (FIG. 2A, C) and FoxP3 (FIG. 2B, D).

$B57_2$-Fc Impairs the Suppression of Mouse CD8+ T Cells by Tregs

The suppressive function of murine Tregs using violet-labelled naïve CD8+ T cells as responder cells was determined (FIG. 3). Tregs were co-cultured with $B57_2$-Fc and controls B57-β2m-Fc, and isotype antibody, and proliferation of CD8+ T cells was measured after 96 h. CD8+ T cells alone showed strong proliferation and, as expected, Treg cells suppressed the proliferation of CD8+ T cells when incubated with controls (B57-β2m-Fc, and isotype). Strikingly, the suppressive function of Tregs was greatly impaired in the presence of $B57_2$-Fc indicated by a strong proliferation of CD8+ T cells (FIG. 3A). The effect of $B57_2$-Fc was dose dependent (FIG. 3B).

$B57_2$-Fc Impairs the Proliferation of Leukaemia T Cells

Figure 4:
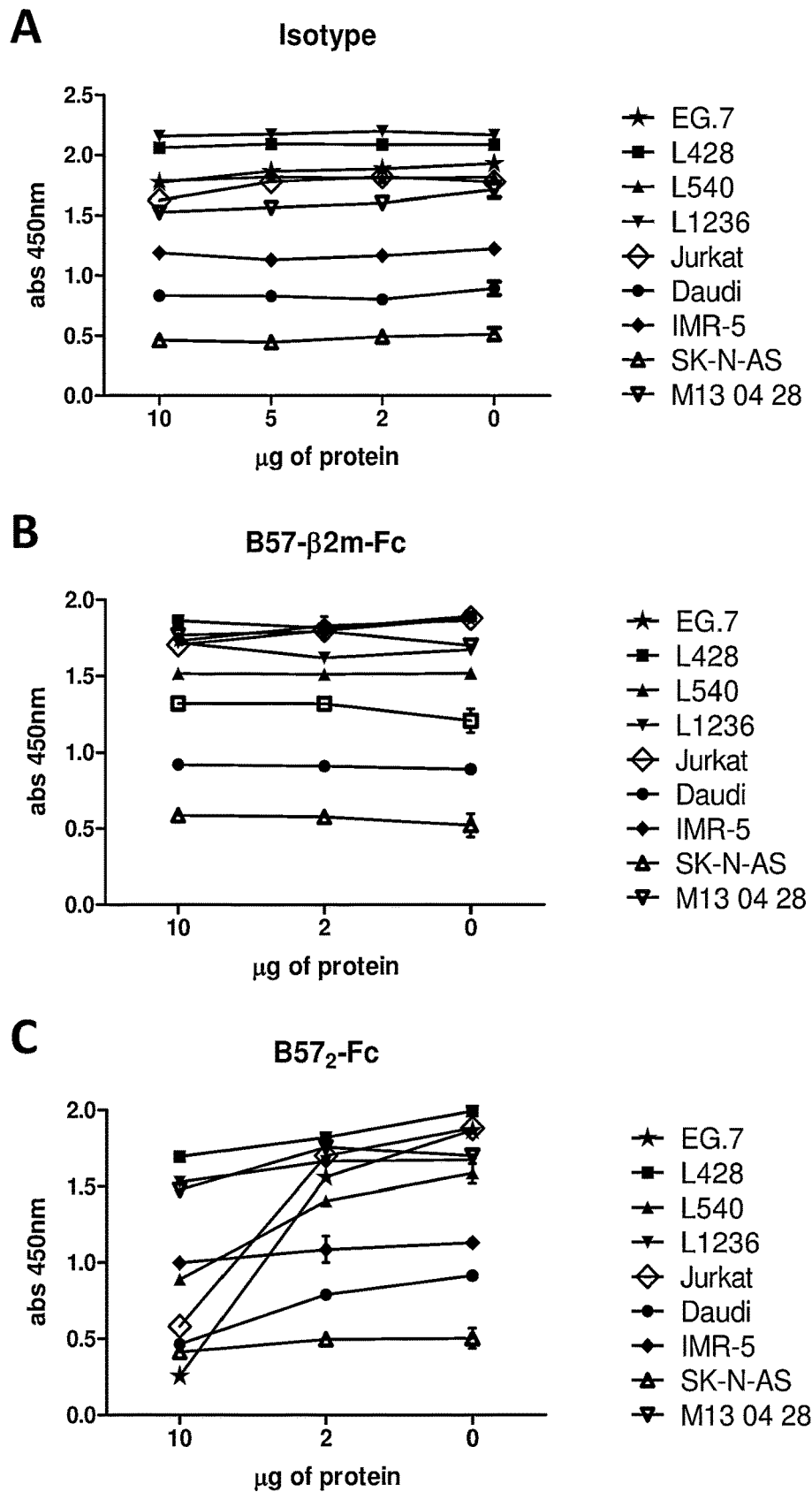
FIG. 4 shows that $B57_2$-Fc suppresses lymphoma T cells. A-C) suppression assays to determine the proliferation of cells in the presence of (A) control isotype, (B) control B57-β2m-Fc, and (C) $B57_2$-Fc. $B57_2$-Fc suppress human (Jurkat) and mouse (EG.7) lymphoma cell lines in a dose dependent manner (µg/200 µL) when compared to control cell lines.
Figure 5:
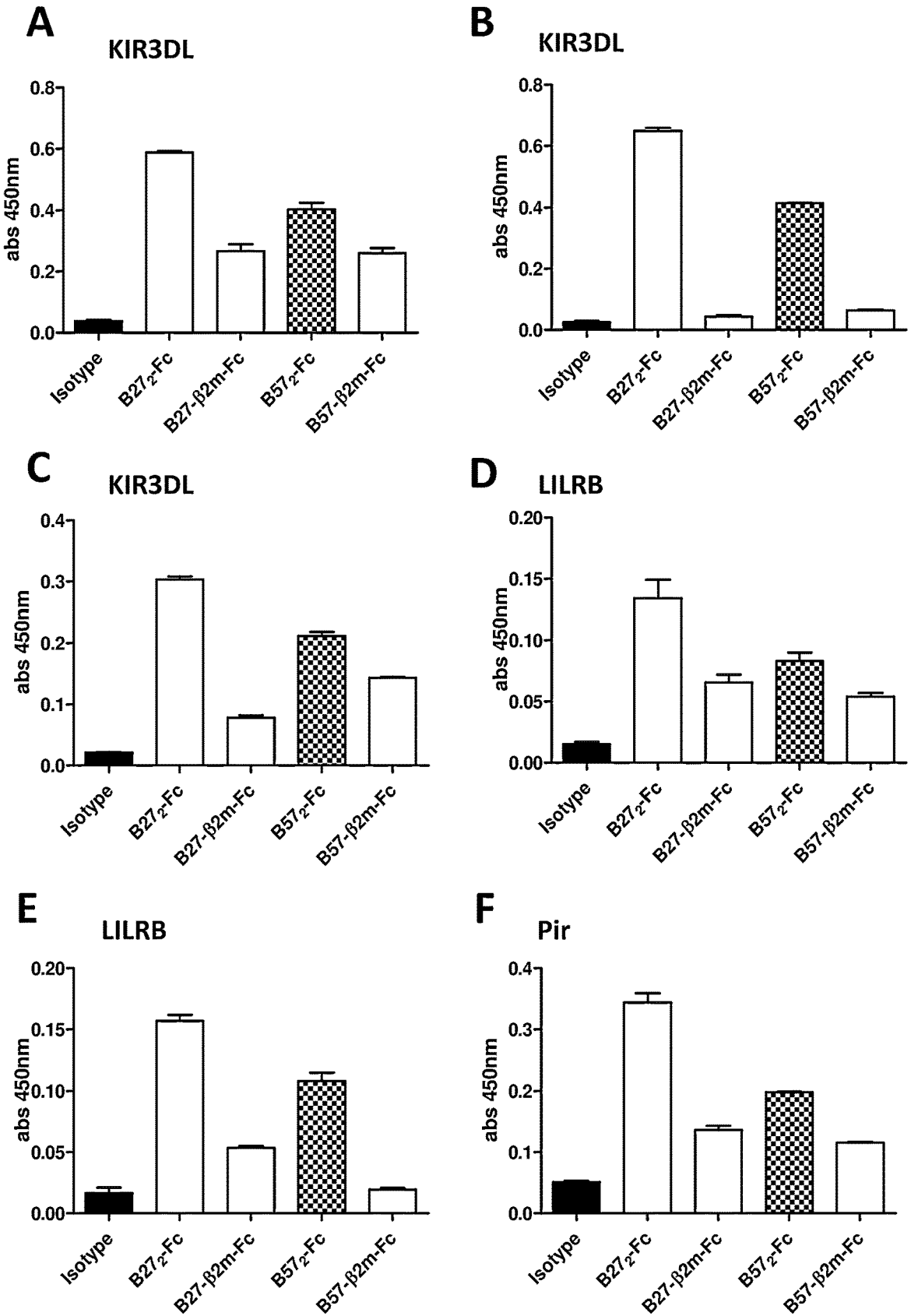
FIG. 5 shows the interaction B57$_2$-Fc to different immune regulatory receptors of leukocytes populations. A) KIR3DL1 (expressed in NK cells and subsets of T cells); B) KIR3DL2 (expressed in NK cells and subsets of T cells); C) KIR3DL3 (expressed in NK cells and subsets of T cells); D) LILRB1 (expressed in populations of NK cells, T cells, monocytes, and macrophages); E) LILRB2 (expressed mostly in macrophages and MDSCs), and F) PirB (murine homologue to LILRB2) by enzyme-linked immunosorbent assay (ELISA).

We determined the effect of $B57_2$-Fc proliferation effect in different cancer cell lines (FIG. 4). Results demonstrated that $B57_2$-Fc modulates the proliferation of lymphoma T cell lines, when compared to control counterpart B57-β2m-Fc or isotype IgG4, indicating its potential application to the treatment of lymphoma as a targeted therapy.

$B57_2$-Fc Binds to Immunomodulatory Receptors Expressed in Diverse Types of Leukocytes We determined if $B57_2$-Fc interacts with specific immune regulatory receptors by enzyme-linked immunosorbent assay (ELISA). Results demonstrated that $B57_2$-Fc interacts with KIR3DL1, KIR3DL2, KIR3DL3, LILRB1, LILRB2 and Pirb receptors in a matter different than its B57-β2m-Fc control counterparts (FIG. 5A-D). Furthermore we compared also $B27_2$-Fc, and B27-β2m-Fc to demonstrate if similar HLA open conformer molecules interact with same receptors but with different affinities.

Production of B57 Open Conformers as a Human Fc Fusion Protein in CHO Cells

Figure 6:
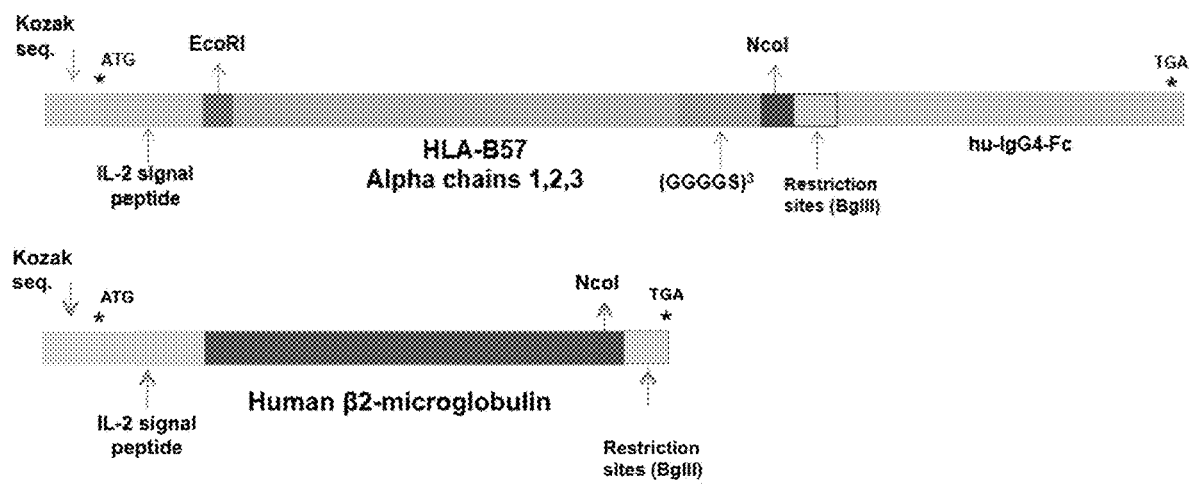
FIG. 6 shows the schematic representation of B57-Fc and β2m DNA cassettes and expression of B57-β2m-Fc molecules from CHO cells. A) alpha 1, 2 and 3 domains of HLA-B57 heavy chain inserted into a human IgG4-Fc vector cassette; and the human-β2 microglobulin inserted in a separate vector cassette. B) Transfections in Chinese hamster ovary cells (CHO) cells are performed using both the B57-Fc-vector+β2m-vector at a ratio of 1:1 for the extracellular production of the B57-β2m-Fc protein. Supernatants were collected and B57-β2m-Fc purified using standard antibody purification protocols. β2m is removed from the B57-β2m-Fc complex and following B57-Fc monomers are refolded to form B57$_2$-Fc homodimers
Figure 6:
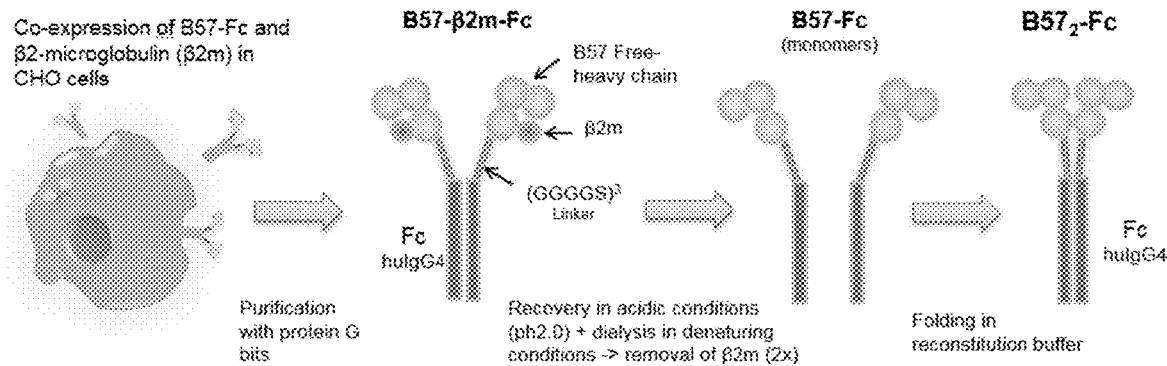

A valid strategy, from a therapeutic point of view, is to produce HLA-B57 open conformer molecules in stable format (Fc fusion), to increase solubility, stability, avidity, half-life, and from a technological point of view, cost-effective production and purification in mammalian systems. B57-β2m-Fc complex was successfully produced by inserting the alpha 1, 2 and 3 domains of HLA-B57 into a human IgG4-Fc vector cassette (FIG. 6A), together with a human-β2m vector, necessary for extracellular production of the B57-β2m-Fc protein (FIG. 6A,B). Transfections in Chinese hamster ovary cells (CHO) cells were performed using both the B57-Fc-vector+β2m-vector at a ratio of 1:1. Supernatants were collected and B57-β2m-Fc purified using standard antibody purification protocols (Recombinant Protein Purification Handbook, principles and methods. 2009. GE Healthcare, 18-1142-75) (FIG. 6B). Separation of β2m from B57-Fc free-heavy chains was performed using denaturing conditions by SEC or dialysis methods. Refolding of $B57_2$-Fc was assessed using the dilution method in refolding buffer and analysed by western blot (data not shown).

Pre-Clinical Combination Therapy Tests of $B57_2$-Fc with PD-1, PD-L1 and 4-1BB Antibodies in Diverse Syngeneic Colon Cancer Mouse Models The in vivo proof of concept study of $B57_2$-Fc as an immunomodulatory therapeutic molecule was demonstrated in murine colon carcinoma (C38), pancreatic cancer (Pan02) and melanoma (B16-F10) syngeneic mouse models as monotherapy and in combination with PD-1, PD-L1 or 4-1 BB antibodies.

For the colon carcinoma model, following established protocols C38 fragment tumours were subcutaneously injected in the flank of syngeneic mice. Once the tumour reached ≈80 mm3 (between 1-2 weeks after transplantation of tumors), mice were statistically distributed according to their tumor volume. $B57_2$-Fc was injected i.p. seven times every $3^{rd}$ day (Q3Dx7), and PD-1 injected 4 times twice a week (biwkx2) (FIG. 7A).

Figure 7:
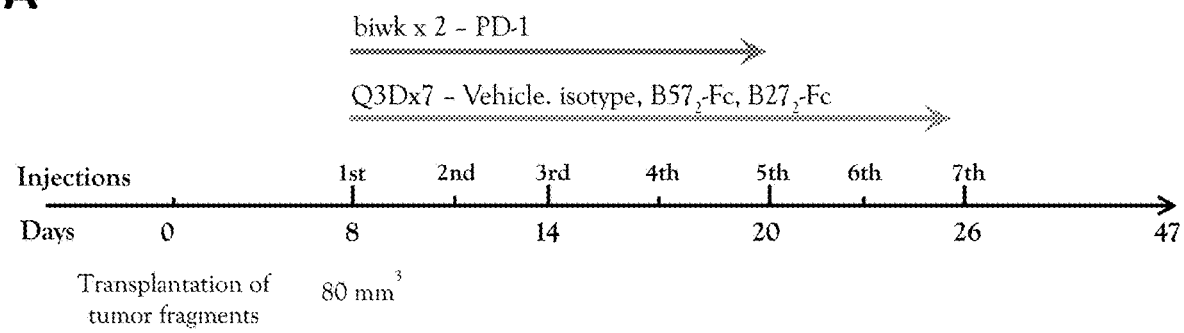
FIG. 7 shows the combination of B57$_2$-Fc with PD-1 antibodies reduce the size of tumors in the C38 murine syngeneic colon carcinoma model. A) Experimental design of injection time points of colon carcinoma cells (C38) and injection of compounds. B) Mean average tumor volume mm$^3$ of treated groups (n=6). C) % of tumor inhibition of B57$_2$-Fc and PD-1 treated groups compared to isotype. The experimental design of injection of substances was as follow: vehicle PBS Q3Dx7, isotype (10 mg/Kg) Q3Dx7; B57$_2$-Fc (10 mg/Kg) Q3Dx7; PD-1 biwkx2 (200 g); and B57$_2$-Fc+PD-1 (Q3Dx7 and biwkx2, respectively). Tumor volumes are expressed as mean±SEM and analysed by two-way ANOVA followed by Bonferroni post-hoc analysis, **$p<0.01$. Q=days between injections; Dx=number of injections, biwk=twice a week.
Figure 7:
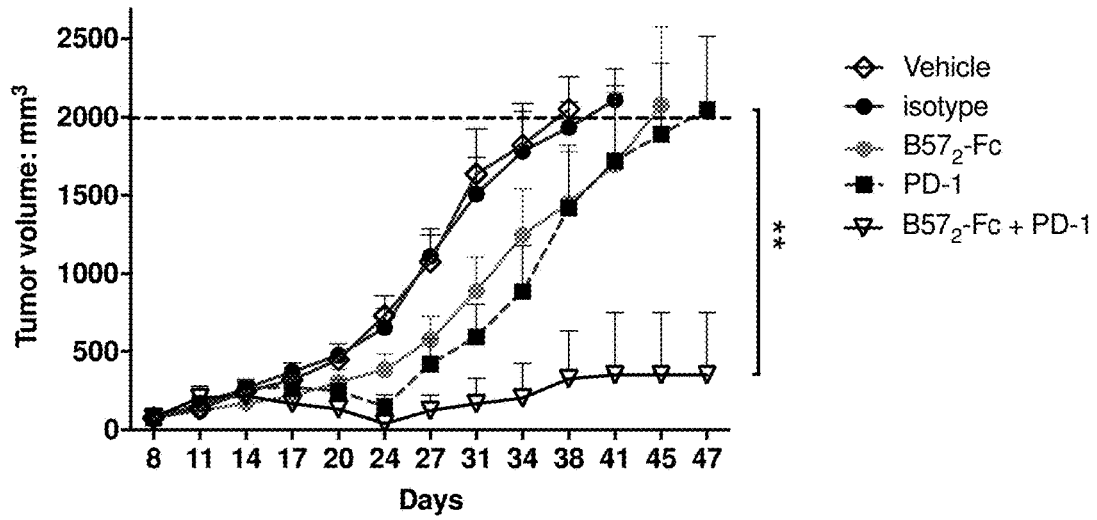
Figure 7:
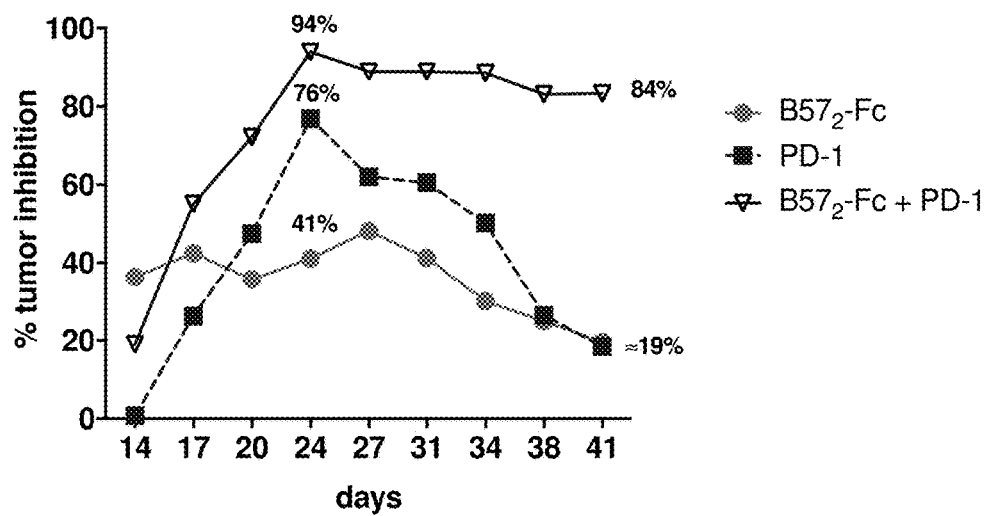

In colon cancer (C38) data demonstrated that the combination of $B57_2$-Fc with PD-1 antibodies significantly reduce tumors (FIG. 7B). Combo therapy $B57_2$-Fc+PD-1 vs isotype control antibody strikingly reduced tumor volume (333 $mm^3$ vs 2120 $mm^3$, respectively p<0.01). Additionally, combo therapy $B57_2$-Fc+PD-1 vs PD-1 monotherapy showed also significant tumor size reduction (333 $mm^3$ vs 1423 $mm^3$, respectively, p<0.01) (FIG. 7B). $B57_2$-Fc monotherapy or PD-1 monotherapy showed no differences vs. isotype control at the end of the experiment, however at day 24, $B57_2$-Fc treated mice were significantly different from isotype (384 $mm^3$ vs 652 $mm^3$, p<0.05), as well as PD-1 vs isotype (151 $mm^3$ vs 652 $mm^3$, p<0.01), (FIG. 7B), indicating that $B57_2$-Fc monotherapy has also immunomodulatory effects on the tumor progression of colon cancer mice.

For the pancreas (Pan02) and melanoma (B16F10) mouse models, following established protocols cells were injected at $1\times10^5$ in the right flank of syngeneic mice respectively. Once the tumor reached ≈80 mm3 (between 1-2 weeks after injection of cells) mice were statistically distributed according to their tumor volume (FIG. 8A, 14A)

Figure 8:
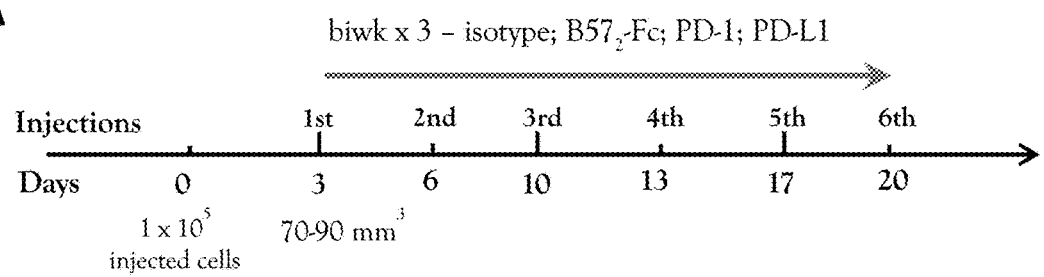
FIG. 8 shows the combination of B57$_2$-Fc with PD-1 antibodies reduce the size of tumors in the pancreatic (Pan02) cancer mouse model. A) Experimental design of injection time points of pancreatic cancer cells (Pan02) and injection of compounds. B) Mean average tumor volume mm$^3$ of treated groups (n=8) with B57$_2$-Fc and/or PD-1. The experimental design of injection of substances was as follow: isotype (5 mg/Kg) biwkx3; B57$_2$-Fc (5 mg/Kg) biwkx 3; PD-1 (5 mg/Kg) biwkx3; and B57$_2$-Fc+PD-1 (biwkx3). Tumor volumes are expressed as mean±SEM and analysed by two-way ANOVA followed by Bonferroni post-hoc analysis, *$p<0.05$; $p<0.01$; **$p<0.0001$. biwk=twice a week.
Figure 8:
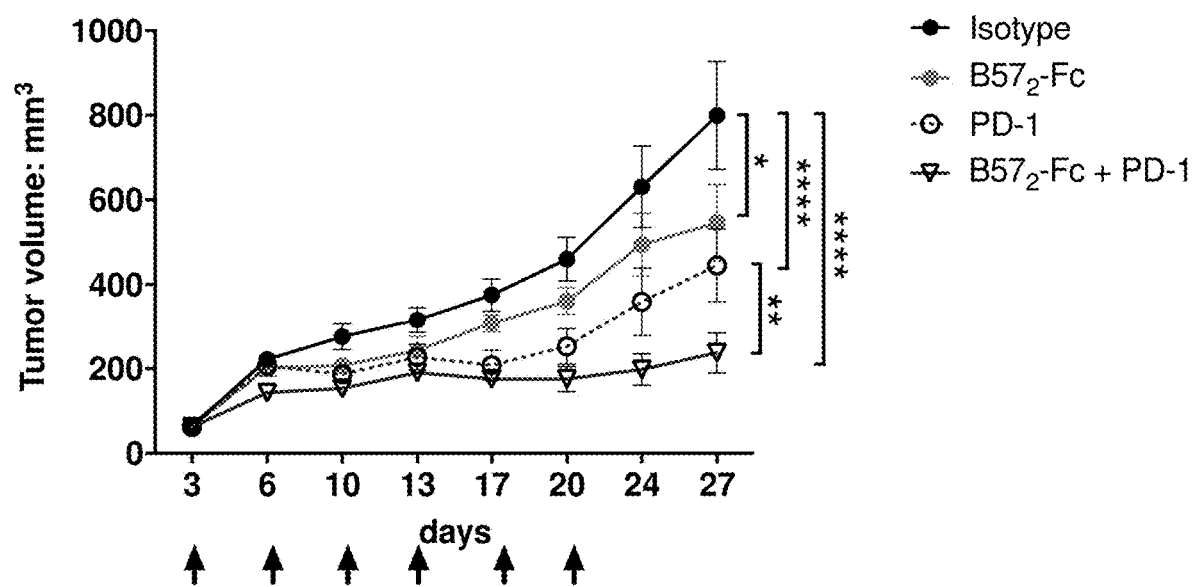
Figure 9:
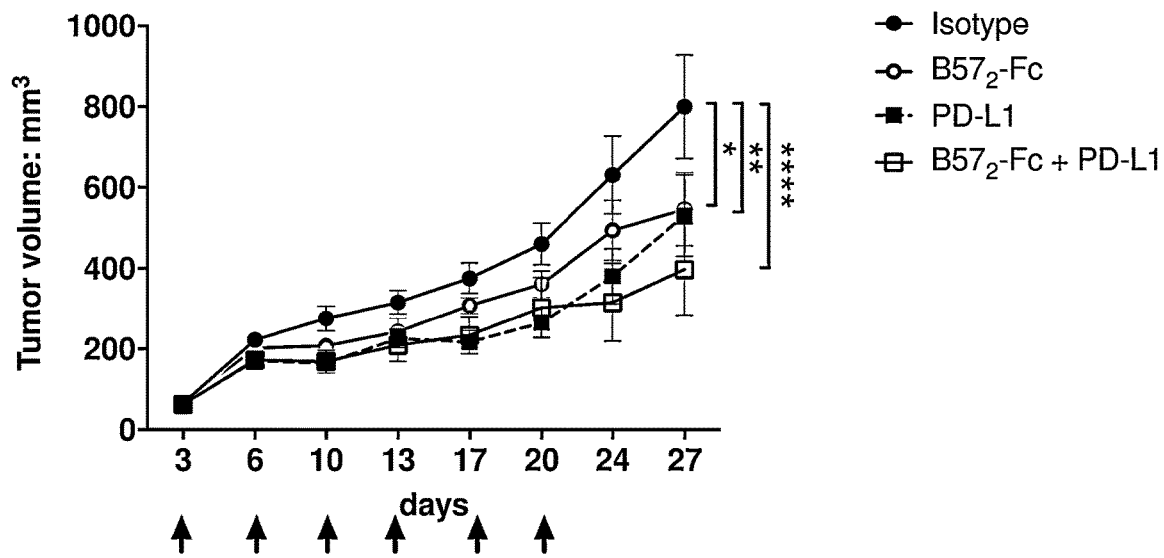
FIG. 9 shows the combination of B57$_2$-Fc with PD-L1 antibodies reduce the size of tumors in the pancreatic (Pan02) cancer mouse model. A) Mean average tumor volume mm$^3$ of treated groups (n=8) with B57$_2$-Fc and/or PD-L1. B) % of tumor inhibition of B57$_2$-Fc, PD-1 and PD-L1 treated groups compared to isotype. The experimental design of injection of substances was as follow: isotype (5 mg/Kg) biwkx3; B57$_2$-Fc (5 mg/Kg) biwkx3; PD-L1 (5 mg/Kg) biwkx3; and B57$_2$-Fc+PD-L1 (biwkx3). Tumor volumes are expressed as mean±SEM and analysed by two-way ANOVA followed by Bonferroni post-hoc analysis, *$p<0.05$; $p<0.01$; **$p<0.0001$. biwk=twice a week.
Figure 9:
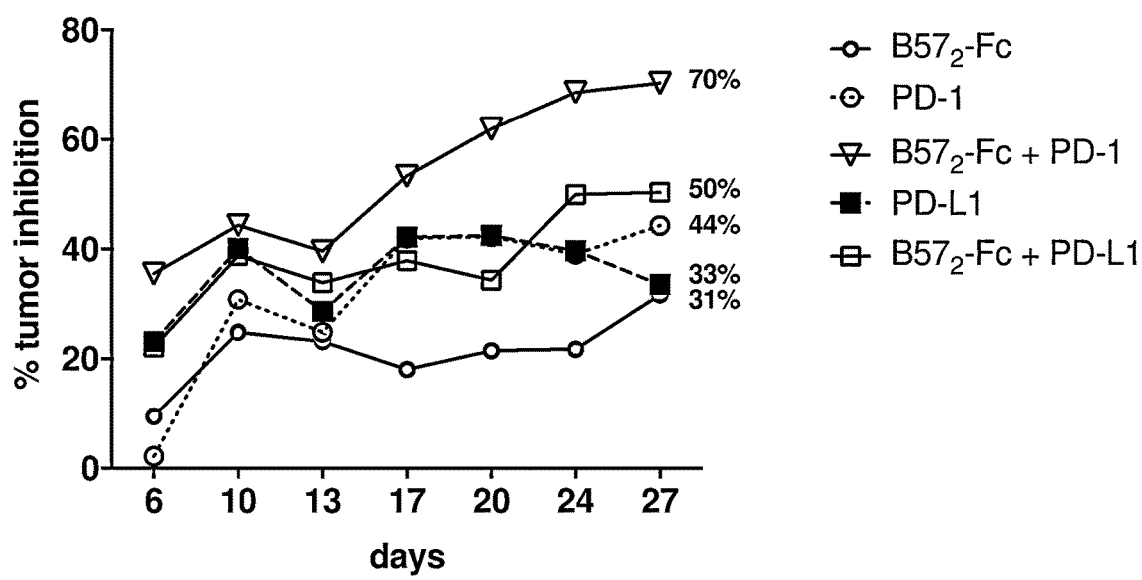
Figure 10:
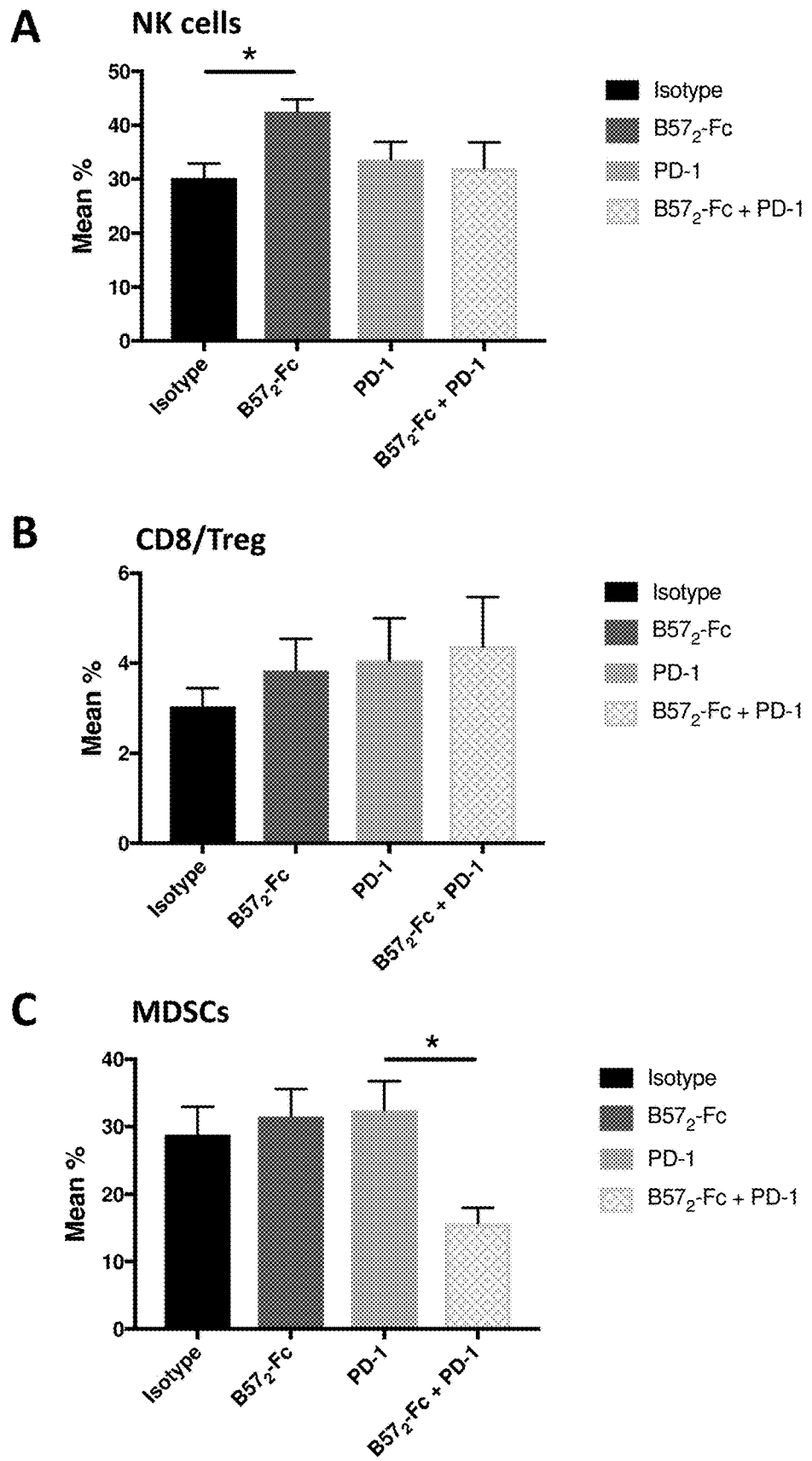
FIG. 10 shows the immune contexture analysis of infiltrated leukocytes in tumors from treated pancreatic (Pan02) cancer mice with B57$_2$-Fc and PD-1 by flow cytometry. Relevant leukocytes analysed infiltrating the tumor: A) NK cells; B) CD8/Treg ratio; and C) Myeloid Derived Suppressor Cells (MDSCs); Leukocytes numbers are expressed as mean±SEM and analysed by one-way ANOVA followed by Turkey post-hoc analysis, *$p<0.05$.
Figure 11:
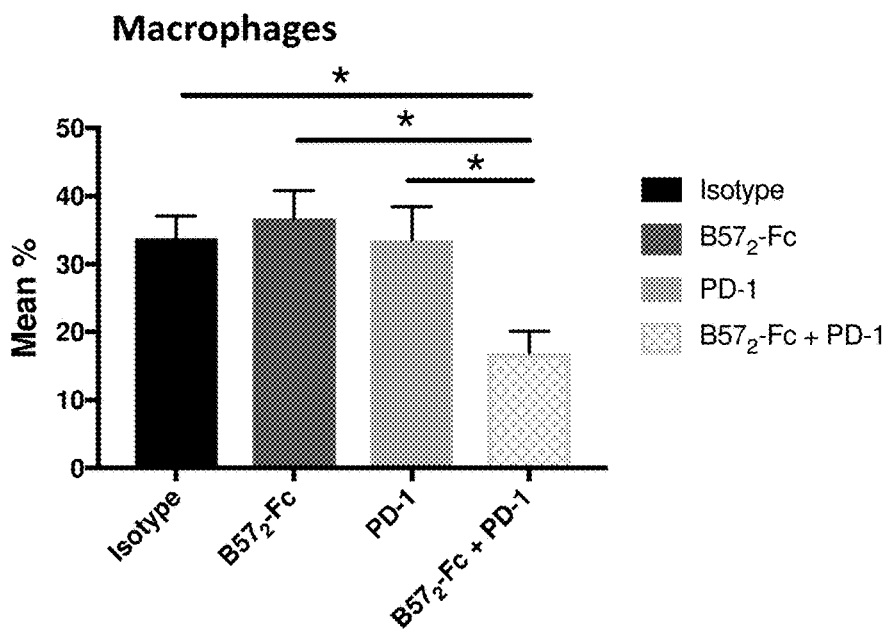
FIG. 11 shows the immune contexture analysis (continuation from FIG. 10) of infiltrated leukocytes in tumors from treated pancreatic (Pan02) cancer mice with B57$_2$-Fc and PD-1 by flow cytometry. Relevant leukocytes analysed infiltrating the tumor: A) Macrophages, and B) Macrophages M1/M2 ratio. Leukocytes numbers are expressed as mean±SEM and analysed by one-way ANOVA followed by Turkey post-hoc analysis, *$p<0.05$; $p<0.01$; *$p<0.001$.
Figure 11:
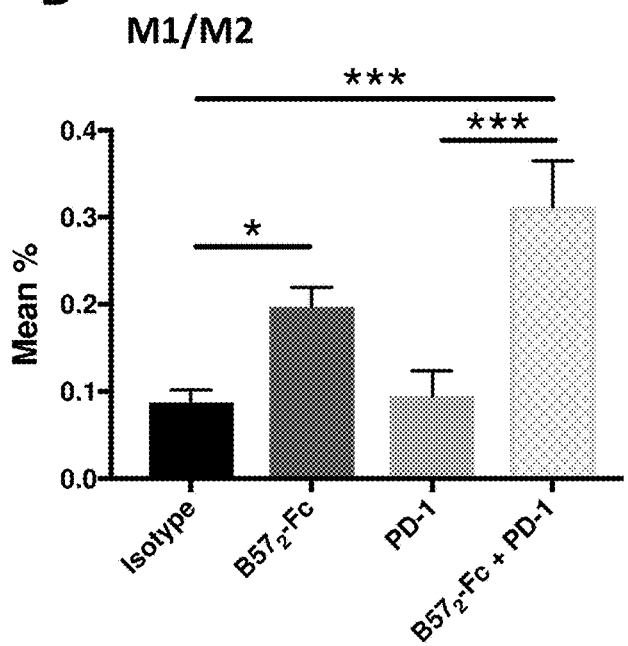
Figure 11:
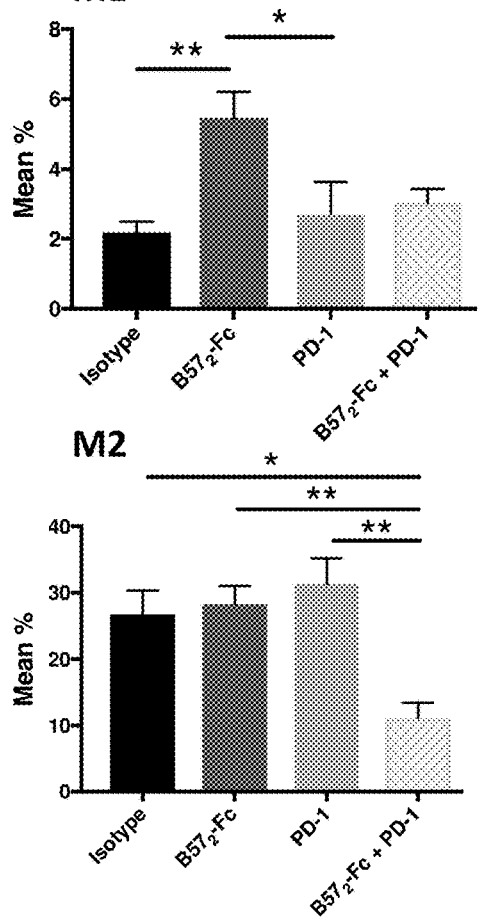
Figure 12:
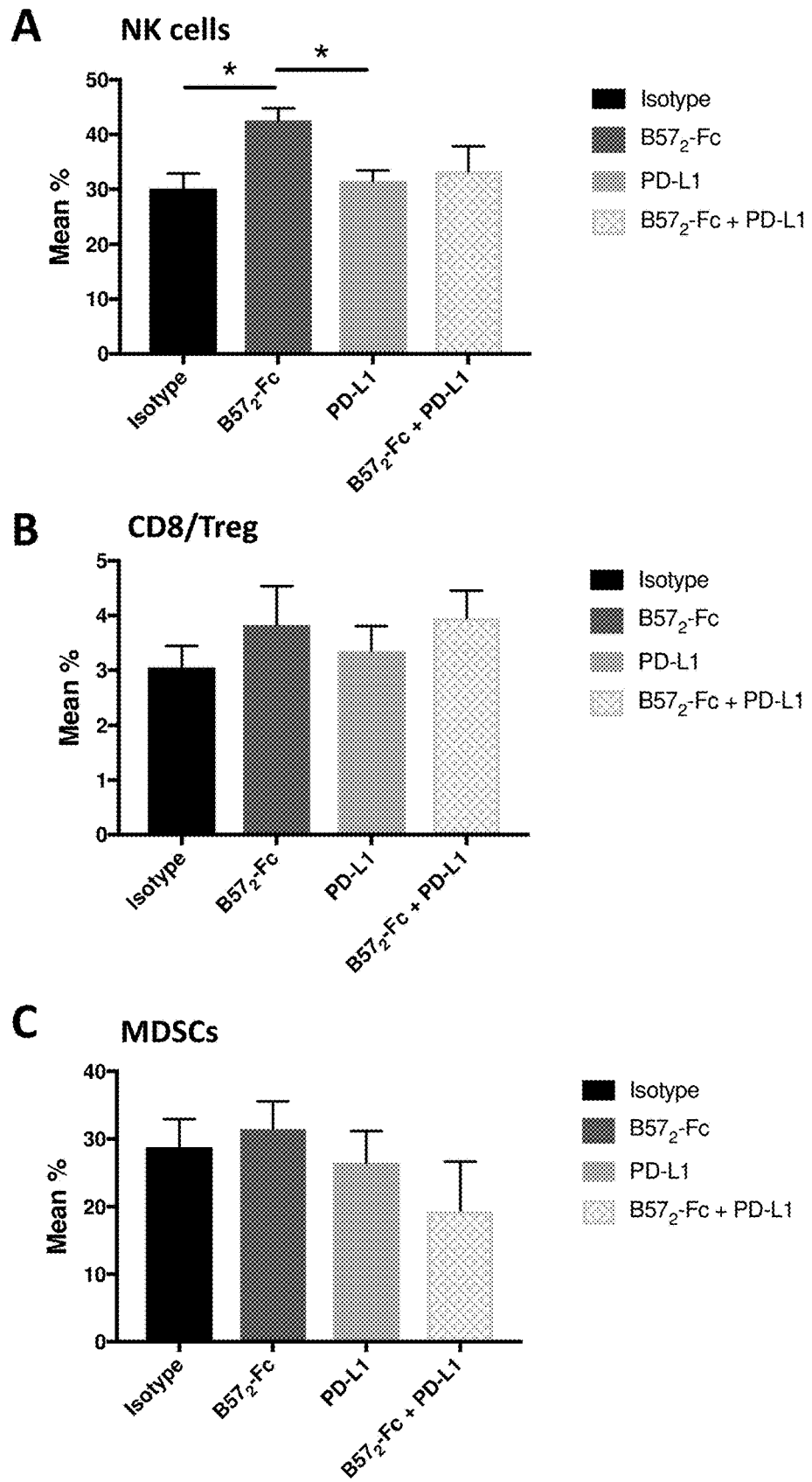
FIG. 12 shows the immune contexture analysis of infiltrated leukocytes in tumors from treated pancreatic (Pan02) cancer mice with B57$_2$-Fc and PD-L1 by flow cytometry. Relevant leukocytes analysed infiltrating the tumor: A) NK cells; B) CD8/Treg ratio; and C) Myeloid Derived Suppressor Cells (MDSCs). Leukocytes numbers are expressed as mean±SEM and analysed by one-way ANOVA followed by Turkey post-hoc analysis, *$p<0.05$.
Figure 13:
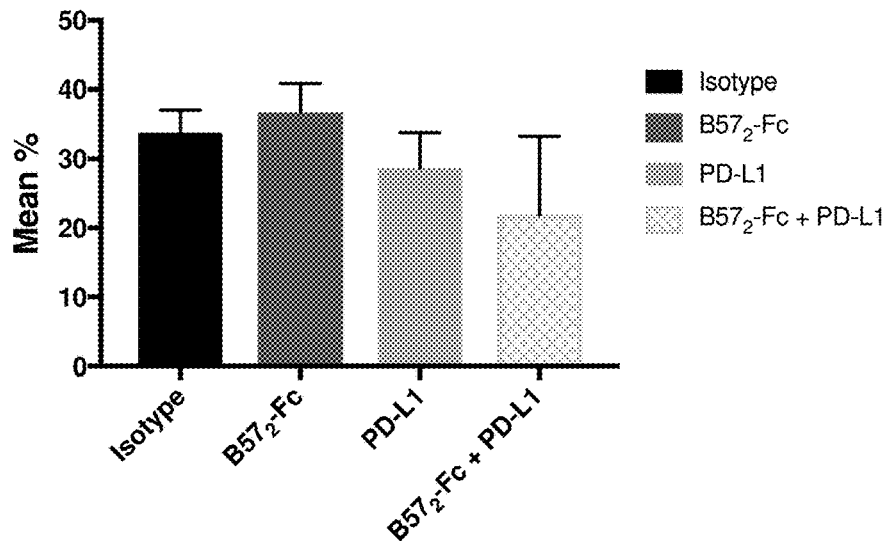
FIG. 13 shows the immune contexture analysis (continuation from FIG. 12) of infiltrated leukocytes in tumors from treated pancreatic (Pan02) cancer mice with B57$_2$-Fc and PD-L1 by flow cytometry. Relevant leukocytes analysed infiltrating the tumor: A) Macrophages, and B) Macrophages M1/M2 ratio. Leukocytes numbers are expressed as mean±SEM and analysed by one-way ANOVA followed by Turkey post-hoc analysis, *$p<0.05$; **$p<0.01$.
Figure 13:
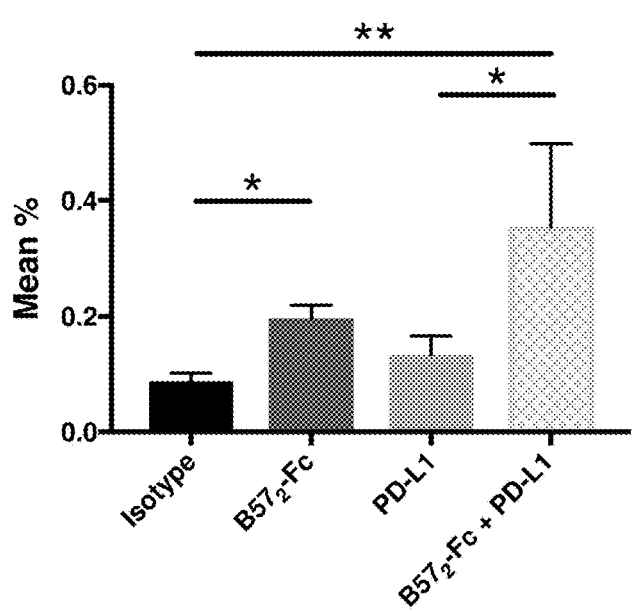
Figure 13:
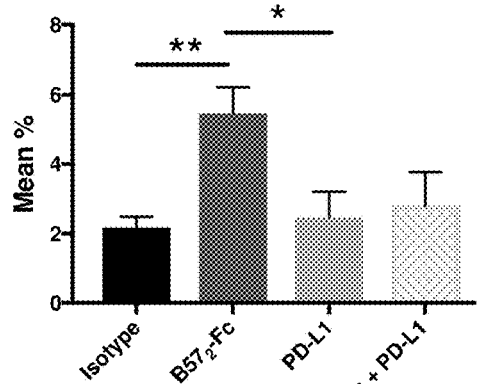
Figure 13:
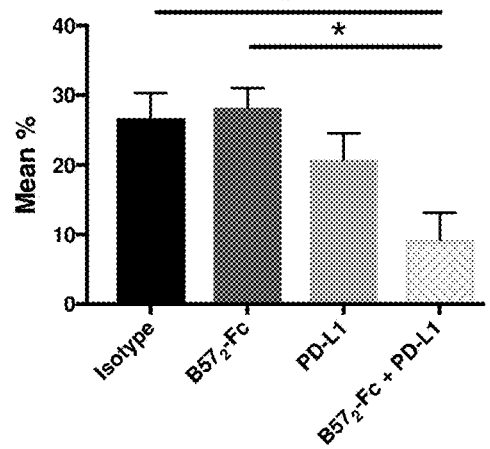

In pancreas (Pan02) data demonstrated that $B57_2$-Fc monotherapy and the combination with PD-1 antibodies can significantly reduce tumors (FIG. 8B, 9B). Combo therapy $B57_2$-Fc+PD-1 vs. isotype control antibody demonstrated a striking significant reduction of tumor volume (216 $mm^3$ vs. 799 $mm^3$, respectively p<0.0001) (FIG. 8B). Additionally, combo therapy $B57_2$-Fc+PD-1 vs. PD-1 monotherapy also showed significant tumor size reduction (216 $mm^3$ vs. 445 $mm^3$, respectively, p<0.01) (FIG. 8B). $B57_2$-Fc monotherapy was significantly different compared to isotype (545 $mm^3$ vs. 799 $mm^3$, respectively, p<0.05). PD-1 monotherapy was significantly different compared to isotype (445 mm$^3$ vs. 799 mm$^3$, respectively p<0.0001) (FIG. 8B).

In pancreas (Pan02) B57$_2$-Fc study in combination with PD-L1 antibodies significantly reduced tumors (FIG. 9A-B). Combo B57$_2$-Fc+PD-L1 vs. isotype showed significant tumor size reduction (397 mm$^3$ vs 799 mm$^3$, respectively, p<0.0001) (FIG. 9A). PD-L1 monotherapy was significantly different compared to isotype (531 mm$^3$ vs 799 mm$^3$, respectively p<0.01) (FIG. 9A).

The tumor immune contexture of pancreas (Pan02) mice demonstrated the influence of B57$_2$-Fc therapy towards diverse sets of tumor infiltrating leukocytes (FIG. 10-13). B57$_2$-Fc monotherapy increased the infiltration of NK cells when compared with control isotype (p<0.05) (FIG. 10A), and significantly modified the Macrophage M1/M2 cell ratio (p<0.05) through favouring the presence of M1 type macrophages within the tumor (FIG. 11B). B57$_2$-Fc combinatorial therapy with PD-1 reduced significantly the infiltration of MDSCs cells in the tumor compared to PD-1 monotherapy (p<0.05) (FIG. 10C), reduced the infiltration of macrophages (FIG. 11A) (p<0.05), and modified significantly the Macrophage M1/M2 ratio when compared to isotype and PD-1 monotherapy (FIG. 11B) (p<0.001). B57$_2$-Fc combinatorial therapy with PD-L1 (FIG. 12-13) modified significantly the Macrophage M1/M2 cell ratio compared to isotype (p<0.01) and PD-L1 (p<0.05) (FIG. 13E).

Figure 14:
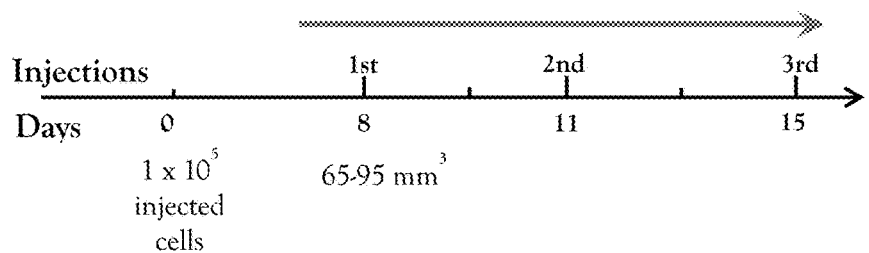
FIG. 14 shows that the combination of B57$_2$-Fc with 4-1BB checkpoint agonist antibodies reduce the size of tumors in the melanoma (B16F10) cancer mouse model. A) Experimental design of injection time points of melanoma cancer cells (B16F10) and injection of compounds. B) Mean average tumor volume mm$^3$ of treated groups (n=8) with B57$_2$-Fc and 4-1BB antibody. The experimental design of injection of substances was as follow: isotype (5 mg/Kg) biwk 3 injections; B57$_2$-Fc (5 mg/Kg) biwk 3 injections; 4-1BB antibody (1 mg/Kg) biwkx3 injections; and B57$_2$-Fc+4-1BB biwk 3 injections. Tumor volumes are expressed as mean±SEM and analysed by two-way ANOVA followed by Bonferroni post-hoc analysis, $p<0.01$; **$p<0.0001$. biwk=twice a week.
Figure 14:
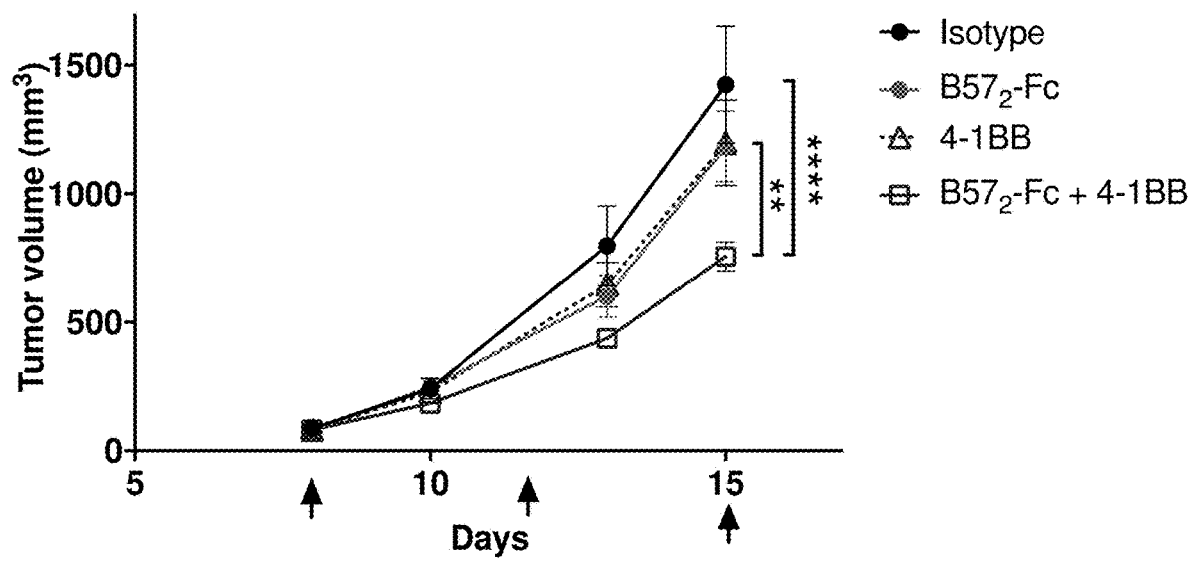
Figure 15:
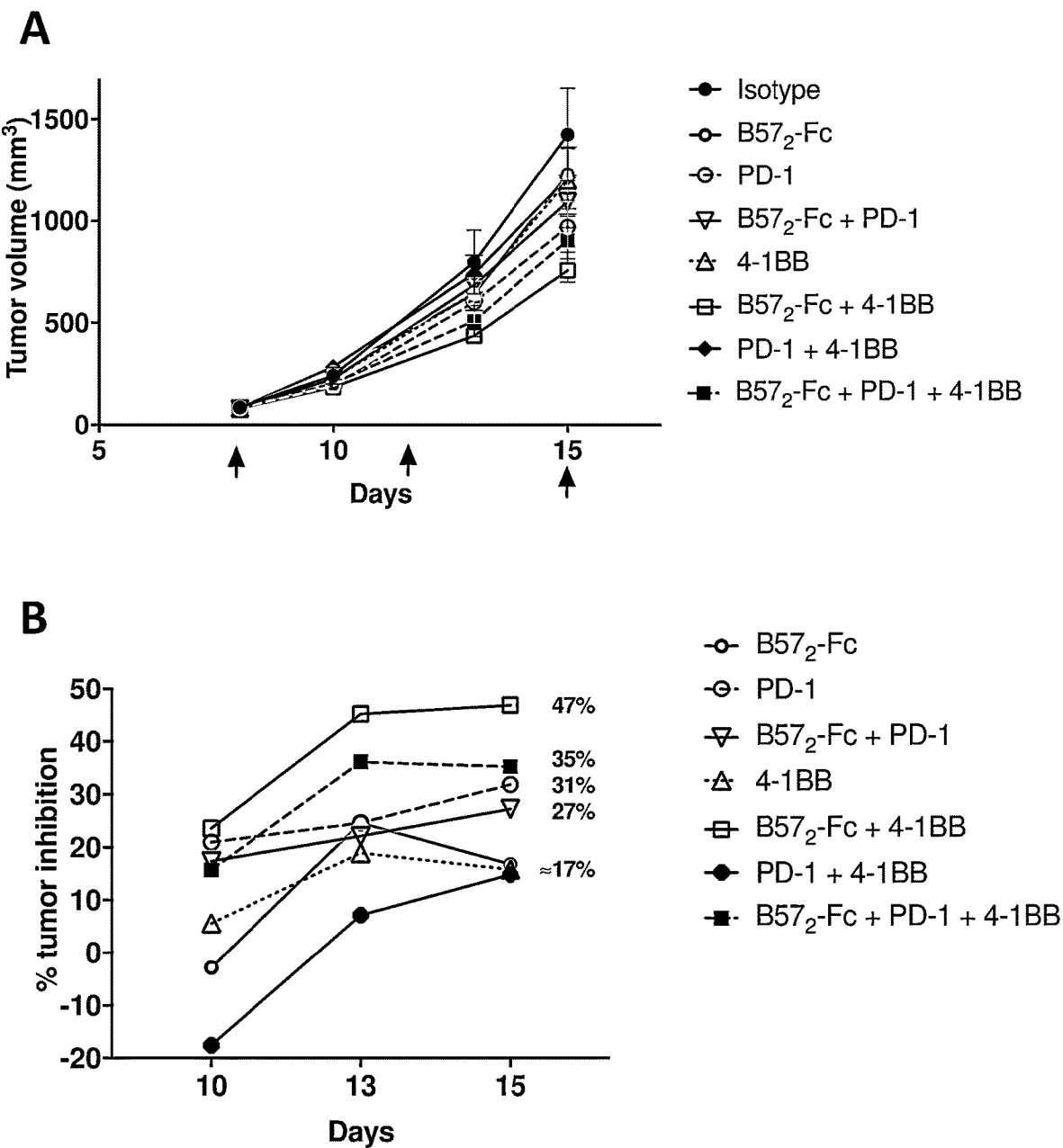
FIG. 15 shows that the combination of B57$_2$-Fc with 4-1BB checkpoint agonist antibodies and combinations with PD-1 antagonist antibodies reduce the size of tumors in the melanoma (B16F10) cancer mouse model (continuation from FIG. 14 experiment). A) Mean average tumor volume mm$^3$ of treated groups (n=8) with B57$_2$-Fc, PD-1 and 4-1 BB antibodies. B) % tumor inhibition of B57$_2$-Fc, 4-1BB and PD-1 treated groups compared to isotype. The experimental design of injection of substances was as follow: isotype (5 mg/Kg) biwk 3 injections; B57$_2$-Fc (5 mg/Kg) biwk 3 injections; 4-1BB antibody (1 mg/Kg) biwk 3 injections; PD-1 biwk 3 injections (5 mg/Kg); and B57$_2$-Fc+4-1 BB biwk 3 injections, B57$_2$-Fc+PD-1 biwk 3 injections, PD-1+4-1 BB biwk 3 injections, and B57$_2$-Fc+4-1 BB+PD-1 biwk 3 injections. Tumor volumes are expressed as mean±SEM. biwk=twice a week.

In melanoma (B16F10) data demonstrated that B57$_2$-Fc in combination with 4-1BB agonist antibodies can significantly reduce tumors (FIG. 14-15). Combo therapy B57$_2$-Fc+4-1BB vs. isotype control antibody showed a striking significant difference on tumor volume reduction (756 mm$^3$ vs. 1424 mm$^3$, respectively p<0.0001) (FIG. 14B). Additionally, combo B57$_2$-Fc+4-1BB vs. 4-1 BB monotherapy showed also significant tumor size reduction (756 mm$^3$ vs. 1199 mm$^3$, respectively, p<0.01) (FIG. 14B). 4-1BB monotherapy was not significantly different compared to isotype (1199 mm$^3$ vs. 1424 mm$^3$, respectively). PD-1 mono and combinatorial therapy did not showed significance between groups (FIG. 15A). However the triple combo therapy (B57$_2$-Fc+4-1BB+PD-1) showed high significant difference compared to isotype (p<0.0001), but was not better than combo B57$_2$-Fc+4-1 BB (FIG. 15A-B).

Figure 16:
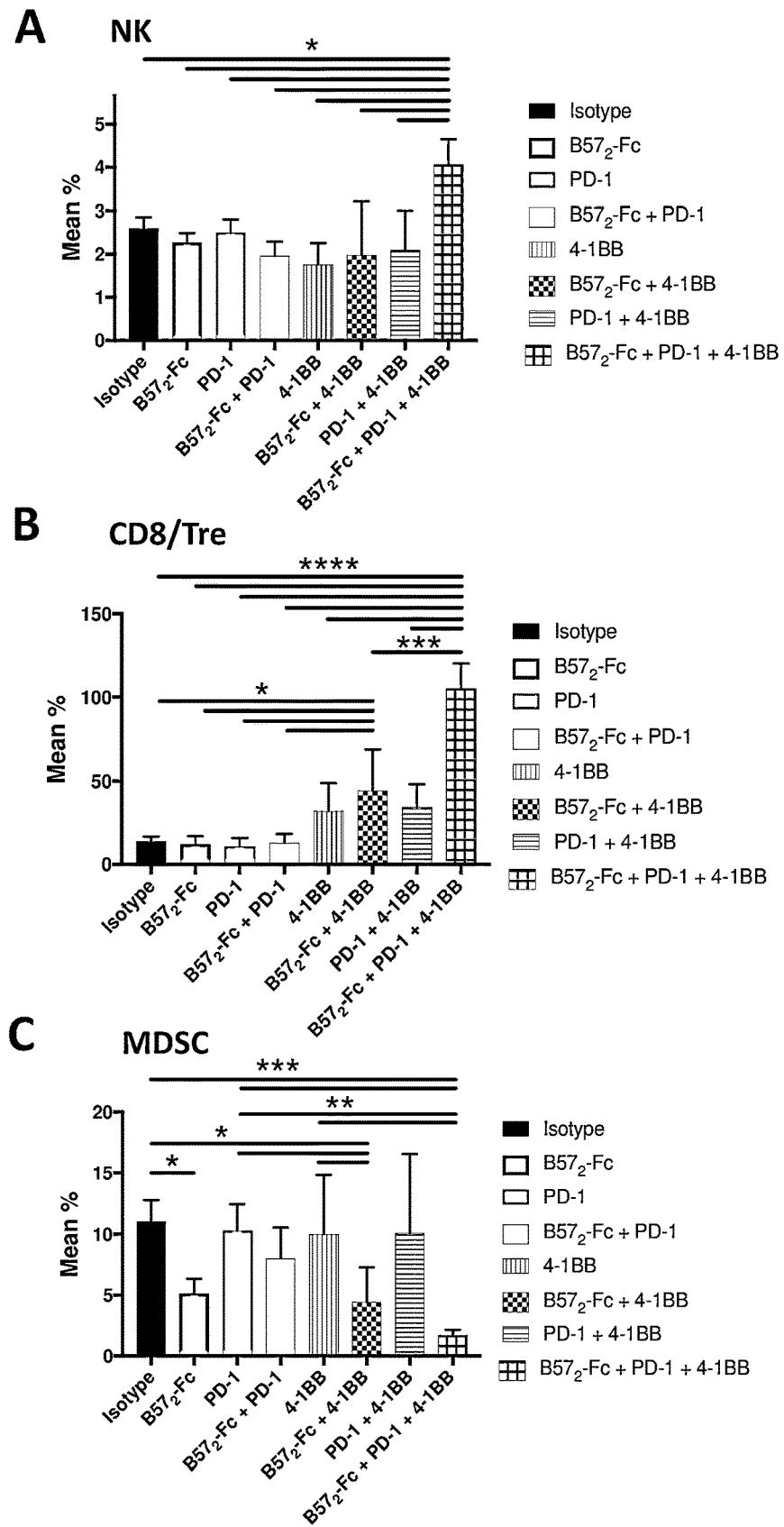
FIG. 16 shows the immune contexture analysis of infiltrated leukocytes in tumors from treated melanoma (B16F10) mice by flow cytometry. Relevant leukocytes analysed infiltrating the tumor: A) NK cells; B) CD8/Treg ratio; and C) Myeloid Derived Suppressor Cells (MDSCs). Leukocytes numbers are expressed as mean±SEM and analysed by one-way ANOVA followed by Turkey post-hoc analysis, *$p<0.05$; $p<0.01$; *$p<0.001$; ****$p<0.0001$.
Figure 17:
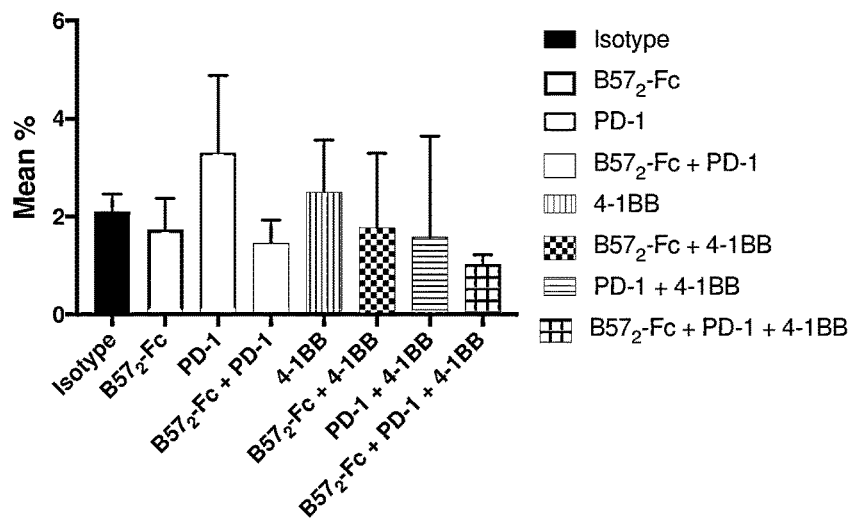
FIG. 17 shows the immune contexture analysis (continuation from FIG. 16) of infiltrated leukocytes in tumors from treated melanoma (B16F10) mice by flow cytometry. Relevant leukocytes analysed infiltrating the tumor: A) Macrophages; and B) Macrophages M1/M2 ratio. Leukocytes numbers are expressed as mean±SEM and analysed by one-way ANOVA followed by Turkey post-hoc analysis, $*p<0.05$; $p<0.01$; $*p<0.001$.
Figure 17:
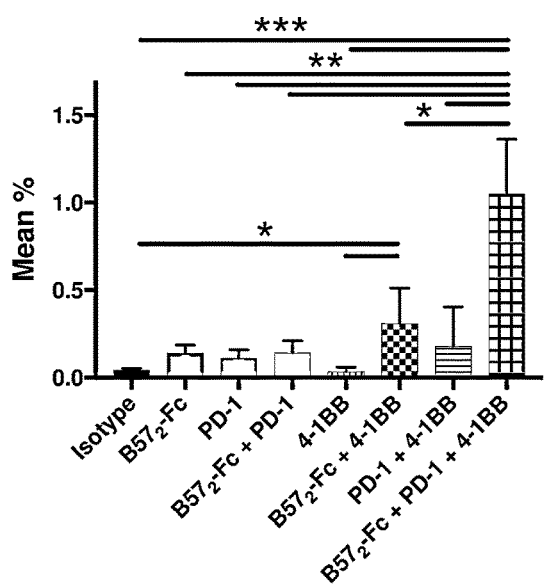
Figure 17:
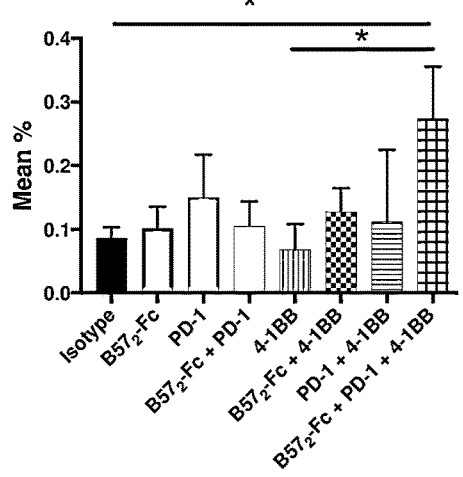
Figure 17:
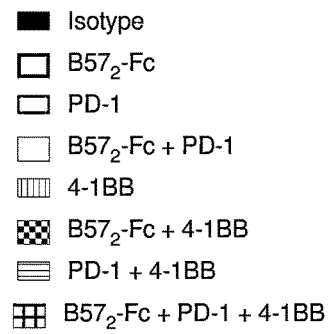
Figure 17:
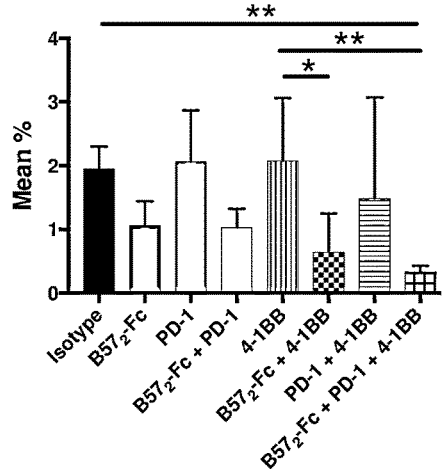

The tumor immune contexture of melanoma (B16F10) treated animals demonstrated the influence of B57$_2$-Fc therapy with diverse sets of tumor infiltrating leukocytes (FIG. 16-17). B57$_2$-Fc monotherapy reduced significantly the presence of MDSCs cells inside the tumor when compared to isotype (p<0.05) (FIG. 16C). B57$_2$-Fc combinatorial therapy with 4-1BB antibodies modified significantly the presence of CD8+ T-cells vs Treg cells as measured through the ratio of CD8+ Tcell/Treg (p<0.05) (FIG. 16B), reduced significantly the presence of MDSCs cells inside the tumor (p<0.05) (FIG. 16C), and modified significantly the Macrophage M1/M2 cell ratio when compared to isotype and 4-1BB monotherapy (p<0.05) (FIG. 17B). B57$_2$-Fc triple combinatorial therapy with 4-1BB and PD-1 antibodies induced significantly the infiltration of NK cells into the tumor (p<0.05) (FIG. 16A), strikingly modified the CD8+ Tcell/Treg ratio compared to isotype (158% vs. 23%, respectively, p<0.0001), and also compared to all other groups (FIG. 16B). Furthermore, reduced significantly the presence of MDSCs cells inside the tumor (p<0.001) (FIG. 16C), and modified significantly the Macrophage M1/M2 cell ratio when compared to all the other groups (FIG. 17B).

Conclusion

The proof of principle for using B57$_2$-Fc molecules to fight cancer was demonstrated using pre-clinical syngeneic mouse models of colon, pancreas and melanoma. The present data demonstrates the therapeutic potential of B57$_2$-Fc as either monotherapy and/or combinatorial therapy with sets of checkpoint inhibitory agents and/or checkpoint agonist agents such as PD-1, PD-L1 or 4-1BB antibodies.

The mode of action of B57$_2$-Fc was also assessed in vivo in pancreas and melanoma mouse models by establishing the tumor infiltration of leukocytes. B57$_2$-Fc therapy can regulate the infiltration of diverse sets of leukocytes into the tumors of mice as determined by the increased ratio of Macrophages M1/M2 cells, reduced infiltration of MDSCs, increased infiltration ratio of CD8+ T cells/Treg ratio, and increased infiltration of NK cells. Overall, the mode of action of B57$_2$-Fc alone or in a combinatorial approach with antagonistic/agonistic antibodies is of undoubted relevance in the treatment of cancer, and correlates to the current clinical need in cancer immunotherapy.

B57$_2$-Fc emerges as a novel class of immunomodulatory drug. In vitro and in vivo data points to a mechanism were B57$_2$-Fc molecules act as a switch-on mechanism for the activation of anti-tumor immunity. Without wishing to be bound by theory, the inventors hypothesize that the interaction of HLA-B57 open conformers bind to diverse immunomodulatory receptors present in myeloid cells (Macrophages, MDSCs), T cells and NK cells participate synergistically and exacerbate the immune response.

Materials and Methods

Animals and Cell Lines

In vivo experiments were conducted in C57Bl/6 mice using the mouse derived colon carcinoma C38 cell line, the pancreatic ductal adenocarcinoma Pan02 mouse cell line; and melanoma B16F10 mouse cell line.

In vitro experiment cell lines: EG.7, mouse T cell lymphoma; Jurkat, human T cell lymphoma; L428, human Hodgkin lymphoma; L540, human Hodgkin lymphoma; L1236, human Hodgkin lymphoma; Daudi, B cell lymphoma; IMR-5, neuroblastoma; SK-N-AS, neuroblastoma; and M130428, Melanoma.

In Vivo Treatments

C38 tumour fragments were injected subcutaneously into the right flanks of syngeneic female C57BL/6 mice at week 6. Pan02 and B16F10 cell lines were injected at 1×10$^5$ in the right flank of syngeneic mice at week 6. Once the tumour reached ±80 mm$^3$ in colon (C38), pancreas (Pan02) and melanoma (B16F10), animals were distributed according to their individual tumour volume size and divided into groups displaying no statistical differences between them. Tumour diameters were measured using a caliper, and volume was calculated according to the formula, D/2×d$^2$ where D and d are the longest and shortest diameter of the tumour in mm, respectively.

The Experimental design of injection time points of cells and injection of substances was established as follows for colon (C38) vehicle (PBS 200 μL); isotype (10 mg/Kg) Q3Dx7; B57$_2$-Fc (10 mg/Kg); PD-1 biwkx2 (200 μg); B57$_2$-Fc+PD-1 (Q3Dx7 and biwkx2, respectively), B27$_2$-Fc+PD-1 (Q3Dx7 and biwkx2, respectively). For pancreas (Pan02) the experimental design of injection of substances was as follow: isotype (5 mg/Kg) biwkx3; B57$_2$-Fc (5 mg/Kg) biwkx3; PD-1 biwkx3 (5 mg/Kg); PD-L1 biwkx3 (5 mg/Kg); B57$_2$-Fc+PD-1 (biwkx3) and B57$_2$-Fc+PD-L1 (biwkx3). For melanoma (B16F10) the experimental design of injection of substances was as follow: isotype (5 mg/Kg) biwk 3 injections; B57$_2$-Fc (5 mg/Kg) biwk 3 injections; 4-1 BB antibody (1 mg/Kg) biwk 3 injections; PD-1 biwk 3 injections (5 mg/Kg); B57$_2$-Fc+4-1 BB biwk 3 injections, B57$_2$-Fc+PD-1 biwk 3 injections, PD-1+4-1 BB biwk 3 injections, and B57$_2$-Fc+4-1 BB+PD-1 biwk 3 injections.

Preparation of tumor samples for flow cytometry were performed using protocols described by eBioscience (https://www.ebioscience.com/media/pdf/best-protocols/cell-preparation-for-flow-cytometry.pdf, accessed Feb. 21, 2017).

Antibodies

Leukocytes mouse populations for in vitro tests were stained with: CD3 (PE-Cy7-eBioscience), CD4 (FITC-BD Bioscience), FoxP3+ (efluor 450-eBioscience), CD45 (PerCP-eBioscience), CD3 (PE-eBioscience), NK1.1 (BV421-eBioscience), CD11b (FITC-eBioscience), CD11c (FITC-eBioscience), CD25 (PE-Cy7-Biolegend).

HC10 mAb (IgG2a) binding to β2m-free heavy chains of HLA-B and -C alleles and so to B57$_2$ was a gift from Dr. Hidde Ploegh (MIT, MA).

Flow cytometry antibodies from tumor samples were stained with: CD45 (FITC; clone 30-F11; Biolegend), CD3 (PerCP/Cy5.5; clone 17A2; Biolegend), CD4 (BV510; clone GK1.5; Biolegend), CD8 (APC-H7; clone 53-6.7; BD), FoxP3 (PE; clone FJK-16S; eBioscence), CD11b (BV650; clone M1/70; Biolegend), F4/80 (PE/Cy7; clone BM8; Biolegend), Gr-1 (APC-R700; clone RB6-8C5; BD), NK1.1 (BV605; clone PK136; Biolegend), CD206 (APC; clone C068C2; Biolegend), CD86 (BV421; clone GL-1; Biolegend), L/D stain (BUV395; Invitrogen).

Checkpoint inhibitor antibody anti-mouse PD-1 clone RMP1-14 was obtained from Bio X Cell. Checkpoint inhibitor antibody anti-mouse PD-L1 clone: 10F.9G2 was obtained from Bio X Cell. Agonistic antibody anti-mouse 4-1 BB clone 3H3 was obtained from Bio X Cell.

Flow Cytometry of Leukocytes

Flow cytometry analysis was performed using a FACS canto II (BD Bioscience) and data were analysed using FlowJo version 7.6.4.

Generation of Tregs

To induce expression of Foxp3 in murine CD4$^+$ T cells, we harvested spleen cells from C57BL/6 splenocytes and purified ((Mouse Naïve CD4$^+$ T Cell Isolation Kit—Easy Sep) to obtain CD4$^+$ T naive cells. Cells were then cultured for 96 h at 10$^5$ cells/200 µL/well in 96-well plates with coated 5 µg/mL anti-CD3mAb (eBioscience), soluble 2 µg/mL anti-CD28 mAb (Biolegend), 10 µg/mL of TGF-β1 (R&D systems) and 100 IU/mL of IL-2 (R&D systems).

iTreg Conversion in the Presence of B57$_2$-Fc

Murine naive CD4$^+$ T cells in optimal culture conditions for iTreg conversion were incubated in the presence of different dose concentrations (µg/200 µL) of B57$_2$-Fc, B57-β2m-Fc, B27-β2m-Fc, Isotype IgG4 and PBS for 72 h. iTreg conversion was measured by flow cytometry.

Suppression Assay

CD4$^+$ or CD8$^+$ T-effector cells were purified PBMCs from either mouse or human (Mouse Naïve CD4$^+$ T Cell Isolation Kit—Easy Sep; Dynabeads® FlowComp™ Mouse CD8—life technologies; Dynabeads® CD8 human—Life Technologies) and labelled with 10 µM cell trace violet proliferation stain (Molecular Probes). Tregs (2.5×10$^4$) cells and T-effector cells (2.5×10$^4$) were cultured in 96 wells U-bottomed plates with coated CD3 (eBioscience) (3 µg/mL) and soluble CD28 (eBioscience) (1 µg/mL) antibody for 96 hrs. Proliferation of T-effector cells was measured using a FACS canto II and data were analysed using proliferation analysis software from FlowJo version 7.6.4.

Proliferation Assay

Cells were plated in round 96-wells plates at a density of 5×10$^5$ cells/well following the addition of drugs at different concentrations (10, 5, and 2 µg/well) for 1 day. XTT proliferation assay was performed accordingly to the manual instructions (cell proliferation kit II, Roche). Results were obtained with the absorbance of wells at 450 nm using a microtiter plate reader.

ELISA Assays

Competition ELISA assays were performed using Maxisorp (Nunc, Switzerland) 96 well plates coated with 10 µg/mL of selected recombinant leukocyte receptors (human KIR3DL1, human KIR3DL2, human KIR3DL3, human LILRB1, human LILRB2, and mouse Pirb). Receptors were incubated for ON 4° C., blocked with 5% milk powder-PBS 2 hrs. B57$_2$-Fc, B57-β2m-Fc, B27$_2$-Fc, B27-β2m-Fc, and isotype IgG4 were added at 2 µg/mL for 2 hrs RT. HRP-conjugated antibodies against human Fc were used as detectors.

Production, Purification and Re-Folding of B57$_2$-Fc

Recombinant production of B57-β2m-Fc was achieved by inserting the alpha 1, 2 and 3 domains of HLA-B57 into a human IgG4-Fc vector, and the human β2-microglobulin (β2m) in a separate vector. Production of recombinant B57-β2m-Fc was performed by co-transfection of B57-Fc-vector and β2m-vector into Chinese hamster ovary (CHO) cells. Production of B57-β2m-Fc was outsourced to Evitria AG.

Purification of B57-β2m-Fc was performed using conventional protocols for antibody purification. Production of B57$_2$-Fc was performed with the addition of a denaturing step to remove β2m from the B57-β2m-Fc complex.

Briefly, the capture step of B57-β2m-Fc was performed after running supernatants (5 mL/min) through protein-G columns (Amersham Pharmacia). Intermediate purification steps were performed by eluting the B57-β2m-Fc from protein G-columns using elution buffer (100 mM glycine, pH 2.0), and recovering fractions in 8M Urea, 100 mM Tris-HCl pH 8.0. The 1$^{st}$ Polishing step was to separate B57-Fc monomers fractions from β2m by either size exclusion chromatography (SEC) using superdex 200 prep grade or Sephacryl S-100 HR (GE Lifescience) with an ÄKTA system (GE Lifescience), or by dialysis with membranes of 30 KDa or 50 KDa pore size (Millipore). The recovered B57-Fc monomers from both protocols were re-folded by the dilution method after pulsation of the B57-Fc monomers at 3 times with intervals of 8 hours each in 100 times volume of refolding buffer (50 mM Tris-HCl pH 8.5, 500 mM L-Arginine, 1 mM EDTA, 0.15 mM NaCl, 1% Sucrose, 0.01% Tween-20). The 2$^{nd}$ Polishing step by SEC was performed to remove further impurities and to buffer exchange newly recovered fractions of B57$_2$-Fc molecules into dilution buffer (PBS, 1% Sucrose, and 0.01% Tween-20). Purified solutions of B57$_2$-Fc were filter sterilized using 0.2 µm membranes (Millipore).

Fractions B57-β2m-Fc complexes and B57$_2$-Fc were analysed by SDS polyacrylamide gel electrophoresis (SDS-PAGE) and western blot using HC10 (specific for HLA-free-heavy chains) antibodies. β2m western blots were performed with and without denaturing conditions (10 mM DTT) (data not shown).

Full and Partial Sequences of HLA-B57 Alleles

Functional domains of the full length HLA-B57 alpha chain from N-terminus to C-terminus are: Signal peptide, alpha 1, alpha 2, alpha 3, transmembrane domain and cytoplasmic tail.

TABLE 1

| HLA-B57 alleles | |
|---|---|
| Sequence identifier (length in aa) | Amino acid sequence |
| B*57:01:01 HLA00381 (362 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQVMYGCDVGPDGRLLRGHDQSAYDGKDYIALNEDLSSWTAADT AAQITQRKWEAARVAEQLRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA (SEQ ID 001) |
| B*57:01:02 HLA01520 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 002) |
| B*57:01:03 HLA02259 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 003) |
| B*57:01:04 HLA03969 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 004) |
| B*57:01:05 HLA04060 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 005) |
| B*57:01:06 HLA04456 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 006) |
| B*57:01:07 HLA04755 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKPLT LRW (SEQ ID 007) |
| B*57:01:08 HLA05320 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 008) |
| B*57:01:09 HLA05465 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 009) |
| B*57:01:10 HLA05563 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 010) |
| B*57:01:11 HLA06363 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKPLT LRW (SEQ ID 011) |
| B*57:01:12 HLA07200 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 012) |
| B*57:01:13 HLA07801 (362 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQVMYGCDVGPDGRLLRGHDQSAYDGKDYIALNEDLSSWTAADT AAQITQRKWEAARVAEQLRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA (SEQ ID 013) |

TABLE 1-continued

HLA-B57 alleles

| Sequence identifier (length in aa) | Amino acid sequence |
|---|---|
| B*57:01:14 HLA08370 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 014) |
| B*57:01:15 HLA09723 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 015) |
| B*57:01:16 HLA10039 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 016) |
| B*57:01:17 HLA10498 (337 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQVMYGCDVGPDGRLLRGHDQSAYDGKDYIALNEDLSSWTAADT AAQITQRKWEAARVAEQLRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPKPLTRWEPSSQSTVPIVGIVAGLAVLAVVVIG AVVAAVMCRRKSS (SEQ ID 017) |
| B*57:01:18 HLA11430 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 018) |
| B*57:01:19 HLA11726 (298 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQVMYGCDVGPDGRLLRGHDQSAYDGKDYIALNEDLSSWTAADT AAQITQRKWEAARVAEQLRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPKPLTRW (SEQ ID 019) |
| B*57:01:20 HLA12568 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 020) |
| B*57:01:21 HLA12884 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKPLT LRW (SEQ ID 021) |
| B*57:01:22 HLA13005 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 022) |
| B*57:02:01 HLA00382 (362 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQVMYGCDVGPDGRLLRGHNQYAYDGKDYIALNEDLSSWTAADT AAQITQRKWEAARVAEQRRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPKPLTRWEPSSQSTVPIVGIVAGLAVLAVVVIG AVVAAVMCRRKSSGGKGGSYSQAACSDSAQGSDVSLTA (SEQ ID 023) |
| B*57:02:02 HLA04435 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAARVAEQRRAYLEGL CVEWLRRYLENGKETLQRA (SEQ ID 024) |
| B*57:03:01 HLA00383 (362 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQVMYGCDVGPDGRLLRGHNQYAYDGKDYIALNEDLSSWTAADT AAQITQRKWEAARVAEQLRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPKPLTRWEPSSQSTVPIVGIVAGLAVLAVVVIG AVVAAVMCRRKSSGGKGGSYSQAACSDSAQGSDVSLTA (SEQ ID 025) |

TABLE 1-continued

HLA-B57 alleles

| Sequence identifier (length in aa) | Amino acid sequence |
|---|---|
| B*57:03:02 HLA01289 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAARVAEQLRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKPLT LRW (SEQ ID 026) |
| B*57:04:01 HLA00384 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGYDQDAYDGKDYIALNEDLSSWTAADTAAQITQRKWEAARVAEQRRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKPLT LRW (SEQ ID 027) |
| B*57:04:02 HLA14153 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGYDQDAYDGKDYIALNEDLSSWTAADTAAQITQRKWEAARVAEQRRAYLEGL CVEWLRRYLENGKETLQRA (SEQ ID 028) |
| B*57:05 HLA00385 (362 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQRMYGCDLGPDGRLLRGYNQYAYDGKDYIALNEDLSSWTAADT AAQITQRKWEAARVAEQRRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA (SEQ ID 029) |
| B*57:06 HLA01074 (362 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQVMYGCDVGPDGRLLRGHDQSAYDGKDYIALNEDLSSWTAADT AAQIIQRKWEAARVAEQLRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA (SEQ ID 030) |
| B*57:07 HLA01192 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAARVAEQLRAYLEGL CVESLRRYLENGKETLQRA (SEQ ID 031) |
| B*57:08 HLA01461 (181 aa) | SHSMRYFYTAMSRPGRGEPRFIAVGYVDDTQFVRFDSDAASPRMAPRAPWIEQE GPEYWDGETRNMKASAQTYRENLRIALPYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 032) |
| B*57:09 HLA01485 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAAREAEQDRAYLEGL CVEWLRRYLENGKETLQRA (SEQ ID 033) |
| B*57:10 HLA02307 (181 aa) | SHSMRYFYTSVSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 034) |
| B*57:11 HLA02676 (362 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHTLQWMYGCDVGPDGRLLRGHDQSAYDGKDYIALNEDLSSWTAADT AAQITQRKWEAARVAEQLRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA (SEQ ID 035) |
| B*57:12 HLA02888 (181 aa) | SHSMRYFYTAMSRPGRGEPRFIAVGYVDDTQFVRFDSDAASPRMAPRAPWIEQE GPEYWDGETRNMKASAQTYRESLRNLRGYYNQSEAGSHIIQVMYGCDVGPDGRL LRGHNQYAYDGKDYIALNEDLSSWTAADTAAQITQRKWEAARVAEQRRAYLEGL CVEWLRRYLENGKETLQRA (SEQ ID 036) |
| B*57:13 HLA02966 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLRSWTAADTAAQITQRKWEAAREAEQRRAYLEGE CVEWLRRYLENGKETLQRA (SEQ ID 037) |

TABLE 1-continued

HLA-B57 alleles

| Sequence identifier (length in aa) | Amino acid sequence |
|---|---|
| B*57:14:01 HLA03129 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRHLENGKETLQRA (SEQ ID 038) |
| B*57:14:02 HLA12293 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRHLENGKETLQRA (SEQ ID 039) |
| B*57:15 HLA03147 (181 aa) | SHSMRYFYTAMSRPGRGEPRFIAVGYVDDTQFVRFDSDAASPRMAPRAPWIEQE GPEYWDGETRNVKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 040) |
| B*57:16 HLA03150 (181 aa) | SHSMRYFYTAMSRPGRGEPRFIAVGYVDDTQFVRFDSDAASPRMEPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 041) |
| B*57:17 HLA03320 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIDLNEDLSSWTAADTAAQITQRKWEAARVAEQLRAYLEGL CVEWLRRYLENGKETLQRA (SEQ ID 042) |
| B*57:18 HLA03506 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAAYTAAQITQRKWEAARVAEQLRAYLEGL CVEWLRRYLENGKETLQRA (SEQ ID 043) |
| B*57:19 HLA03507 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQRRAYLEGL CVEWLRRYLENGKETLQRA (SEQ ID 044) |
| B*57:20 HLA03666 (181 aa) | SHSMRYFYTAMSRPGRGEPRFIAVGYVDDTQFVRFDSDAASPRMAPRAPWIEQE GPEYWDGKTRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 045) |
| B*57:21 HLA03675 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHVIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 046) |
| B*57:22 HLA03904 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAAREAEQLRAYLEGL CVEWLRRYLENGKETLQRA (SEQ ID 047) |
| B*57:23 HLA04046 (181 aa) | SHSMRYFYTAMSRPGRGESRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 048) |
| B*57:24 HLA03984 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQDRAYLEGL CVEWLRRYLENGKETLQRA (SEQ ID 049) |
| B*57:25 HLA03986 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGE CVEWLRRYLENGKETLQRA (SEQ ID 050) |
| B*57:26 HLA04203 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGT CVEWLRRYLENGKETLQRA (SEQ ID 051) |
| B*57:27 HLA04452 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEHLRAYLEGL CVEWLRRYLENGKETLQRA (SEQ ID 052) |

TABLE 1-continued

HLA-B57 alleles

| Sequence identifier (length in aa) | Amino acid sequence |
|---|---|
| B*57:28N HLA04401 (115 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQX (SEQ ID 053) |
| B*57:29 HLA04576 (362 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQVMYGCDVGPDGRLLRGHDQSAYDGKDYIALNEDLSSWTAADT AAQITQRKWEAARVAEQLRAYLEGLCVEWLRRYLENGKETLQRADPPKTHVTHH PISDHEATLRCWALGFYPVEITLTWQRDGEDQTQDTELVETRPAGDRTFQKWAA VVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA (SEQ ID 054) |
| B*57:30 HLA04703 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARAAEQRRAYLEGL CVEWLRRYLENGKETLQRA (SEQ ID 055) |
| B*57:31 HLA04848 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLRSWTAADTAAQITQRKWEAARVAEQLRAYLEGL CVEWLRRYLENGKETLQRA (SEQ ID 056) |
| B*57:32 HLA05424 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGYHQDAYDGKDYIALNEDLSSWTAADTAAQITQRKWEAARVAEQLRAYLEGL CVEWLRRYLENGKETLQRA (SEQ ID 057) |
| B*57:33 HLA05476 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDERL LRGHDQSAYDGKDYIALNEDLSSWTAADTAAQITQRKWEAARVAEQLRAYLEGL CVEWLRRYLENGKETLQRA (SEQ ID 058) |
| B*57:34 HLA05503 (181 aa) | SHSMRYFYTAMSRPGRGEPRFIAVGYVDDTQFVRFDSDAASRRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 059) |
| B*57:35 HLA05513 (181 aa) | SHSMRYFYTAMSRPGRGEPRFIAVGYVDDTQFVRFDSDAASPRMAPRAPWIEQE GPKYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 060) |
| B*57:36 HLA05562 (181 aa) | SHSMRYFYTAMSRPGRGEPRFIAVGYVDDTQFVRFDSDAASPRMAPRAPWIEQE GPEYWDGETRHMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 061) |
| B*57:37 HLA05876 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKHLT LRW (SEQ ID 062) |
| B*57:38 HLA05958 (181 aa) | SHSMRYFYTAMSRPGRGEPRFIAVGYVDDTQFVRFDSDAASPRMAPRAPWIEQE GPEYWDGETRNMKASAQTYRETLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 063) |
| B*57:39 HLA06229 (181 aa) | SHSMRYFHTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAARVAEQLRAYLEGL CVEWLRRYLENGKETLQRA (SEQ ID 064) |
| B*57:40 HLA06240 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHNIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 065) |
| B*57:41 HLA06241 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGYDQSAYDGKDYIALNEDLSSWTAADTAAQITQRKWEAARVAEQLRAYLEGL CVEWLRRYLENGKETLQRA (SEQ ID 066) |

TABLE 1-continued

HLA-B57 alleles

| Sequence identifier (length in aa) | Amino acid sequence |
|---|---|
| B*57:42 HLA06249 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEEARVAEQRRAYLEGL CVEWLRRYLENGKETLQRA (SEQ ID 067) |
| B*57:43 HLA06250 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGP CVEWLRRYLENGKETLQRA (SEQ ID 068) |
| B*57:44 HLA06315 (181 aa) | SHSMRYFYTAMSRPGLGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 069) |
| B*57:45 HLA06683 (181 aa) | SHSMRYFYTAMSRPGRGEPRFIAVGYVDDTQFVRFDSDATSPRKEPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 070) |
| B*57:46 HLA06688 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAACVAEQLRAYLEGL CVEWLRRYLENGKETLQRA (SEQ ID 071) |
| B*57:47 HLA06700 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSCWTAADTAAQITQRKWEAARVAEQLRAYLEGL CVEWLRRYLENGKETLQRA (SEQ ID 072) |
| B*57:48 HLA06883 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGPL LRGHDQSAYDGKDYIALNEDLSSWTAADTAAQITQRKWEAARVAEQLRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKPLT LRW (SEQ ID 073) |
| B*57:49 HLA06942 (181 aa) | SHSMRYFDTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 074) |
| B*57:50 HLA06949 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQGKWEAARVAEQLRAYLEGL CVEWLRRYLENGKETLQRA (SEQ ID 075) |
| B*57:51 HLA06974 (181 aa) | SHSMRYFHTAMSRPGRGEPRFITVGYVDDTLFVRFDSDATSPRKEPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 076) |
| B*57:52 HLA06989 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRASLEGL CVEWLRRYLENGKETLQRA (SEQ ID 077) |
| B*57:53 HLA07455 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSTYDGKDYIALNEDLSSWTAADTAAQITQRKWEAARVAEQLRAYLEGL CVEWLRRYLENGKETLQRA (SEQ ID 078) |
| B*57:54 HLA07456 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADKAAQITQRKWEAARVAEQLRAYLEGL CVEWLRRYLENGKETLQRA (SEQ ID 079) |
| B*57:55 HLA07545 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRADPPKTHVTHHPISDHEATLRCWALGFYPAEITLTW QRDGEDQTQDTKLVETRPAGDRTFQKWAAVVVPSGEEQRYTCHVQHEGLPKPLT LRW (SEQ ID 080) |

TABLE 1-continued

HLA-B57 alleles

| Sequence identifier (length in aa) | Amino acid sequence |
|---|---|
| B*57:56 HLA07708 (181 aa) | SHSMRYFYTAMSRPGRGEPRFIAVGYVDDTQFVRFDSDAASPRMAHRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 081) |
| B*57:57 HLA07748 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAAREAEQLRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKPLT LRW (SEQ ID 082) |
| B*57:58 HLA08073 (181 aa) | SHSMRYFYTAMSRPGRGEPRFISVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 083) |
| B*57:59 HLA08294 (273 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQISQRKLEAARVAEQLRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKPLT LR (SEQ ID 084) |
| B*57:60 HLA08371 (181 aa) | SHSMRYFYTAMSRPGRGEPRFIAVGYVDDTQFVRFDSDAASPRMAPRAPWIEQE GPEYWDGETRNMKASAQTYRESLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 085) |
| B*57:61 HLA08927 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLGGL CVEWLRRYLENGKETLQRA (SEQ ID 086) |
| B*57:62 HLA08997 (181 aa) | SHSMRYFYTAMSRPGRGEPRFIAVGYVDDTQFVRFDSDAASPRMAPRAPWIEQE GPEYWDGEKRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 087) |
| B*57:63 HLA09303 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAAREAEQRRAYLEGL CVEWLRRYLENGKETLQRA (SEQ ID 088) |
| B*57:64 HLA09312 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAACVAEQLRAYLEGL CVEWLRRYLENGKETLQRA (SEQ ID 089) |
| B*57:65 HLA09577 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAVRVAEQLRAYLEGL CVEWLRRYLENGKETLQRA (SEQ ID 090) |
| B*57:66 HLA09909 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSRTAADTAAQITQRKWEAARVAEQLRAYLEGL CVEWLRRYLENGKETLQRA (SEQ ID 091) |
| B*57:67:01 HLA10038 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDLGPDGRL LRGHDQSAYDGKDYIALNEDLSSWTAADTAAQITQRKWEAARVAEQLRAYLEGL CVEWLRRYLENGKETLQRA (SEQ ID 092) |
| B*57:67:02 HLA14152 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDLGPDGRL LRGHDQSAYDGKDYIALNEDLSSWTAADTAAQITQRKWEAARVAEQLRAYLEGL CVEWLRRYLENGKETLQRA (SEQ ID 093) |
| B*57:68 HLA10040 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITKRKWEAARVAEQLRAYLEGL CVEWLRRYLENGKETLQRA (SEQ ID 094) |

TABLE 1-continued

HLA-B57 alleles

| Sequence identifier (length in aa) | Amino acid sequence |
|---|---|
| B*57:69 HLA10408 (181 aa) | SHSMRYFYTAMSRPGRGEPRFITVGYVDDTLFVRFDSDATSPRKEPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 095) |
| B*57:70 HLA11328 (18 1aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAARVAEQLRAYLEGL CVECLRRYLENGKETLQRA (SEQ ID 096) |
| B*57:71 HLA11950 (273 aa) | SHSMRYFYTAMSRPGRGEPRFITVGYVDDTQFVRFDSDATSPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRADPPKTHVTHHPISDHEATLRCWALGFYPAEITLTW QRDGEDQTQDTELVETRPAGDRTFQKWAAVVVPSGEEQRYTCHVQHEGLPKPLT LRW (SEQ ID 097) |
| B*57:72 HLA12010 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVADQLRAYLEGL CVEWLRRYLENGKETLQRA (SEQ ID 098) |
| B*57:73 HLA12263 (181 aa) | SHSMRYFHTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 099) |
| B*57:74 HLA12294 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSYTIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 100) |
| B*57:75 HLA13002 (181 aa) | SHSMRYFYTAMSRPGRGEPRFIAVGYVDDTQFVRFDSDAASPRMAPRATWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 101) |
| B*57:76 HLA13004 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGRL LRGHDQFAYDGKDYIALNEDLSSWTAADTAAQITQRKWEAARVAEQLRAYLEGL CVEWLRRYLENGKETLQRA (SEQ ID 102) |
| B*57:77 HLA13480 (181 aa) | SHSMRYFYTAMSRPGRGEPRFIAVGYVDDTQFVRFDSDAASPRMAPRAPWIEQE GPEYWDGETRNMKASAQTYRENLRIALRYYNQSEAGSHIIQVMYGCDVGPDGLL LRGHDQSAYDGKDYIALNEDLSSWTAADTAAQITQRKWEAARVAEQLRAYLEGL CVEWLRRYLENGKETLQRA (SEQ ID 103) |
| B*57:78 HLA13379 (181 aa) | SHSMRYFYTAMSRPGRGEPRFIAVGYVDDTQFVRFDSDAASPRMAPWAPWIEQE GPEYWDGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 104) |
| B*57:79N HLA13633 (296 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHIIQVMYGCDVGPDGRLLRGHDQSAYDGKDYIALNEDLSSWTAADT AAQITQRKWEAARVAEQLRAYLEGLCVEWLRRYLENGKETLQRADPPKTHVTHH PISDHEATLRCWALGFYPAEITLTWQRDGEDQTQDTELVETRPAGDRTFQKWAA VVVPSGEEQRYTCHVQHEGLPNPSPX (SEQ ID 105) |
| B*57:80 HLA14154 (181 aa) | SHSMRYFYTAMSRPGRGEPRFISVGYVDDTQFVRFDSDAASPRMAPRAPWIEQE GPEYWDGETRNMKASAQTYRENLRIALRYYNQSEAGSHIIQVMYGCDVGPDGRL LRGHNQYAYDGKDYIALNEDLSSWTAADTAAQITQRKWEAARVAEQLRAYLEGL CVEWLRRYLENGKETLQRA (SEQ ID 106) |
| B*57:81 HLA14308 (181 aa) | SHSMRYFYTAMSRPGRGEPRFIAVGYVDDTQFVRFDSDAASPRMAPRAPWIEQE GPEYWEGETRNMKASAQTYRENLRIALRYYNQSEAGSHIIQVMYGCDVGPDGRL LRGHDQSAYDGKDYIALNEDLSSWTAADTAAQITQRKWEAARVAEQLRAYLEGL CVEWLRRYLENGKETLQRA (SEQ ID 107) |
| B*57:82 HLA14207 (362 aa) | MRVTAPRTVLLLLWGAVALTETWAGSHSMRYFYTAMSRPGRGEPRFIAVGYVDD TQFVRFDSDAASPRMAPRAPWIEQEGPEYWDGETRNMKASAQTYRENLRIALRY YNQSEAGSHTLQRMYGCDVGPDGRLLRGHNQYAYDGKDYIALNEDLSSWTAADT AAQITQRKWEAARVAEQLRAYLEGLCVEWLRRYLENGKETLQRADPPKTHVTHH |

TABLE 1-continued

HLA-B57 alleles

| Sequence identifier (length in aa) | Amino acid sequence |
|---|---|
| | PISDHEATLRCWALGFYPAEITLTWQRDGEDQTQDTELVETRPAGDRTFQKWAA VVVPSGEEQRYTCHVQHEGLPKPLTLRWEPSSQSTVPIVGIVAGLAVLAVVVIG AVVAAVMCRRKSSGGKGGSYSQAACSDSAQGSDVSLTA (SEQ ID 108) |

We claim:

1. An isolated Human Leukocyte Antigen-B57 (HLA-B57) fusion protein, comprising:
   a first and a second monomer, and wherein each monomer independently of the other monomer comprises:
   a HLA-B57 heavy chain,
   an Fc (crystallizable fragment) domain polypeptide sequence, and
   optionally, an amino acid linker joining the HLA-B57 heavy chain and the Fc domain,
   wherein the HLA-B57 chain comprises ≥95% sequence identity to SEQ ID NO: 7.

2. The isolated HLA-B57 fusion protein of claim 1, wherein the first and the second monomer are the same.

3. The isolated HLA-B57 fusion protein of claim 1, wherein the Fc domain comprises heavy chain constant regions $C_H2$ and $C_H3$ selected from the group consisting of immunoglobulin type G (IgG), type A (IgA), type D (IgD), type E (IgE) and type M (IgM).

4. The isolated HLA-B57 fusion protein of claim 1, wherein the amino acid linker comprises 1 to 50 amino acids linking the HLA-B57 chain to the Fc domain as one single polypeptide chain.

5. The isolated HLA-B57 fusion protein of claim 1, wherein the HLA-B57 chain comprises ≥97% sequence identity to SEQ ID NO: 7.

6. The isolated HLA-B57 fusion protein of claim 1, wherein the HLA-B57 chain comprises ≥98% sequence identity to SEQ ID NO: 7.

* * * * *